United States Patent [19]

Weiss et al.

[11] 4,085,272

[45] Apr. 18, 1978

[54] 11-(2-HYDROXYETHYLTHIO)PROSTENOIC ACID $E_2$ SERIES DERIVATIVES

[75] Inventors: Martin Joseph Weiss, Oradell, N.J.; Gerald Joseph Siuta, Yonkers, N.Y.

[73] Assignee: American Cyanamid Company, Stamford, Conn.

[21] Appl. No.: 782,853

[22] Filed: Mar. 30, 1977

[51] Int. Cl.$^2$ .......................................... C07C 177/00
[52] U.S. Cl. ......................... 560/121; 260/345.8 P; 260/395; 260/448.8 R; 260/514 D; 542/429; 424/305; 424/317
[58] Field of Search ................ 260/514 D, 468 D, 69

[56] References Cited

U.S. PATENT DOCUMENTS

| | | | |
|---|---|---|---|
| 3,845,042 | 10/1974 | Strike et al. | 260/240 |
| 3,876,690 | 4/1975 | Floyd et al. | 260/514 |
| 3,932,487 | 1/1976 | Kramer et al. | 260/468 |
| 4,018,820 | 4/1977 | Fried | 260/514 |
| 4,028,396 | 7/1977 | Schaub et al. | 260/468 |

OTHER PUBLICATIONS

Burger, Medicinal Chemistry, pp. 77–78, (1963).

*Primary Examiner*—Robert Gerstl
*Attorney, Agent, or Firm*—Denis A. Polyn

[57] ABSTRACT

This disclosure describes certain 11-(2-hydroxyethylthio)-9-keto-prostenoic acid E series derivatives, and their intermediates, useful as bronchodilators and inflammatory medeator release inhibitors.

23 Claims, No Drawings

11-(2-HYDROXYETHYLTHIO)PROSTENOIC ACID $E_2$ SERIES DERIVATIVES

BACKGROUND OF THE INVENTION

Applicants are not aware of any prior art references which, in their respective judgments as one skilled in the prostaglandin art, would anticipate or render obvious the novel compounds of the instant invention; however, for the purpose of fully developing the background of the invention and establishing the state of the requisite art, the following reference is set forth: U.S. Pat. No. 3,876,690, which discloses certain 11-(2-hydroxyethoxy)-9-keto and 9-hydroxy-prostenoic acid derivatives.

BRIEF SUMMARY OF THE INVENTION

This invention relates to novel 11-(2-hydroxyethylthio)13-trans-prostenoic acids and esters as well as to the cyclopentenone intermediates and processes for their preparation. The novel compounds of this invention embrace all the possible optical isomers, diastereomers and enantiomers, racemates, and racemic mixtures represented by the following general formulae of the naturally occurring mammalian prostaglandins.

The first embodiment of the invention is represented by an optically active compound of the formula:

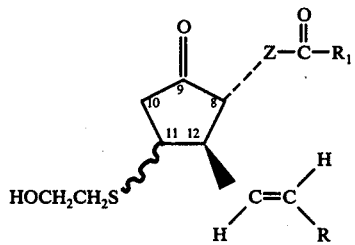

wherein Z is a divalent moiety selected from the group consisting of —$(CH_2)_6$— and

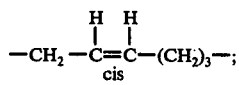

$R_1$ is selected from the group consisting of hydroxy and $C_1$–$C_6$ alkoxy; and R is a moiety selected from the group consisting of

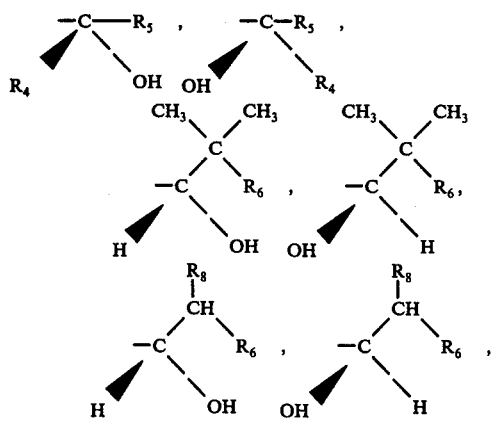

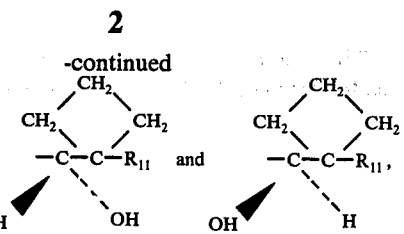

wherein $R_4$ is selected from the group consisting of hydrogen and methyl, $R_5$ is selected from the group consisting of $C_4$–$C_7$ alkyl and 2-cis($C_4$–$C_6$) alkenyl, $R_6$ is selected from the group consisting of $C_3$–$C_5$ alkyl, $R_8$ is selected from the group consisting of $C_1$–$C_2$ alkyl, and $R_{11}$ is selected from the group consisting of $C_3$–$C_7$ alkyl; with the proviso that when $R_5$ is 2-cis($C_4$–$C_6$)-alkenyl, then $R_4$ must be hydrogen and Z must be

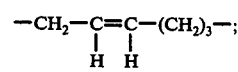

the racemic mixture thereof; the mirror image thereof; and when $R_1$ is hydroxy, the pharmaceutically acceptable salts thereof.

A preferred embodiment of the first embodiment consists of those compounds wherein Z, R and $R_1$ are as previously defined; and the substituent at the carbon-11 position is β-(2-hydroxyethylthio).

A second preferred embodiment of the first embodiment consists of those compounds wherein Z, R and $R_1$ are as previously defined; and the substituent at the carbon-11 position is α-(2-hydroxyethylthio).

A most preferred embodiment of the second preferred embodiment consists of those compounds wherein Z and $R_1$ are as previously defined; and R is a moiety selected from the group consisting of

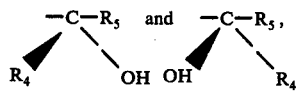

wherein $R_4$ and $R_5$ are as previously defined.

A second most preferred embodiment of the second preferred embodiment consists of those compounds wherein Z and $R_1$ are as previously defined; and R is a moiety selected from the group consisting of

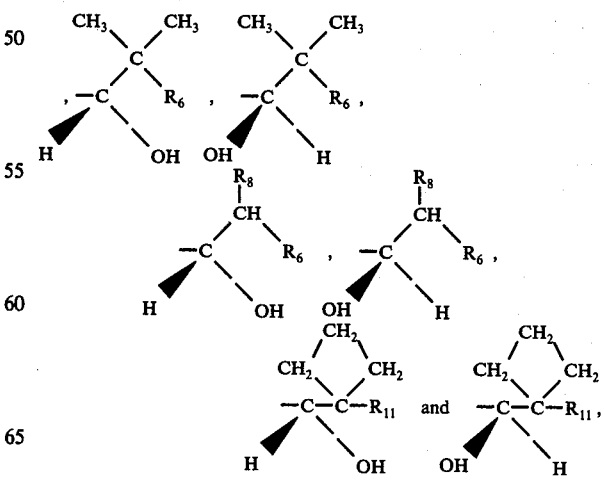

wherein $R_6$, $R_8$ and $R_{11}$ are as previously defined.

The second embodiment of the invention is represented by an optically active compound of the formula:

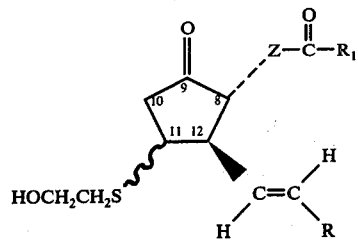

wherein Z is a divalent moiety selected from the group consisting of —(CH$_2$)$_6$- and

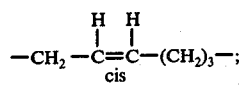

R$_1$ is selected from the group consisting of hydroxy and C$_1$-C$_6$ alkoxy; and R is a moiety selected from the group consisting of

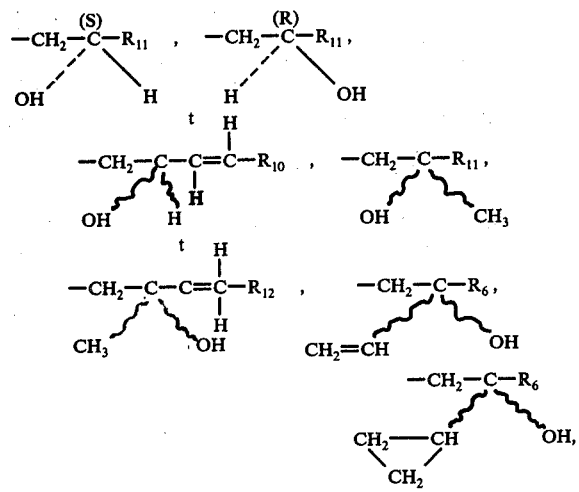

wherein R$_6$ is selected from the group consisting of C$_3$-C$_5$ alkyl, R$_7$ is selected from the group consisting of C$_2$-C$_4$ alkyl, R$_{10}$ is selected from the group consisting of C$_1$-C$_4$ alkyl, R$_{11}$ is selected from the group consisting of C$_3$-C$_7$ alkyl and R$_{12}$ is selected from the group consisting of C$_1$-C$_3$ alkyl; the racemic mixture thereof; the mirror image thereof; and when R$_1$ is hydroxy, the pharmaceutically acceptable salts thereof.

A preferred embodiment of the second embodiment consists of those compounds wherein Z, R and R$_1$ are as previously defined; and the substituent at the carbon-11 position is β-(2-hydroxyethylthio).

A second preferred embodiment of the second embodiment consists of those compounds wherein Z, R and R$_1$ are as previously defined; and the substituent at the carbon-11 position is α-(2-hydroxyethylthio).

A most preferred embodiment of the second preferred embodiment consists of those compounds wherein Z and R$_1$ are as previously defined; and R is a moiety selected from the group consisting of

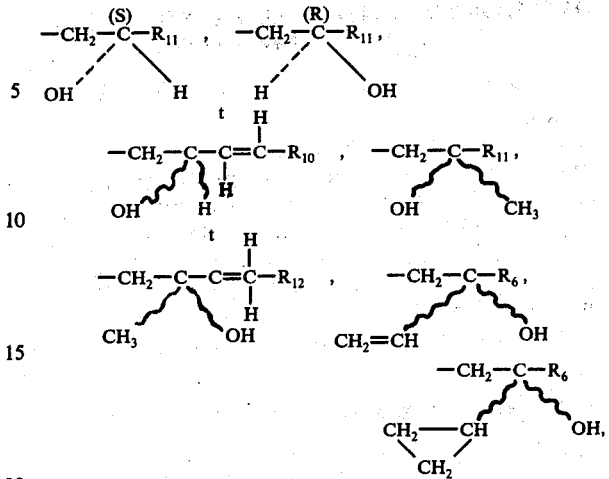

wherein R$_6$, R$_{10}$, R$_{11}$ and R$_{12}$ are as previously defined.

A second most preferred embodiment of the second preferred embodiment consists of those compounds wherein Z and R$_1$ are as previously defined; and R is a moiety selected from the group consisting of

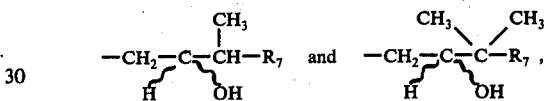

wherein R$_7$ is as previously defined.

A still further preferred embodiment of the second most preferred embodiment consists of those compounds wherein Z and R$_1$ are as previously defined; and R is

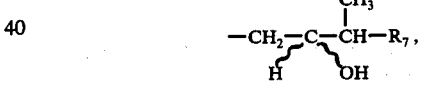

wherein R$_7$ is as previously defined.

A still further preferred embodiment of the first most preferred embodiment consists of those compounds wherein Z and R$_1$ are as previously defined; and R is a moiety selected from the group consisting of

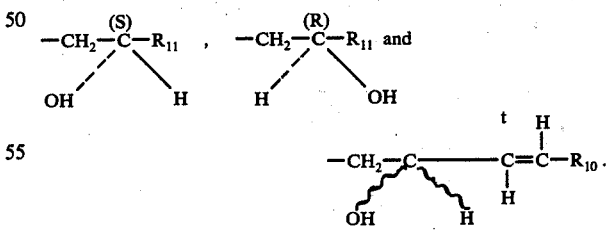

A second still further preferred embodiment of the first most preferred embodiment consists of those compounds wherein Z and R$_1$ are as previously defined; and R is a moiety selected from the group consisting of

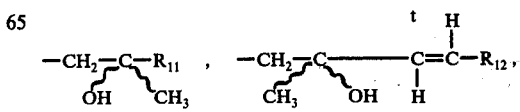

-continued

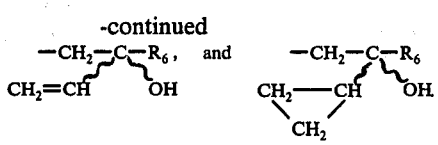

The third embodiment of the invention is represented by an optically active compound of the formula:

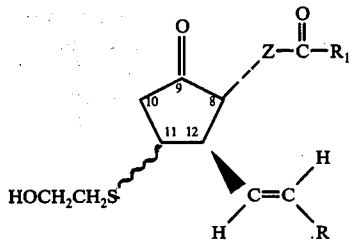

wherein Z is a divalent moiety selected from the group consisting of —(CH$_2$)$_6$- and

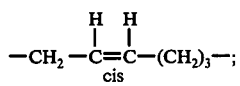

R$_1$ is selected from the group consisting of hydroxy and C$_1$-C$_6$ alkoxy; and R is a moiety selected from the group consisting of

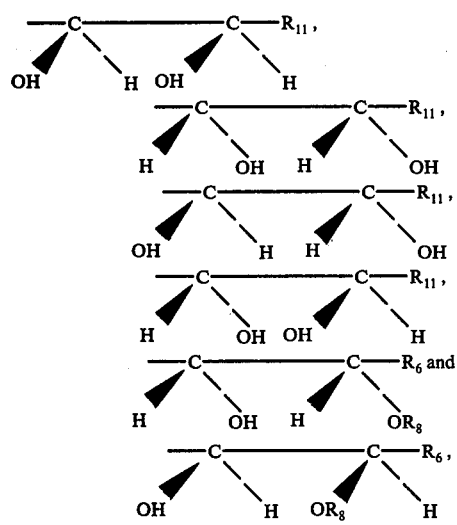

wherein R$_6$ is selected from the group consisting of C$_3$-C$_5$ alkyl, R$_8$ is selected from the group consisting of C$_1$-C$_2$ alkyl and R$_{11}$ is selected from the group consisting of C$_3$-C$_7$ alkyl; the racemic mixture thereof; the mirror image thereof; and when R$_1$ is hydroxy, the pharmaceutically acceptable salts thereof.

A preferred embodiment of the third embodiment consists of those compounds wherein Z, R and R$_1$ are as previously defined; and the substituent at the carbon-11 position is β-(2-hydroxyethylthio).

A second preferred embodiment of the third embodiment consists of those compounds wherein Z, R and R$_1$ are as previously defined; and the substituent at the carbon-11 position is α-(2-hydroxyethylthio).

A most preferred embodiment of the second preferred embodiment consists of those compounds wherein R$_1$ and Z are as previously defined; and R is a moiety selected from the group consisting of

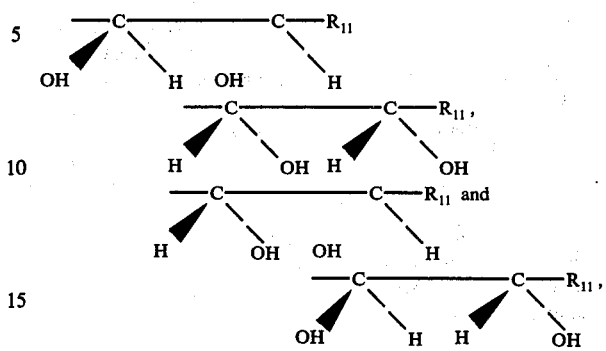

wherein R$_{11}$ is as previously defined.

An optically active compound according to claim 66, wherein R$_1$ and Z are as previously defined; and R is a moiety selected from the group consisting of

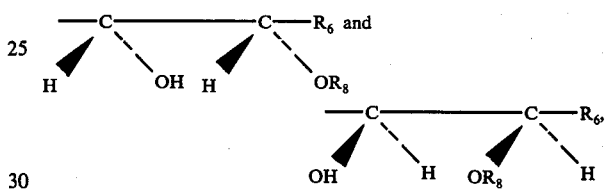

wherein R$_6$ and R$_8$ are as previously defined.

The fourth embodiment of the invention is represented by a compound of the formula:

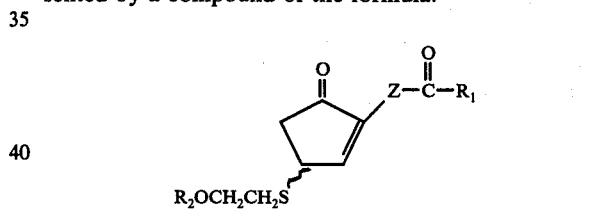

wherein Z is a divalent moiety selected from the group consisting of —(CH$_2$)$_6$- and

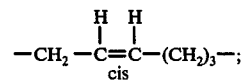

R$_1$ is selected from the group consisting of hydroxy, C$_1$-C$_6$ alkoxy, trityloxy, tetrahydropyranyloxy and tri-(C$_1$-C$_6$)alkylsilyloxy; and R$_2$ is selected from the group consisting of hydrogen, trityl, tetrahydropyranyl and tri-(C$_1$-C$_6$)alkylsilyl.

A preferred embodiment of the fourth embodiment consists of those compounds wherein R$_1$ and R$_2$ are as previously defined; and Z is

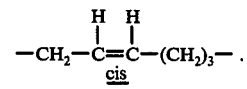

A most preferred embodiment of the preferred embodiment consists of those compounds wherein Z is as previously defined; R$_1$ is selected from the group consisting of hydroxy, C$_1$-C$_6$ alkoxy and tri(C$_1$-C$_6$)alkylsilyl; and $R_2$ is selected from the group consisting of hydrogen and tri($C_1$-$C_6$)alkylsilyl.

Useful pharmacologically acceptable salts of the above formula, where $R_1$ is hydroxyl, are those with pharmacologically acceptable metal cations, ammonium, amine cations or quaternary ammonium cations.

Preferred metal cations are those derived from the alkali metals, e.g. lithium, sodium and potassium, and from the alkaline earth metals, e.g. magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexlamine, decylamine, dodecylamine, allylamine, crotylamine, cyclopentylamine, dicyclohexylamine, mono- or dibenzylamine, α- or β-phenylethylamine, ethylenediamine, diethylenetriamine, and araliphatic amines containing up to and including 18 carbon atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic solutions are preferred. For that purpose it is preferred, because of increased water solubility, that $R_1$ be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

DETAILED DESCRIPTION OF THE INVENTION

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom, et. al., J. Biol. Chem., 238, 3555 (1963) and Horton, Experientia, 21, 113 (1965) and references cited therein. All of the so called natural prostaglandins are derivatives of prostanoic acid:

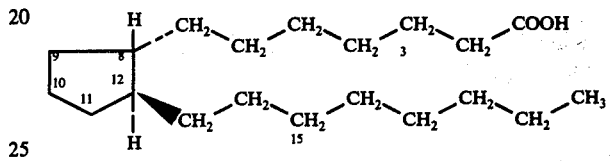

The hydrogen atoms attached to C-8 and C-12 are in transconfiguration. The natural prostaglandins represent only one of the possible optical isomers. The compounds of this invention include all possible optical isomers and racemates.

The configuration of substituents on the prostaglandin molecule are designed to be in the α-configuration if they lie beneath the plane of the molecule as drawn above and are designated with a — bond. Those substituents which lie above the plane of the molecule as drawn above are designated β and are represented by a ▬bond.

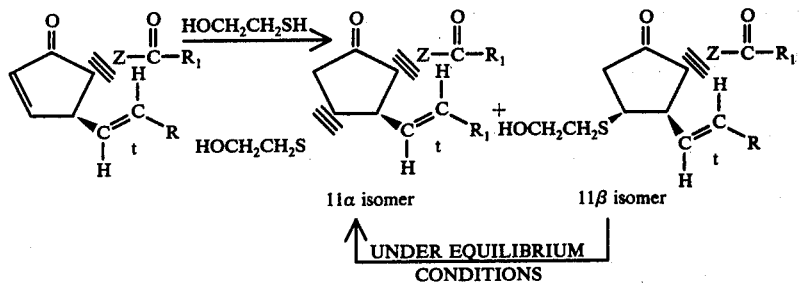

The natural $PGE_1$, $PGE_2$ and $PGE_3$ compounds are potent in causing multiple biological responses, even at low doses. As a bronchodilator, the natural prostaglandins have an inconveniently short duration of activity. In striking contrast, the novel 11-deoxy-11α/β-(2-hydroxyethylthio) PGE analogs of this invention possess a significantly longer duration of bronchodilation in the guinea pig Konzett assay.

Bronchodilator activity is determined in guinea pigs against bronchospasms elicited by intravenous injections of 5-hydroxytryptamine, histamine of acetylcholine by the Konzett procedure. [See J. Lulling, P. Lievens, F. El Sayed and J. Prignot, Arzneimittel-Forschung, 18, 995 (1968)].

In the Table I which follows, bronchodilator activity for representative compounds of this invention against one or more of the three spasmogenic agents is expressed as an $ED_{50}$ determined from the results obtained with three logarithemic cumulative intravenous doses.

TABLE I

| Compound Tested | $ED_{50}$ in mg/kg | | | Potency (Range 0–4) |
|---|---|---|---|---|
| | 5-HT | HIST. | ACH. | |
| 1-11α/β-(2-hydroxyethylthio)-11-deoxy-PGE$_2$ methyl ester (Example 223) | $8.8^{-3}$ | $4.24^{-3}$ $44.2^{-3}$ | $27.5^{-3}$ $391^{-3}$ | 4 (1) |
| 1 11α-(2-hydroxyethylthio)-11-deoxy-PGE$_2$ methyl ester (Example 229) | $5.9^{-3}$ $35^{-3}$ | $4.87^{-3}$ | $11.1^{-3}$ | 4 |
| 1 11β-(2-hydroxyethylthio)-11-deoxy-PGE$_2$ methyl ester (Example 229) | $60^{-3}$ | $45.5^{-3}$ | $62.8^{-3}$ $671^{-3}$ | 4 |
| 1 11α/β-(2-hydroxyethylthio)-11,deoxy-PGE$_1$ (Example 228) | $5.5^{-3}$ $34^{-3}$ $78^{-3}$ | $4.7^{-3}$ $36.^{-3}$ $71^{-3}$ | $11^{-3}$ $61^{-3}$ $221^{-3}$ | 4 |
| dl 11α/β-(2-hydroxyethylthio)-11,15-bisdeoxy-16-hydroxy-PGE$_1$ (Example 226) | $19^{-3}$ $82^{-3}$ $288^{-3}$ | $19.5^{-3}$ $150^{-3}$ | $53^{-3}$ | 3 |
| dl 11α/β-(2-hydroxyethylthio)-11,15-bisdeoxy-16-hydroxy-16-methyl-PGE$_2$ (Example 225) | $17^{-3}$ $77^{-3}$ $257^{-3}$ | $20^{-3}$ $108^{-3}$ | $34^{-3}$ | 3 |

In addition, compounds of this invention possess the additional ability to function as inflammatory medeator release inhibitors as assayed using sensitized human basophiles.

The novel compounds of the present invention can be readily prepared from certain PGA derivatives which may be represented by the following general formula:

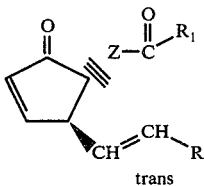

trans wherein R, R$_1$, and Z are as hereinabove described.

The preparation of the requisite PGA intermediates from the corresponding PGE compounds is described [Corey, E. J., Jour. Amer. Chem. Soc., 90, 3245 (1968)], or can be obtained by analogous procedures to those described in the aforesaid reference.

The 11-(2-hydroxyethylthio)-prostenoic acids and esters of this invention may be prepared by addition of 2-mercoptoethanol to the PGA derivative in the presence of a catalytic amount of an organic base such as triethylamine. In the absence of a catalysis, the reaction proceeds slowly. The product is obtained as a mixture of epimers at C-11 which are readily separable by column chromatrography on silica-gel.

It has been found, however, if the amount of catalysis is increased, or the reaction temperature is increased, or the duration of the reaction is increased, then the 11α-isomer product will predominate over the 11β-isomer.

The novel compounds of this invention can also be prepared by 1,4 - conjugate addition involving treatment of the ether blocked cyclopentenone (71) with a lithio-cuprate reagent such as (68), (69), or (70) prepared as illustrated in Flowsheets A through H.

The 1,4 - conjugate addition procedure is described hereinbelow in Flowsheet H. The preparation of the various requisite 1-iodo-trans- b 1-alkenyl or 1-tributyl-stannyl-trans-1-alkenyl derivative is illustrated in Flowsheets A through F and the novel and important synthesis of 4-(2-hydroxyethylthio)-cyclopentenone is described in connection with Flowsheet G.

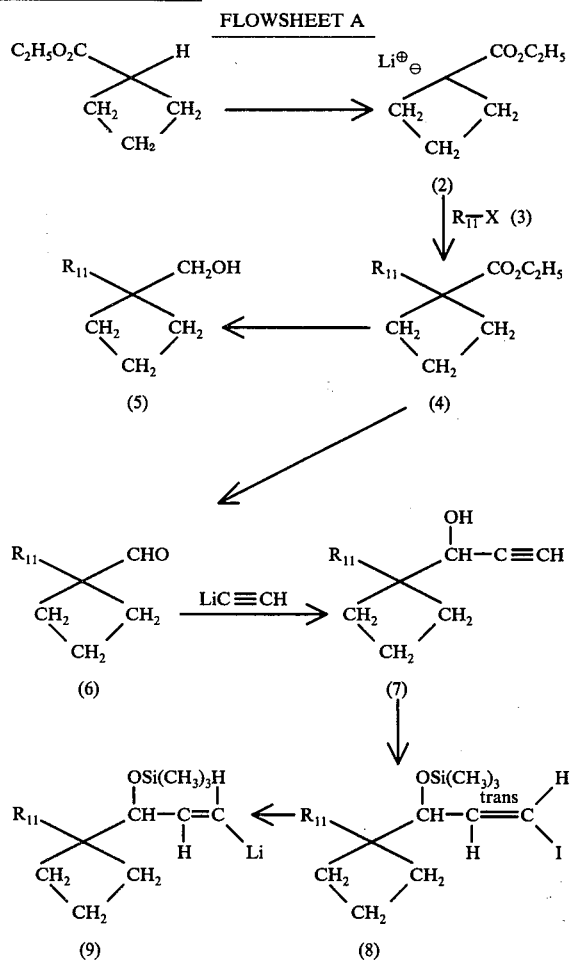

FLOWSHEET A

In accordance with the scheme as outlined hereinabove in Flowsheet A, carbethoxycyclobutane is converted to its enolate anion (2) by treatment with a strong base such as lithium cyclohexylisopropylamide, prepared from the corresponding amine and n-butyl lithium (hexane solution) in a solvent, such as anhydrous tetrahydrofuran, at very low temperatures, such as 78° C. The resulting enolate anion (2) is then alkylated with R$_{11}$-X (3) to provide (4), the ester group of which is reduced to alcohol (5) by reaction with 2 equivalents of diisobutyl aluminum hydride, lithium aluminum hydride or the like. Oxidation of alcohol (5) with dipyridine chromium oxide complex ["Reagents for Organic Synthesis", L. F. Fieser and M. Fieser, John Wiley and Sons, Inc., New York, 4, 215 (1974)], prepared in situ in methylene chloride solution, provides the corresponding aldehyde (6), which can also be obtained directly from ester (4) by partial reduction with one equivalent of diisobutyl aluminum hydride at −78° C, but the former two-step procedure is preferable. Reaction of aldehyde (6) with lithium acetylide ethylene diamine complex provides the 3-hydroxy-1-alkyne (7), which is converted to its trimethylsilyl ether in the usual manner.

The silylated derivative is then treated with disiamylborane (prepared in situ in tetrahydrofuran solution at ice bath temperatures from 2-methyl-2-butene, sodium borohydride and boron trifluoride etherate) and then anhydrous trimethylamine oxide. The resulting solution and an iodine solution in tetrahydrofuran are then added simultaneously to an agueous solution of sodium hydroxide to give the 1-iodo-3-trimethylsilyloxy-4,4-trimethylene-1-alkene (8).

FLOWSHEET B

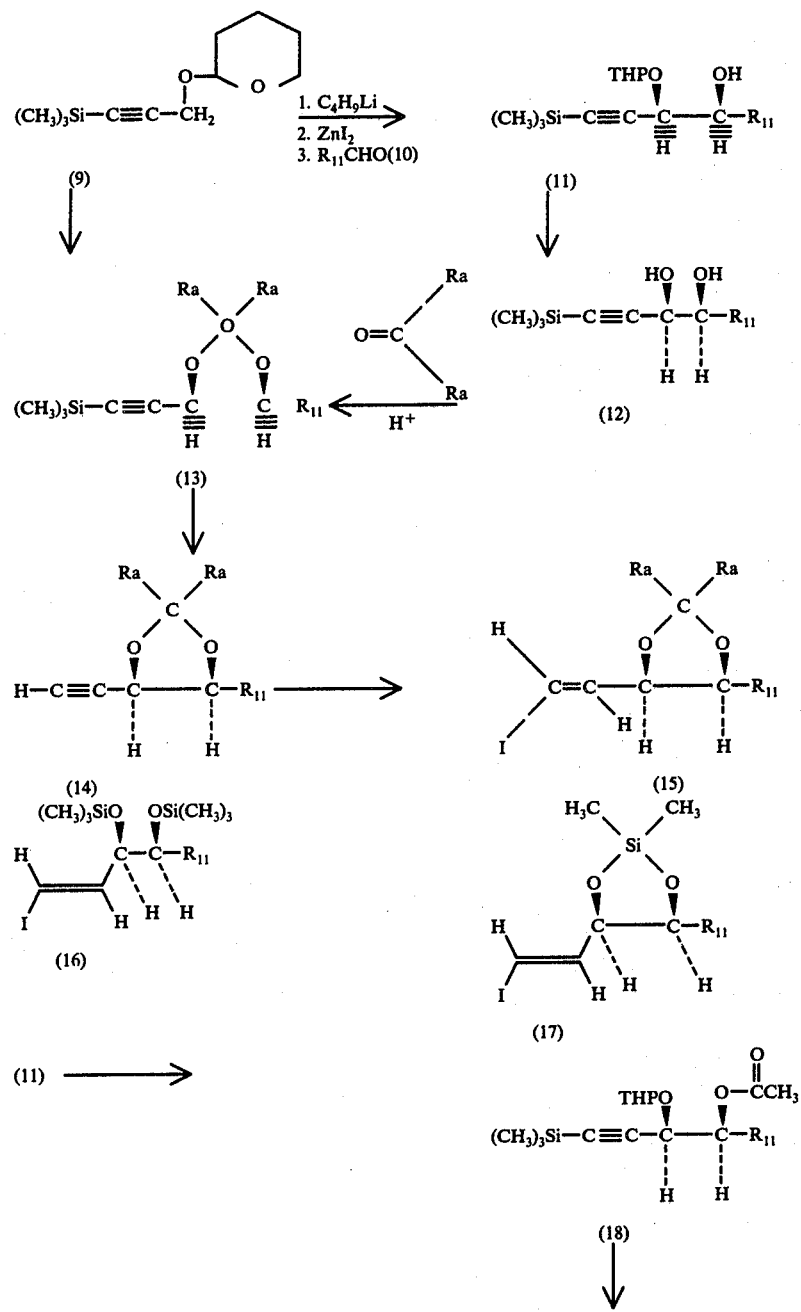

4,085,272
-continued
FLOWSHEET B
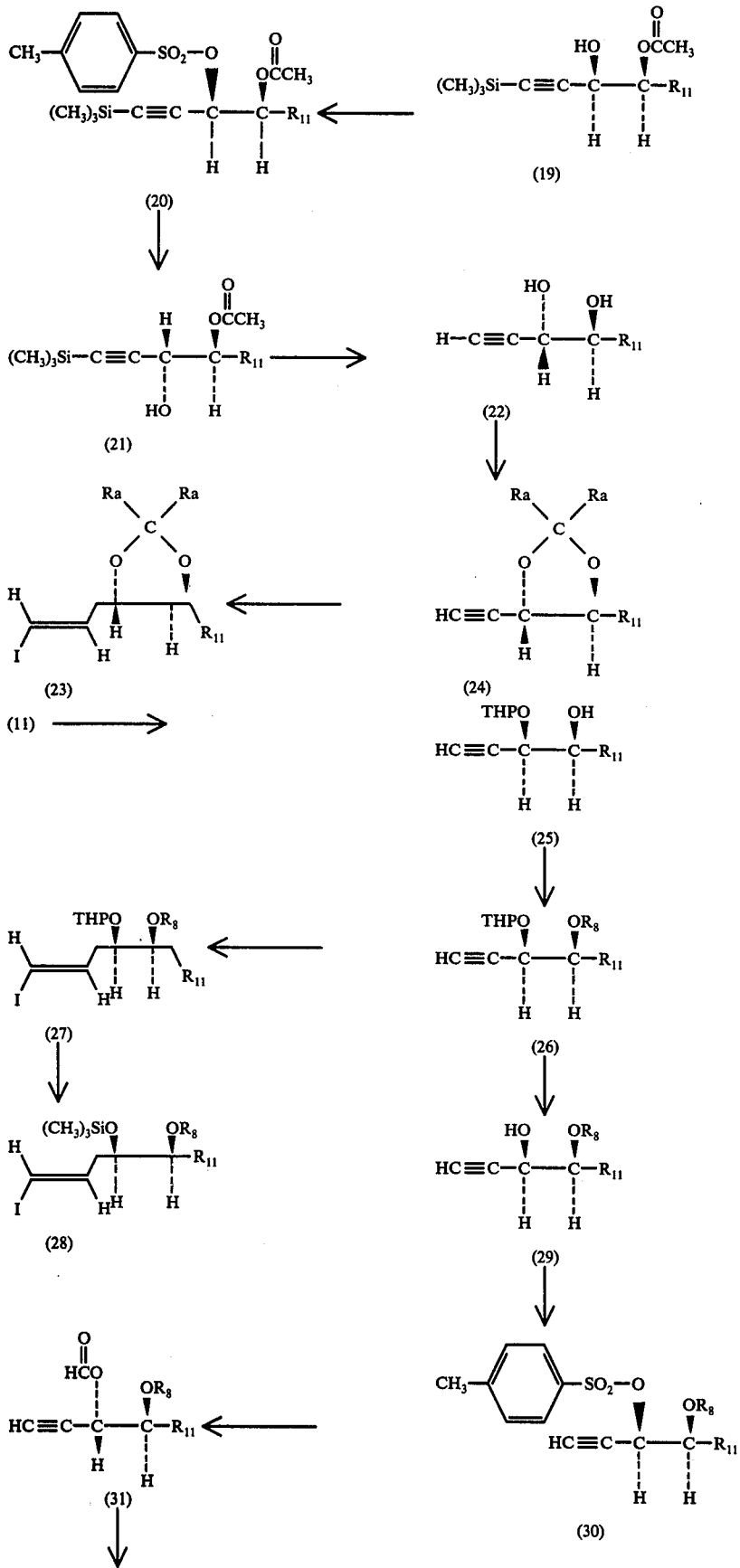

FLOWSHEET B -continued

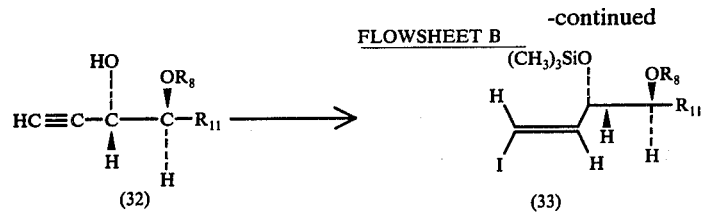

In accordance with the scheme as outlined hereinabove in Flowsheet B, 1-trimethylsilyl-3-tetrahydropyranyloxy-1-propyne (9) is treated with n-butyllithium at −78° C and then with a freshly prepared solution of zinc iodide in anhydrous tetrahydrofuran, also at −78° C. Reaction of aldehyde (10) with the resulting reagent then provides the 4-hydroxy-3-tetrahydropyranyloxy-1-alkyne (11). This reaction procedes with great stereoselectivity and the product (11) is in the erythro configuration. [For additional information concerning this reaction see the examples which follow and F. Mercier, R. Epstein and S. Holland, Bull. Soc. Chim. France, 690 (1972).]

The tetrahydropyranyl group in (11) is removed on weak acid treatment and the resulting erythro diol (12) can be reblocked by treating with an appropriate aldehyde or ketone

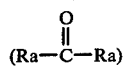

in the presence of strong acid catalyst in the usual way to give the ketal or acetal (13). Acetone is a useful ketone for this purpose and the product (13) is then a 3,4-isopropylidenedioxy-1-alkyne. It is also possible to utilize silyl blocking groups (introduced after removal of the 1-trimethylsilyl group) to ultimately give the vinyl iodides (16) or (17). Weak base treatment of (13), for example heating for about one hour in refluxing methanol with potassium carbonate, results in desilylation to give (14). The 1-alkene (14) is converted to the corresponding 1-iodo-trans-1-alkene (15) by treatment with disiamylborane (prepared in situ in tetrahydrofuran solution at ice bath temperatures from 2-methyl-2-butene, sodium borohydride and boron trifluoride etherate) and then anhydrous trimethylamine oxide. The resulting solution and an iodine solution in tetrahydrofuran are then added simultaneously to an aqueous solution of sodium hydroxide to give (15).

For the preparation of the threo derivatives, the 4-hydroxy-3-tetrahydropyranyloxy-1-alkyne (11) is acetylated to provide the corresponding 4-acetoxy derivative (18). The tetrahydropyranyl group is preferentially hydrolyzed with weak acid to (19), which is then tosylated in the usual manner to afford the erythro-3-tosyloxy-4-acetoxy-1-alkyne (20). Solvolysis of (20) under essentially neutral conditions by heating in aqueous tetrahydrofuran in the presence of an insoluble acid-acceptor, such as calcium carbonate, results in inversion of $C_3$, furnishing the threo-3-hydroxy-4-acetoxy-1-alkyne (21), which is then deblocked with aqueous base to give the threo-3,4-diol (22). Diol (22) is converted to an acetal or ketal (23) (or silyl derivatives as in (16) or (17)] and thence to the 1-iodo-trans-1-alkene (16) as described hereinabove wherein Ra is lower alkyl ($C_1$ to $C_3$).

For the preparation of the 16-alkoxyprostanoic acids of this invention, the erythro-4-hydroxy-3-tetrahydropyranyloxy-1-alkyne (11) is desilylated by methanol-potassium carbonate treatment and the resulting (25) is etherified to give the 4-alkoxy-3-tetrahydropyranyloxy-1-alkyne (26). A useful procedure for this last step involves treatment of (25) with a molar equivalent of sodium hydride to give the 4-alkoxide which is then alkylated with the appropriate alkylating agent, for example methyl iodide. The 4-alkoxy-1-alkyne (26) is then converted to the corresponding 1-iodo-trans-1-alkene (27) as described hereinabove for the preparation of (15). If desired the tetrahydropyranyl blocking group in (27) can be hydrolyzed (weak acid) and the resulting free 3-ol corresponding to (27) converted to the 3-trimethylsilyloxy derivative (28), all in the usual manner wherein $R_8$ is lower alkyl ($C_1$ to $C_3$).

For the threo series, the tetrahydropyranyl group in erythro-4-alkoxy-1-alkyne (26) is cleaved and the resulting 3-hydroxy-4-alkoxy-1-alkyne (29) is tosylated to give the erythro-3-tosyloxy-4-alkoxy-1-alkyne (30). $S_n2$ displacement reaction with (30) with reagents such as tetrahydroammonium formate results in inversion to the threo derivative (31) saponification of which provides threo-3-hydroxy-4-alkoxy-1-alkyne (32). Trimethylsilylation followed by the vinyl iodide conversion procedure described hereinabove furnishes the threo-1-iodo-1-alkene (33) wherein $R_8$ is hydrogen or lower alkyl ($C_1$ to $C_3$).

The 15-alkyl and/or 16-alkyl derivatives of this invention can be prepared by substituting

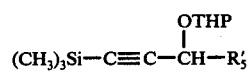

for (4) and/or

for (6) ($R'_5$ = lower alkyl of 1 to 3 carbons) in Flowsheet B.

In accordance with the procedure as outlined in Flowsheet C, an aldehyde (34) is treated with propargylic magnesium halide to form the homopropargylic alcohol (35), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride etherate) and then anhydrous trimethylamine oxide. The resulting solution and an iodine solution in tetrahydrofuran are then added simultaneously to an aqueous solution of sodium hydroxide to give the 1-iodo-4-trimethylsilyloxy-trans-1-alkene (36), precursors for 16-hydroxy-prostaglandin.

The trimethylsilyl protecting group is removed with mild acid and the resulting vinyl iodide alcohol is oxidized with pyridinium chlorochromate to provide the 1-iodo-4-oxo-trans-1-alkene (37), which upon treatment with a Grignard reagent ($R_{12}MgX$) provides the 1-iodo-4-hydroxy-trans-1-alkene, which is silylated in the usual manner to provide the silyl ether (38) wherein $R_{11}$ is lower alkyl ($C_3$ to $C_7$) and $R_{12}$ is vinyl or cyclopropyl.

FLOWSHEET C

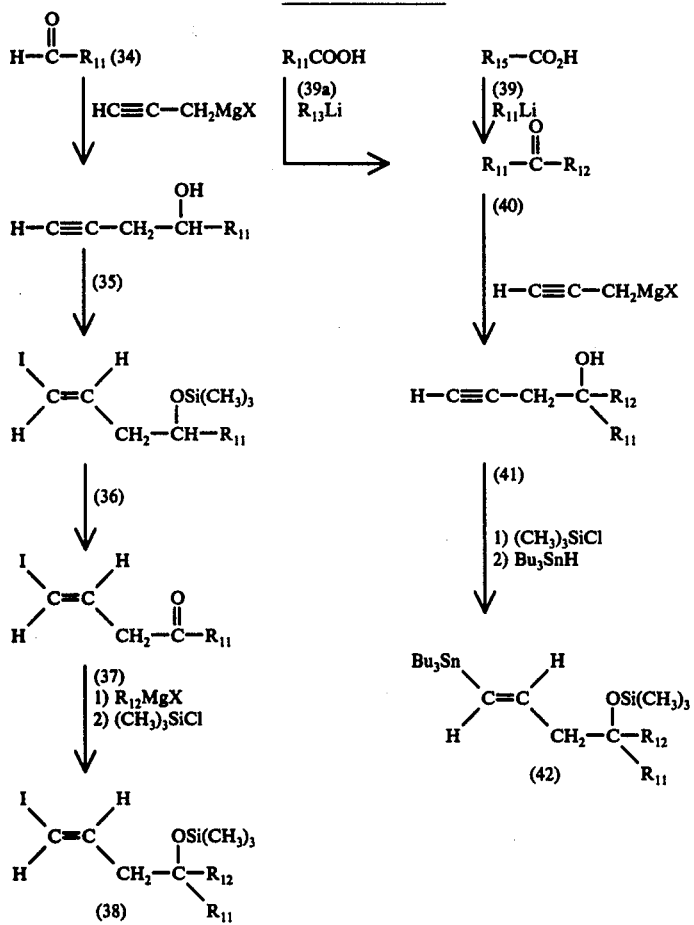

A more preferred method for the preparation of vinyllithium precursor is also described in Flowsheet C. Treatment of the requisite carboxylic acid (39a or 39) with the appropriate organolithium reagent ($R_{12}Li$ or $R_{11}Li$ respectively), wherein $R_{11}$ and $R_{12}$ are hereinabove defined, give the corresponding ketone (40) which upon treatment with propargylic magnesium halide provides the homopropargylic alcohol (41) which is converted to the trans vinylstannyl derivative by sequential treatment with chlorotrimethylsilane and tri-n-butyltin hydride. Treatment of the vinylstannyl reagent (42) with n-butyllithium at a temperature of $-10°$ C to $-78°$ C generates the corresponding vinyllithium reagent.

FLOWSHEET D

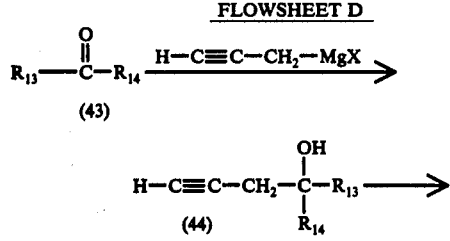

-continued

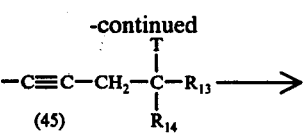

In accordance with Flowsheet D hereinabove, the precursors for other 16-hydroxy prostaglandins are prepared by treating an appropriate aldehyde or ketone (43) with a propargylic magnesium halide to yield the requisite homopropargylic alcohol (44). The alcohol is protected as a tritylether (45) (for secondary alcohols) or as a trimethylsilylether (45) (for tertiary alcohols). These ethers are then converted to the appropriate trans-vinyliodide (46) by treatment with disiamylborane generated in situ from 2-methyl-2-butene, sodium borohydride, and boron trifluoride, follwoed by treatment with trimethylamine oxide and then iodine and sodium hydroxide, wherein $R_{13}$ is hydrogen and methyl, T is $O—C(C_6H_5)_3$ when $R_{13}$ is hydrogen and T is $O—Si(CH_3)_3$ when $R_{13}$ is methyl; $R_{14}$ is selected from the group comprising lower alkyl ($C_3$ to $C_5$), lower 1-alkenyl ($C_3$ to $C_5$),

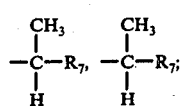

wherein R$_7$ is as described above; with the provision that when R$_{14}$ is

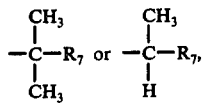

then R$_{13}$ must be hydrogen.

FLOWSHEET E

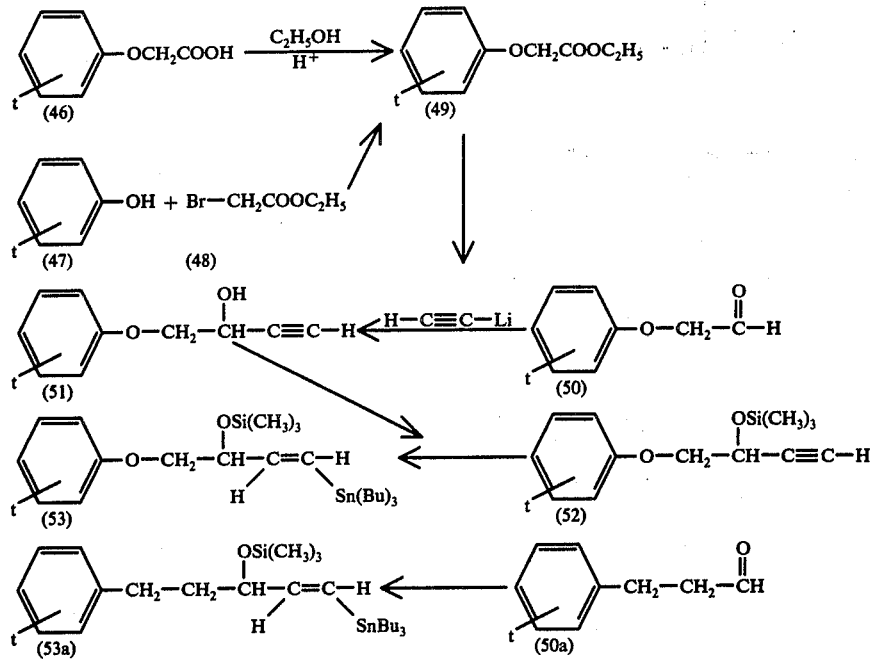

FLOWSHEET F

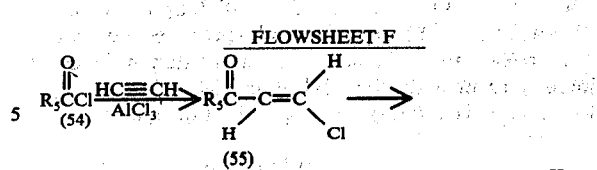

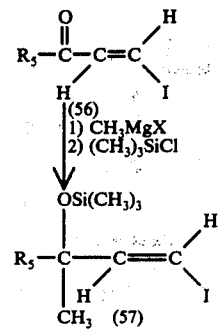

The preparation of the precursors for the synthesis of 16-aryloxy and 17-phenyl congeners is described in accordance with Flowsheet E hereinabove. The aryl esters (49) are prepared by esterifying the commerically available acids or by treatment of ethyl bromoacetate with the appropriate phenol. The ester (49) is carefully reduced to the aldehyde (50) which upon treatment with lithium acetylide provides the propargylic alcohol (51). Treatment of the alcohol (51) with chlorotrimethylsilane followed by tri-n-butyltin hydride furnishes the requisite vinylstannyl derivative (53). Similar treatment starting with substituted hydrocinnamaldehyde (50a) provides the respective vinylstannyl derivative (53a).

The preparation of the precursors for the synthesis of secondary 15-hydroxy congeners are described in the literature. The preparation of the precursor for 15-methyl-15-hydroxy is described in Flowsheet F hereinbelow. In accordance with Flowsheet F, an acid chloride, wherein R$_5$ is hereinabove defined, is treated with acetylene and aluminum trichloride to provide the vinylchloride (55) which upon treatment with sodium iodide furnishes the vinyliodide (56). Treatment of (56) with methylmagnesium halide followed by chlorotrimethylsilane gives the requisite protected vinyliodide (57).

Certain of the requisite 4-(2-hydroxyethylthio)-cyclopentenones may be prepared from the corresponding 4-hydroxy or alkoxy cyclopentenones Ia in accordance with the reaction scheme of Flowsheet G or from the 3-hydroxy cyclopentenones Ib, also described in Flowsheet G.

The requisite 4-alkoxy cyclopentenones are described in U.S. Pat. No. 3,876,690 or can be obtained by analogous procedures to those described in the aforesaid patent. The 3 and 4-hydroxy-cyclopentenones are described in U.S. Pat. Nos. 3,966,773 and 3,952,033.

FLOWSHEET G

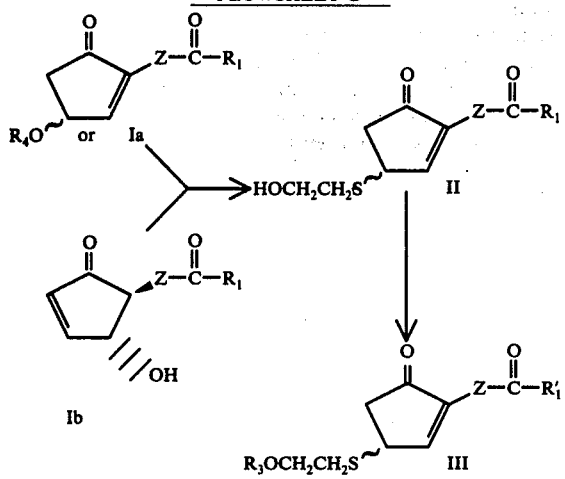

In accordance with the scheme as outlined hereinabove in Flowsheet G wherein $R_3$ is triloweralkylsilyl, tetrahydropyranyl or triphenylmethyl, $R_1'$ is $C_1$–$C_6$ alkoxy, tetrahydropyranyloxy, triloweralkylsilyloxy, or triphenylmethoxy and $R_4$ and $R_1$ are hereinabove defined, the cyclopentenones Ia or Ib are treated with 1-equivalent of 2-mercoptoethanol in the presence of sodium methoxide and methanol for between 1–5 hours at room temperature affording the 4-(2-hydroxyethylthio)-cyclopentenones (II), which are converted into their trimethylsilyl, tetrahydropyranyl or triphenylmethyl ether esters (III) in the usual manner.

The preparation of the prostaglandin congeners of this invention are described in Flowsheet H wherein R' is selected from the group consisting of:

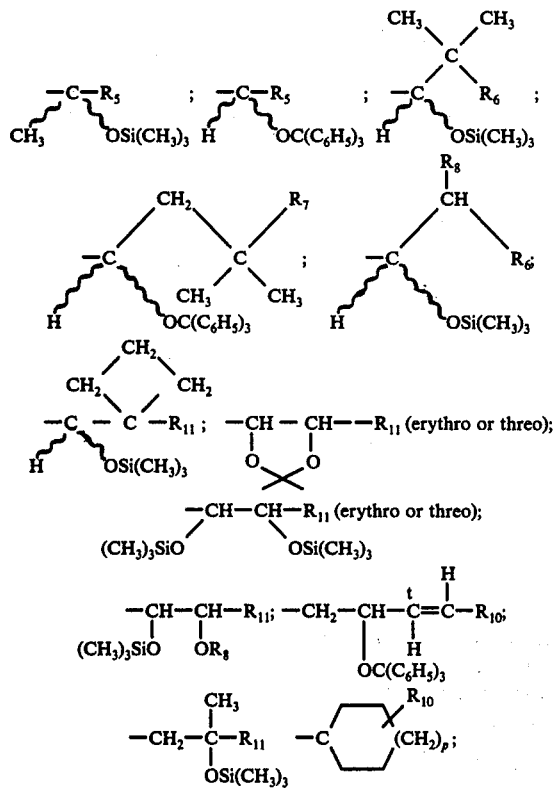

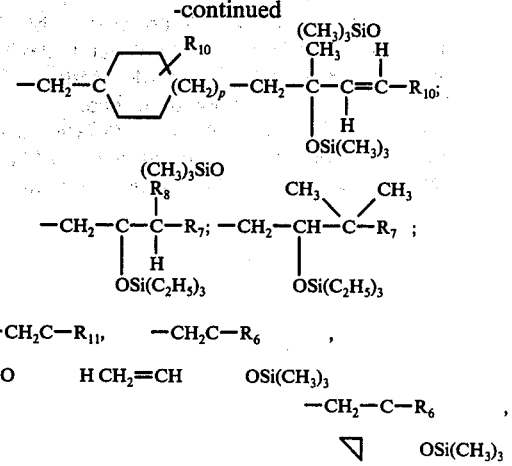

wherein $R_5$, $R_6$, $R_7$, $R_8$, $R_{10}$, $R_{11}$, and $R_{12}$ are as hereinabove defined, and $p$ is 1 or 2.

In accordance with Flowsheet H, a suitably protected vinyliodide (65) is treated with either one equivalent of n-butyllithium or 2 equivalents of t-butyllithium at low temperature, preferably −30° to −78° C in an inert solvent, eg. hexane, ether or toluene to provide the trans-alkenyl-lithium reagent (67).

Alternatively, the vinyllithium reagent (67) can be prepared by treatment of a vinylstannyl derivative such as (66) with n-butyllithium at −10° to −78° C.

For the preparation of the asymmetrical lithio cuprate (68) or the like, a solution of one molar equivalent of copper (I)-1-alkyne, preferable copper (I)-1-pentyne in anhydrous tributyl phosphine, preferably one to five molar equivalents, and anhydrous ether is added to one molar equivalent of the aforementioned vinyllithium solution cooled to about −79° C. After about one hour at this temperature, a molar equivalent of the requisite cyclopentenone (71) is added. After several hours at −30° C to −70° C the reaction mixture is quenched with aqueous ammonium chloride solution and the blocked product (72) is isolated in the usual manner.

It is also possible to effect conjugate 1,4-addition with the asymmetrical lithio cuprate (70) derived from vinyllithium (67) and cuprous throphenoxide. A solution of vinyllithium (67) in ether at −78° C is reacted with an equimolar amount of a reagent prepared by admixture, in ether at a temperature of 0° C to −78° C, of equimolar amounts of cuprous thiophenoxide and copper (I) iodide tributylphosphonium complex. After about 30 minutes at this temperature, the lithio cuprate (70) is treated with the requisite cyclopentenone (71) as described hereinabove for the conjugate addition with 1-alkynyl lithio cuprate (68).

For the preparation of the symmetrical lithio cuprate (69) one molar equivalent of copper (I) iodide tributylphosphine complex, dissolved in anhydrous ether, is added at about −78° C to two molar equivalents of the aforementioned vinyl iodide (65) solution in hexanes, cooled to −78° C. After about one hour at this temperature, the lithio cuprate (69) is treated with the requisite cyclopentenone (71) as described hereinabove, for the conjugate addition with the 1-alkynl lithio cuprate (68).

The procedures for conjugate addition involving organocopper reagents are well known in the art, see for example, C. J. Sih, et. al., J. A. C. S., 97, 865 (1975).

In the cases where $R'_1$ = trimethylsilyloxy in cyclopentenone (71) the conjugate addition is performed at −78° C to −40° C. The reaction is quenched by addition of an ether solution of acetic acid. Removal of blocking groups is then carried out as described in the reference above to provide the product (73) wherein $R_1$ and R are hereinabove described.

All available evidence leads us to believe that the δ-chain introduced by the cuprate process occupies a position trans to the 11-oxy function. Similarly, we are led to the conclusion that in the product (73) the two side-chains attached to $C_8$ and $C_{12}$ are trans to each other. However, we are not certain of this configurational relationship in the product as it is obtained directly from the cuprate process. These products may have the side-chain in a trans or cis-relationship or they may be a mixture containing both the trans- and cis-isomers. This is indicated in the nomenclature of the compounds involved by the designation 8ε. In order to ensure a trans-relationship in (73) these products can be submitted to conditions known in the literature to equilibrate the cis-8-iso-$PGE_1$ to a mixture containing about 90% of the trans product. These conditions involve treatment with potassium acetate in aqueous methanol for 96 hours at room temperature.

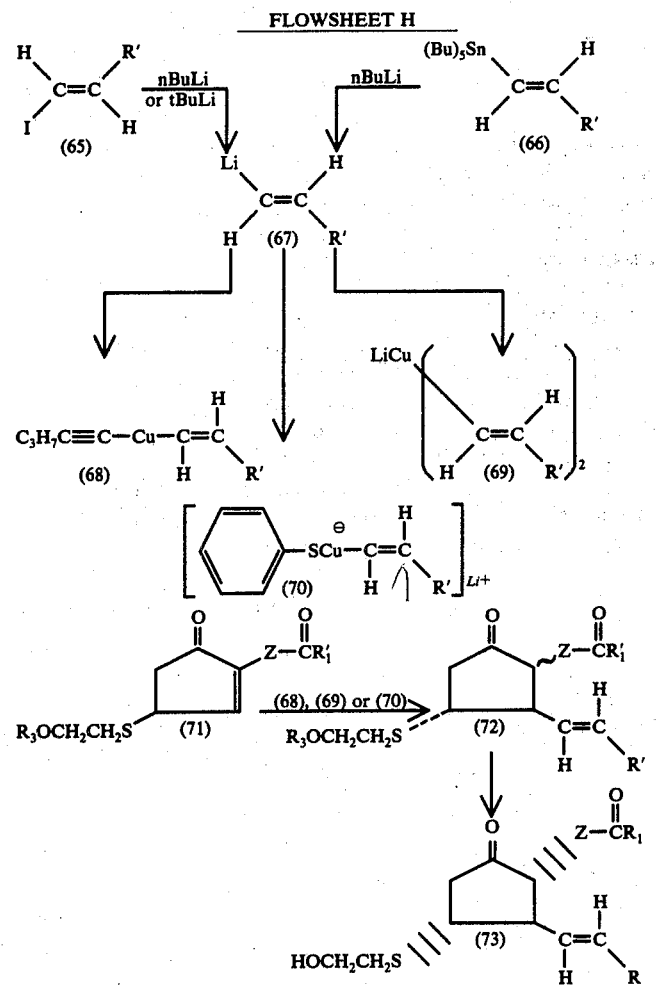

FLOWSHEET H

The 9-keto derivatives of this invention can be converted to the corresponding 9-hydroxy derivatives as described in Flowsheet I. If this conversion is effected with sodium borohydride, the product is a mixture of 9α- and 9β-hydroxy derivatives (75) and (76) respectively, as set forth in the following reaction scheme, wherein $R_1$, R and Z are as hereinabove defined.

FLOWSHEET I

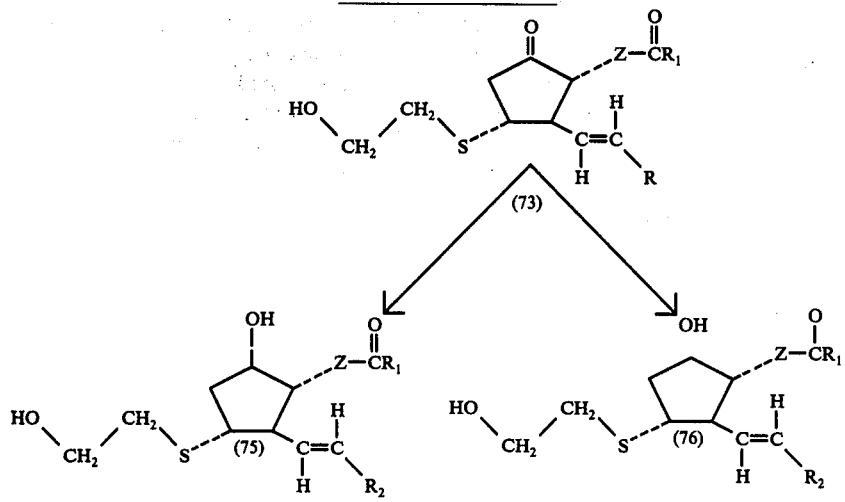

When the reaction is carried out with lithium perhydro-9b-boraphenylyl hydride [H. C. Brown and W. C. Dickason, J.A.C.S., 92, 709 (1970)]or lithium tris-(t-butyl)-borohydride [H. C. Brown and S. Krishnamurthy, ibid., 94, 7159 (1972)] the product is at least predominantly the 9α-hydroxy derivative wherein the 9-hydroxy group is cis to the side chain attached to C8 and to the 11-mercapto function. In accordance with accepted convention, an α-substituent at the 8-, 9-, 11- or 12-positions is behind the plane of the paper, whereas a β-substituent at these positions is in front of the plane of paper. This is usually represented by a — bond for an α-substituent, a ▬ bond for a β-substituent, and a ▬ bond where both are indicated.

The carboxylic acids of this invention can be readily converted to the various alkyl esters of this invention by treatment in the usual manner with the appropriate diazoalkane. The preparation of diazoalkanes by various procedures are well described in the art. See for example C. D. Gutsche, Organic Reactions, 8, 389, (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C to 15° C with a molar equivalent of a tri-alkylamine, preferably triethylamine, tributylamine and the like, and then a molar equivalent of isobutyl chlorocarbonate or the like. The resulting mixed anhydrides is then treated with the appropriate alcohol to give the derivatized product. [For a pertinent literature analogy see Prostaglandins, 4, 738 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see German Offen. No. 2,365,205; Chem. Abst., 81, 120098g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information concerning high speed liquid chromatography and the instruments necessary for its application is available from Water Associate Inc., Maple Street, Mildord, Mass.]

In addition, optically active congeners can be prepared by treating a racemic mixture of a cyclopentenone (71) with the cuprate derived from an optically active vinyliodide such as (77) to give two diasteriomers (78) and (79) as shown in Flowsheet J. Chromatographic separation by the usual methods, after removal of the protecting groups, will then provide both the nat (78) and ent (79) epimers possessing the same absolute configuration at the carbon bearing the hydroxyl vinyl cuprate precursor.

Methods for the resolution of the vinyliodides or precursors to the vinyliodides such as propargylic or homopropargylic alcohols are known in the art. [J. Fried, et. al., Annals. New York Acadamy of Science, 180, 60 (1971); R. Pappo, et. al., Ibid, 180, 66 (1970); A. F. Kluge, et. al., J.A.C.S., 94, 7827 (1972); U.S. Pat. No. 3,950,446].

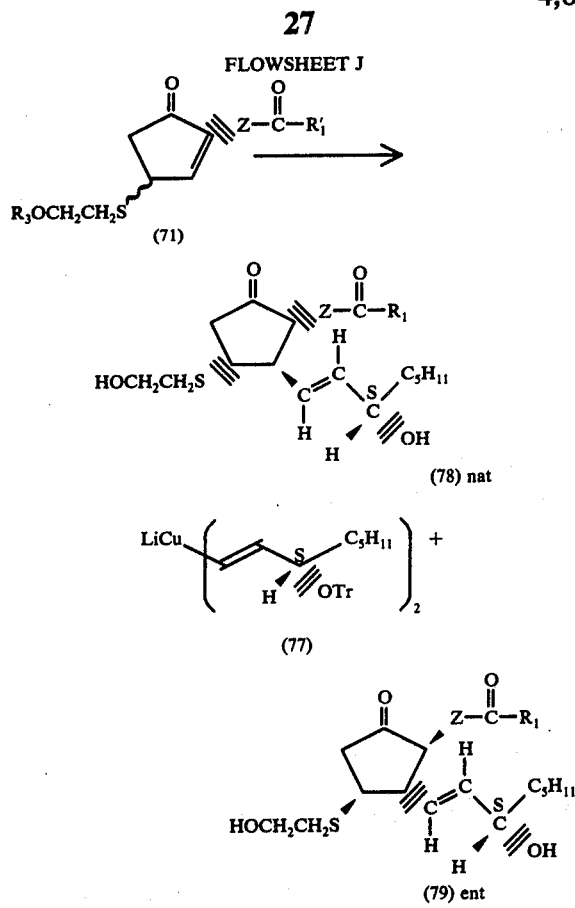

FLOWSHEET J

EXAMPLE 1

Preparation of ethyl 2,2-trimethylenehexanoate

To a stirred solution of 27.6 g of freshly distilled N-isopropylcyclohexylamine in 200 ml of dry tetrahydrofuran cooled to −78° C is added at a fast rate 96 ml of 2.04M n-butyllithium in hexane. To the resulting solution is added dropwise 25 g of ethyl cyclobutanecarboxylate. After 30 minutes the resulting solution is allowed to warm to ambient temperature, is transferred to a dropping funnel under nitrogen and is added dropwise over a period of 1¼ hours to a solution of 54 g of n-butyl iodide in 100 ml of dry dimethylsulfoxide maintaining the temperature at 16°−20° C. Stirring is continued for an additional 30 minutes. The separated salts are removed by filtration, the mother liquor is taken to a small volume and the resulting oil is diluted with hexanes. This solution is washed with 2% hydrochloric acid, saturated sodium chloride solution, and dried with anhydrous magnesium sulfate. The solvent is removed and the residual oil is distilled to give 14.6 g (41%) of product, bp 84°−87° C (10 mm).

EXAMPLE 2

Preparation of ethyl 2,2-tetramethylenehexanoate

In the manner described in Example 1, treatment of the lithium salt of ethyl cyclopentanecarboxylate with n-butyl iodide furnishes the subject product.

EXAMPLE 3

Preparation of 2,2-trimethylenehexan-1-ol

To a stirred solution of 20 g of ethyl 2,2-trimethylenehexanoate (Example 1) in 100 ml of dry toluene, in an argon atmosphere and cooled in an ice bath, is added dropwise 250 ml (2 molar equivalents) of 0.89M diisobutylaluminum hydride in toluene. The resulting solution is stirred at ambient temperature for 2 hours and then poured into excess iced 5% hydrochloric acid. The organic phase is separated and washed with 5% hydrochloric acid, saturated sodium chloride solution, dried with anhydrous magnesium sulfate and taken to dryness to give 14.8 g (96%) of oil; bp 92°−93° C (10 mm).

EXAMPLE 4

Preparation of 2,2-trimethylenehexan-1-ol

In the manner described in Example 3, treatment of ethyl 2,2-tetramethylenehexanoate (Example 2) with 0.89 molar diisobutylaluminum hydride furnishes the subject product.

EXAMPLE 5

Preparation of 2,2-trimethylenehexaldehyde

Chromium trioxide (61.5 g), dried in a vacuum desiccator over phosphorous pentoxide, is added to an ice cold solution of 97 g of dry pyridine in one liter of dry methylene chloride. The deep red suspension is stirred for 15 minutes at 0° C and then for 45 minutes at ambient temperature. A solution of 14.5 g of 2,2-trimethylenehexanol-1 (Example 3) in 55 ml of methylene chloride is added all at once to the suspension. A black tarry deposit is formed immediately. After stirring at ambient temperature for 15 minutes the solution is decanted from the tarry deposit which is then triturated four times with small portions of methylene chloride. The combined extracts are washed twice with ice cold 5% sodium hydroxide, ice cold 5% hydrochloric acid and finally with saturated sodium chloride solution, dried with magnesium sulfate and taken to dryness. Distillation gives 12.9 g of product; bp 69° C (11 mm).

EXAMPLE 6

Preparation of 2,2-trimethylenehexaldehyde

Oxidation of 2,2-trimethylenehexan-1-ol (Example 4) with chromium trioxide-pyridine complex in the manner described in Example 5 furnishes the subject product.

EXAMPLE 7

Preparation of 4,4-trimethylene-1-octyn-3-ol

To a solution of lithium acetylide-ethylenediamine complex (9.4 g) in 90 ml of dry dimethylsulfoxide, cooled in an ice bath, is added 12.94 g of 2,2-trimethylenehexaldehyde (Example 5) in 10 ml of dimethylsulfoxide dropwise, at such a rate that the temperature is maintained at 20°−25° C. The solution is stirred at ambient temperature for 12 hours and then poured into a mixture of ice cold 2% hydrochloric acid and ether. The ether layer is separated and the aqueous phase is extracted with ether. The combined ether extracts are washed with saturated sodium chloride solution, dried with anhydrous magnesium sulfate and taken to dryness. Distillation provides 13.53 g of product; bp 108°−109° C (13 mm).

EXAMPLE 8

Preparation of 4,4-tetramethylene-1-octyn-3-ol

Treatment of 2,2-tetramethylenehexaldehyde (Example 6) with lithium acetylide-ethylenediamine complex in dimethylsulfoxide in the manner described in Example 4 is productive of the subject compound.

EXAMPLE 9

Preparation of 4,4-trimethylene-3-trimethylsilyloxy-1-octyne

To a stirred solution of 5.3 g of 4,4-methylene-1-octyn-3-ol (Example 7) and 5.42 g of imidazole in 32 ml of dry dimethylformamide, cooled in an ice bath under argon atmosphere is added 4.35 g of chlorotrimethylsilane. After stirring at 0° C for 15 minutes, the solution is stirred at ambient temperature for 18 hours and then poured into 200 ml of hexanes. The solution is washed twice with ice cold water, saturated sodium chloride solution, dried with anhydrous magnesium sulfate and taken to dryness. Distillation furnishes 6.02 g (80%) of colorless oil; bp 110°-112° C (14 mm).

EXAMPLE 10

Preparation of 4,4-tetramethylene-3-trimethylsilyloxy-1-octyne

Treatment of 4,4-tetramethylene-1-octyn-3-ol (Example 8) with chlorotrimethylsilane in dimethylformamide containing imidazole as described in Example 5 furnishes the subject product.

EXAMPLE 11

Preparation of 1-iodo-4,4-trimethylene-3-trimethylsilyloxy-1-octyne

To a solution of 25 g of 4,4-trimethylene-3-trimethylsilyloxy-1-octyne (Example 9), stirred under argon atmosphere at −78° C, is added dropwise 93 ml of 2.3M n-butyllithium in hexane at a rate to maintain the temperature below −40° C. After stirring for 40 minutes, a solution of iodine is allowed to warm to ambient temperature and 10% aqueous sodium thiosulfate solution is added until the purple color is removed. The organic phase is washed with dilute aqueous sodium thiosulfate solution, saturated sodium chloride solution, dried with anhydrous sodium sulfate and taken to dryness to afford the subject product as an oil.

EXAMPLE 12

Preparation of 1-iodo-4,4-trimethylene-3-trimethylsilyloxy-1-cis-octene

To a solution of 30 g of 1-iodo-4,4-trimethylene-3-trimethylsilyloxy-1-octyne (Example 10) in 100 ml of methanol, under argon atmosphere is added 54 g of potassium azodicarboxylate [J. Thiele, Annalen der Chemie, 271, 127 (1892)]. To this solution is added dropwise 45 ml of acetic acid over a period of about 2 hours. The solids are removed by filtration and the mother liquor is reduced to a small volume, diluted with water and extracted with ether. The ether is evaporated and the residual oil is stirred with 250 ml of 1M sodium bicarbonate solution. The solution is extracted several times with ether and the combined extracts are washed with saturated sodium chloride solution, dried with anhydrous sodium sulfate and taken to dryness to furnish the subject product as an oil.

EXAMPLE 13

Preparation of 1-iodo-4,4-trimethylene-3-trimethylsilyloxy-1-trans-octene

To a mixture of 4.76 g of sodiumborohydride and 23.6 g of 2-methyl-2-butene in 220 ml of dry tetrahydrofuran at −5° C is added dropwise 23.8 g of freshly distilled borontrifluoride etherate. The resulting mixture is stirred at −5° C to −0° C for 2 hours and to it is added dropwise a solution of 20 g of 4,4-trimethylene-3-trimethylsilyloxy-1-octyne (Example 12) in 20 ml of dry tetrahydrofuran. The resulting mixture is stirred at ambient temperature for 2½ hours. The mixture is then cooled to −5° C and there is added 44 g of trimethylene oxide protionwise over a period of 20 minutes, maintaining the temperature at 15°−20° C. The mixture is stirred at ambient temperature for 2 hours and then poured simultaneously, with a solution of 119 g of iodine in 290 ml of tetrahydrofuran, into 1490 ml of 15% aqueous sodium hydroxide solution. After stirring for 30 minutes the organic phase is separated and he aqueous phase is extracted with ether. The combined organic phase is washed with 5% aqueous sodium thiosulfate solution, saturated sodium chloride solution, dried with anhydrous magnesium sulfate and taken to dryness to give 27 g of oily material. Chromatography on 135 g of florisil and eluting with 500 ml of hexanes furnishes 24 g of oily product which is shown to be contaminated with starting material and iodoform by infrared and thin layer chromatography. The material is purified by removing the trimethylsilyl group in the following manner. The crude product is dissolved in 350 ml of acetic acid-tetrahydrofuran-water (4:2:1) by stirring at ambient temperature for 5 minutes. The solvent is removed under reduced pressure and the residual oil containing mainly 1-iodo-3-hydroxy-4,4-trimethylene-1-trans-octene is applied to a 2" (flat) dry column containing 1200 g of Woelm silica gel. The column is developed with benzene, cut into one-inch segments and each segment is eluted with chloroform. Combination of the appropriate fractions affords 300 mg of iodomethane, 2.8 g of 4,4-trimethylene-1-octyne-3-ol, and 11.6 g of 1-iodo-3-hydroxy-4,4-trimethylene-1-trans-octene. Silylation of this material in the manner described above followed by distillation of the residual oil furnishes 13 g of pure product; bp 83°-84° C (0.2 mm).

EXAMPLE 14

Preparation of 1-iodo-4,4-tetramethylene-3-trimethylsilyloxy-1-trans-octene

Treatment of 4,4-tetramethylene-3-trimethylsilyloxy-1-octyne (Example 10) in the manner described in Example 13 furnishes the subject product.

EXAMPLES 15-20

Treatment of the lithium salt of ethyl cyclobutanecarboxylate with the alkyl halides listed in Table 1 below by the procedure described in Example 1 furnishes the 2,2-trimethylene esters of the table.

TABLE 1

| Example | Alkyl Halides | Product 2,2-Trimethylene esters |
|---|---|---|
| 15 | propyl iodide | ethyl 2,2-trimethylenepentanoate |
| 16 | amyl iodide | ethyl 2,2-trimethyleneheptanoate |
| 17 | hexyl iodide | ethyl 2,2-trimethyleneoctanoate |
| 18 | benzyl iodide | ethyl 2,2-trimethylene-3-phenyl- |

TABLE 1-continued

| Example | Alkyl Halides | Product 2,2-Trimethylene esters |
|---|---|---|
| | | propionate |
| 19 | 2-cyclopentyl-1-ethyl bromide | ethyl 2,2-trimethylene-4-cyclopentylbutyrate |
| 20 | 1-chloro-2-butyne | ethyl 2,2-trimethylene-4-hexynoate |

EXAMPLES 21–27

Reduction of the various esters listed in Table 2 below with diisobutylaluminum hydride all in the manner described in Example 3 above is productive of the alcohols of the table.

TABLE 2

| Example | Starting Esters of Example | Product Alcohols |
|---|---|---|
| 21 | 15 | 2,2-trimethylenepentan-1-ol |
| 22 | 16 | 2,2-trimethyleneheptan-1-ol |
| 23 | 17 | 2,2-trimethyleneoctan-1-ol |
| 24 | 18 | 2,2-trimethylene-3-phenyl-propan-1-ol |
| 25 | 19 | 2,2-trimethylene-4-cyclopentylbutan-1-ol |
| 26 | 20 | 2,2-trimethylene-4-hexyn-1-ol |
| 27 | 55 | 2,2-trimethylene-4-cis-hexen-1-ol |

EXAMPLES 28–34

Oxidation of the alcohols listed in Table 3 below with chromium trioxide-pyridine complex by the procedure described in Example 5 above furnishes the corresponding aldehydes of the table.

TABLE 3

| Example | Starting Alcohols of Example | Product 2,2-Trimethylenealdehydes |
|---|---|---|
| 28 | 21 | 2,2-trimethylenevaleraldehyde |
| 29 | 22 | 2,2-trimethyleneheptaldehyde |
| 30 | 23 | 2,2-trimethyleneoctaldehyde |
| 31 | 24 | 2,2-trimethylene-3-phenyl-propionylaldehyde |
| 32 | 25 | 2,2-trimethylene-4-cyclopentylbutyraldehyde |
| 33 | 26 | 2,2-trimethylenehex-4-yn-1-al |
| 34 | 27 | 2,2-trimethylene-4-cis-hexene-1-al |

EXAMPLES 35–41

Treatment of the various aldehydes listed below in Table 4 with lithium acetylide-ethylenediamine complex in the manner described in Example 7 furnishes the hydroxyacetylenes of the table.

TABLE 4

| Example | Starting Aldehydes of Example | Product Hydroxyacetylenes |
|---|---|---|
| 35 | 28 | 4,4-trimethylene-1-heptyn-3-ol |
| 36 | 29 | 4,4-trimethylene-1-nonyn-3-ol |
| 37 | 30 | 4,4-trimethylene-1-decyn-3-ol |
| 38 | 31 | 4,4-trimethylene-5-phenyl-1-pentyn-3-ol |
| 39 | 32 | 4,4-trimethylene-6-cyclopentyl-1-hexyn-3-ol |
| 40 | 33 | 4,4-trimethylene-1,6-octadiyn-3-ol |
| 41 | 34 | 4,4-trimethylene-4-cis-hexene-3-ol |

EXAMPLES 42–48

Treatment of the various alcohols listed below in Table 5 with chlorotrimethylsilane in the manner described in Example 9 furnishes the corresponding trimethylsilyloxy acetylenes of the table.

TABLE 5

| Example | Starting Alcohols of Example | Product Trimethylsilyloxyacetylenes |
|---|---|---|
| 42 | 35 | 4,4-trimethylene-3-trimethylsilyloxy-1-heptyne |
| 43 | 36 | 4,4-trimethylene-3-trimethylsilyloxy-1-nonyne |
| 44 | 37 | 4,4-trimethylene-3-trimethylsilyloxy-1-decyne |
| 45 | 38 | 4,4-trimethylene-3-trimethylsilyloxy-5-phenyl-1-pentyne |
| 46 | 39 | 4,4-trimethylene-3-trimethylsilyloxy-6-cyclo-pentyl-1-hexyne |
| 47 | 40 | 4,4-trimethylene-3-trimethylsilyloxy-1,6-octadiyne |
| 48 | 41 | 4,4-trimethylene-3-trimethylsilyloxy-4-cis-octene-1-yne |

EXAMPLES 49–54

In the manner described in Example 13 treatment of the various acetylenes of Table 6 below with disiamylborane, made in situ from sodium borohydride and 2-methyl-2-butene, followed by oxidation of the so formed organoborane with trimethylamine oxide followed by treatment of this product with iodine and sodium hydroxide furnishes the trimethylsilyliodovinylcarbinols of the table.

TABLE 6

| Example | Starting Acetylenes of Example | Product Trimethylsilylvinylcarbinols |
|---|---|---|
| 49 | 42 | 1-iodo-4,4-trimethylene-3-trimethylsilyloxy-1-trans-heptene |
| 50 | 43 | 1-iodo-4,4-trimethylene-3-trimethylsilyloxy-1-trans-nonene |
| 51 | 44 | 1-iodo-4,4-trimethylene-3-trimethylsilyloxy-1-trans-decene |
| 52 | 45 | 1-iodo-4,4-trimethylene-3-trimethylsilyloxy-5-phenyl-1-trans-pentene |
| 53 | 46 | 1-iodo-4,4-trimethylene-3-trimethylsilyloxy-6-cyclopentyl-1-trans-hexene |
| 54 | 47 | 1-iodo-4,4-trimethylene-3-trimethylsilyloxy-1-trans-octen-6-yne |

EXAMPLE 55

Preparation of ethyl 2,2-trimethylene-4-cis-hexenoate

A solution of 5 g of ethyl 2,2-trimethylene-4-hexynoate (Example 20) in 40 ml of dry pyridine is hydrogenated in a Parr apparatus using 600 mg of 5% palladium on barium sulfate. After one hour when hydrogen uptake is complete, the solution is filtered through celite and the mother liquor is taken to dryness to furnish 4 g of product as an oil.

EXAMPLE 56

Preparation of 3-tetrahydropyranyloxy-1-propyne

To a stirred solution of 112 g (2.0 mol.) of 3-hydroxy-1-propyne and 260 g (3.0 mol.) of dihydropyran in 1.20 liters of methylene chloride cooled to 0° C in an ice bath, is added a solution of 20 mg of para-toluenesulfonic acid in 100 ml of methylene chloride, dropwise. The reaction mixture is stirred at 0° C for one-half hour, and at ambient temperature for one hour. It is then poured into 200 ml of a 5% solution of sodium bicarbonate, the organic phase is separated, the aqueous phase extracted with 100 ml of methylene chloride, the combined organic phases washed with 100 ml of a solution of brine, dried over sodium sulfate, and evaporated under vacuum (12 mm) at 45° C to give 300 g of crude product, which is purified by fractional distillation, bp 71°–73° C (14 mm) to yield 250 g (89%) of a liguid.

EXAMPLE 57

Preparation of 3-tetrahydropyranyloxy-1-trimethylsilyl-1-propyne

To a stirred −20° C solution of 125 g (0.89 mol.) of 3-tetrahydropyranyloxy-1-propyne (Example 56) in 450 ml of ether, under a nitrogen atmosphere, is added dropwise, over one hour, a solution of 45 ml (0.89 mol.) of 2.0 N n-butyllithium in hexane. After 150 ml of dry ether is added and the mixture stirred at −20° C for 30 minutes, a solution of 98 g (0.89 mol.) of trimethylchlorosilane in 73 ml of ether is added dropwise. Stirring is continued for 30 minutes at −20° C and at ambient temperature for 18 hours. The reaction mixture is again cooled to −20° C, and a solution of 90 ml of acetic acid in 300 ml of ether is added dropwise, followed by 90 ml of water. It is then diluted with 500 ml of water, and extracted 3 times with 300 ml of 5% sodium bicarbonate solution. The organic phase is separated, washed with 500 ml of a saturated brine solution, dried over sodium sulfate, and evaporated at 40° C under vacuum (12 mm.). The curde product is fractionally distilled, bp 120°–125° C (18 mm.), to yield 120 g of an oil.

EXAMPLE 58

Preparation of d,l-erythro-3-tetrahydropyranyloxy-4-hydroxy-1-trimethylsilyl-1-octyne To a stirred −78° C solution of 62 ml (124 mmol.) of a 2.0 M solution of n-butyllithium in hexane and 50 ml of dry tetrahydrofuran, under a nitrogen atmosphere is added dropwise, a solution of 24 g (113 mmol.) of 3-tetrahydropyranyloxy-1-trimethylsilyl-1-propyne (Example 57) in 35 ml of tetrahydrofuran. This red solution is stirred one hour at −78° C, then a freshly prepared solution of zinc iodide (135 mmol.) in 125 ml of tetrahydrofuran [F. Mercier, R. Epsztein, and S. Holand, Bull. Soc. Chim. France, 2, 690 (1972)] is added dropwise at −78° C until the mixture turns yellow. After stirring an additional hour at −78° C, a solution of 21 g (250 mmol.) of n-valeraldehyde in 35 ml of tetrahydrofuran is added dropwise and the reaction mixture stirred for one hour at −78° C and 18 hours at ambient temperature. It is then cooled to 0° C and a solution of 12 ml of acetic acid in 65 ml of ether is added dropwise, followed by 75 ml of ice-water. The phases are separated and the aqueous phase is extracted twice with ether. The combined organic phases are washed 3 times with saturated sodium bicarbonate solution, until the last wash is basic, then with a saturated brine solution, dried over sodium sulfate, and evaporated to give 40 g of yellow oil. The crude product may be purified on a 4 inches × 40 inches dry column of alumina, and eluted with chloroform. I.R.: neat; 3550 (OH), 2200 (C≡C), 840, 750 [(CH$_3$)$_3$Si], cm$^{-1}$.

EXAMPLE 59

Preparation of d,l-erythro-3,4-dihydroxy-1-trimethylsilyl-1-octyne

A soolution of 19.6 g (.066 mol) of d,l-erythro-3-tetrahydropyranyloxy-4-hydroxy-1-trimethylsilyl-1-octyne (Example 58) in 55.5 ml of ethanol, 22.2 ml of acetic acid, and 22.2 ml of water is heated at reflux for 3 hours. The cooled mixture is taken to dryness and evaporated twice with benzzene. The residue is taken up in hexane, washed 3 times with saturated potassium bicarbonate solution, dried with magnesium sulfate, and evaporated-to give 17.0 of crude product. IR: neat, 3500-3400, broad (two OH)

EXAMPLE 60

Preparation of d,l-erythro-3,4-isopropylidenedioxy-1-trimethylsilyll-1-octyne

To a stirred solution of 17.0 l g (79.5 mmol.) of crude d,l-erythro-15,16-dihydroxy-1-trimethylsilyl-1-octyne (Example 59) is 33.6 ml of 2,2-dimethoxy propane at 0° C, is added 0.05 ml of 60% perchloric acid. After 30 minutes at ambient temperature, the mixture is shaken with 50 ml of hexane and 25 ml of saturated sodium bicarbonate solution. The hexane phase is separated, dried with magnesium sulfate, and evaporated to give 19.0 g of crude product.

EXAMPLE 61

Preparation of d,l-erythro-3,4-isopropylidenedioxy-1-octyne

A mixture of 19.0 g (75.0 mmol.) of crude d,l-erythro-3,4-isopropylidenedioxy-1-trimethylsilyl-1-octyne (Example 60) with 95 ml of methanol and 3.0 g of potassium carbonate is refluxed for one hour. The mixture is cooled and evaporated at 50° C (13 mm), taken up in 250 ml of benzene, and washed with 100 ml of water. The water is saturated with salt, the organic phase separated, dried with magnesium sulfate, and evaporated to give 12 g of crude product. Fractional distillation yields 7.0 g of the subject compound as a colorless oil, bp 103°–106° C (13 mm).

IR: neat; 3300 sharp (H—C≡C), 2100, (C≡C), 780 (erythro configuration) cm$^{-1}$ nmr: δ CDCl$_3$ TMS; 4.75 (dd., 1, C≡C—CH—CH, J═2Hz, J═5Hz), 4.10 (m, 1, C≡C—CH—CH—CH$_2$, 2.5 (d, 1, H—C C—CH), 1.9-1.2 (m, 14, alkyl), 0.90 (m, 3H, CH$_2$CH$_3$).

EXAMPLE 62

Preparation of d,l-erythro-1-iodo-3,4-isopropylidenedioxy-trans-1-octene

To a stirred 0° C slurry of 0.852 g (.023 mol.) of sodium borohydride and 4.21 g (.060 mol.) of 2-methyl-2-butene in 40 ml of dry tetrahydrofuran, under an argon atmosphere, is added dropwise 4.26 g (0.030 mol.) of boron trifluoride etherate complex. A solution of 2.73 g (0.015 mol.) of d,l-erythro-3,4-isopropylidenedioxy-1-octyne (Example 61) in 5 ml of tetrahydrofuran is added dropwise, the ice bath removed, and the mixture allowed to stir at ambient temperature for two hours. It is then cooled again to 0° C, and 2.88 g (0.105 mol.) of dry trimethylamine oxide is added in portions over 30 minutes. After stirring 3 hours at room temperature, this mixture is poured simultaneously with a 0° C solution of 2.13 g of iodine in 53 ml of tetrahydrofuran into 766 ml of a 0° C 15% solution of sodium hydroxide in water and the whole stirred vigorously at 0° C for 45 minutes. The organic phase is separated, the aqueous phase is extracted twice with ether, the combined organic phases are washed with a 5% solution of sodium thiosulfate, dried with magnesium sulfate, and evaporated. The crude product is chromatographed o dry column of silica gel, by eluting with chloroform, to yield 1.2 g (25%) of a yellow oil. IR: neat; 1599 sharp,

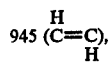

cm$^{-1}$.

EXAMPLE 63

Preparation of d,l-erythro-3-tetrahydropyranyloxy-4-acetyloxy-1-trimethylsilyl-1-octyne A solution of 3.0 g (13.2 mmol.) of d,l-erythro-3-tetrahydropyranyloxy-4-hydroxy-1-trimethylsilyl-1-octyne is heated at 100° C for 15 hours with 3 ml of acetic anhydride and 10 ml of pyridine. The mixture is evaporated to dryness, dissolved in ether, washed with sodium bicarbonate solution and water. The organic phase is dried over magnesium sulfate and evaporated to give 2.5 g of the subject compound as an oil. IR: neat; 2200 (C C), 1730 (C=O), 830, 760 [(CH$_3$)$_3$Si], cm$^{-1}$.

EXAMPLE 64

Preparation of d,l-erythro-3-hydroxy-4-acetyloxy-1-trimethylsilyl-1-octyne

In the manner of Example 59, 2.5 g (7.4 mmol.) of d,l-erythro-3-tetrahydropyranyloxy-4-acetyloxy-1-trimethylsilyl-1-octyne (Example 63) in a solution of ethanol, acetic acid, and water is heated at 100° C for 3 hoours. After workup, the crude product is chromatographed on a ⅜ inch × 22 inch dry column of silica gel, and eluted with chloroform to give 1.0 g of a yellow oil. IR: neat; 3500 (OH), 1730 (C=O), cm$^{-1}$.

EXAMPLE 65

Preparation of d,l-erythro-3-paratoluenesulfonyloxy-4-acetyloxy-1-trimethylsilyl-1-octyne To a solution of 7.5 g (41.0 mmol.) of d,l-erythro-3-hydroxy-4-acetyloxy-1-trimethylsilyl-1-octyne (Example 64) in 41 ml of dry pyridine is added 11.0 g (58 mmol.) of paratoluenesulfonyl chloride and the resulting solution is stirred at 25° C for 15 hours. The mixture is then warmed at 40° C for one hour, and after cooling, partitioned between 500 ml of diethyl ester and 100 ml of 1.0 N hydrochloric acid. The organic phase is washed three times with 100 ml of 1.0 N hydrochloric acid, once with dilute sodium bicarbonate solution, dried over magnesium sulfate, and evaporated under reduced pressure to give an oil. The crude product is purified on a 2 inches × 24 inches dry column of silica gel, and eluted with chloroform to yield a yellow oil. IR: neat; 1730 (C=O), 1595 (aromatic) cm$^{-1}$.

EXAMPLE 66

Preparation of d,l-threo-3-hydroxy-4-acetyloxy-1-trimethylsilyl-1-octyne

A mixture of 15.5 g (30.0 mmol.) of d,l-erythro-3-para-toluennesulfonyloxy-4-acetyloxy-1-trimethylsilyl-1-octyne (Example 65), 5.0 g of calcium carbonate, 25 ml of water and 250 ml of tetrahydrofuran is refluxed with stirring for 4 days. The mixture is cooled, 100 ml of water added and the organic phases separated. The aqueous phase is extracted with ether, the combined organic phases dried with magnesium sulfate, and evaporated. The crude product is chromatographed on a 3 inches × 30 inches dry column of silica gel, and eluted with chloroform to give 7.0 g of an oil. IR:: neat; 3500, (OH), cm−1.

EXAMPLE 67

Preparation of d,l-threo-3,4-dihydroxy-1-octyne

A solution of 7.0 g (28 mmol.) of d,l-threo-3-hydroxy-4-acetyloxy-1-trimethylsilyl-1-octyne (Example 66) in 50 ml of methanol is stirred at room temperature for 24 hours with a solution of 6.3 g (112 mmol.) of potassium hydroxide in 50 ml of water. The mixture is extracted twice with hexane, washed with 0.5M hydrochloric acid, brine, and dried with magnesium sulfate. After evaporation, the subject compound is obtained as a yellow oil. IR: neat, 2500 broad (2-OH), cm$^{-1}$.

EXAMPLE 68

Preparation of d,l-threo-3,4-isopropylidenedioxy-1-octyne

In the manner of Example 60, treatment of a solution of d,l-threo-3,4-dihydroxy-1-octyne (Example 67) in dimethoxypropane with 60% perchloric acid, and fractional distillation (12 mm) is productive of the subject compound as a colorless oil, containing 15% of d,l-erythro-3,4-isopropylidenedioxy-1-octyne (Example 60), as an impurity.

IR: neat; 810 (threo configuration). nmr: $\delta_{TMS}^{CDCl_3}$; 4.2 (dd, 1, —C≡C—CH—, J's - 2H$_z$, 6H$_z$), 4.1-3.9 (m, 1, —C≡C—CH—CH—CH$_2$—), 2.5 (d, 1, H—C≡C—, J = 2H$_z$), 1.9-1.2 (m, 14, alkyl), 0.90 (m, 3H, CH$_2$—CH$_3$).

EXAMPLE 69

Preparation of d,l-threo-1-iodo-3,4-isopropylidenedioxy-trans-1-octene

In the manner of Example 62, d,l-threo-3,4-isopropylidenedioxy-trans-1-octyne (Example 68) is treated successively with disiamylborane, trimethylamine oxide, iodine, and sodium hydroxide to give the subject compound.

EXAMPLE 70

Preparation of d,1-erythro-3-tetrahydropyranyloxy-4-hydroxy-1-octyne

Alkaline hydrolysis of d,1-erythro-3-tetrahydropyranyloxy-4-hydroxy-1-trimethylsilyl-1-octyne (Example 58) by the procedure of Example 61 is productive of the subject compound.

EXAMPLE 71

Preparation of d,1-erythro-3-tetrahydropyranyloxy-4-methoxy-1-octyne

To a stirred slurry of 6.0 g (150 mmol.) of a 60% oil dispersion of sodium hydride and 96 g of iodomethane, under an argon atmosphere, is added 700 ml of dry tetrahydrofuran. The stirred mixture is cooled to −20° C and a solution of 30 g (133 mmol.) of d,1-erythro-3-tetrahydropyranyloxy-4-hydroxy-1-octyne (Example 70), is added dropwise, followed by 0.1 ml of methanol. The mixture is stirred at ambient temperature for 24 hours, 10 ml of methanol is added, and evaporated. The residue is taken up in ether, washed 3 times with water, dried over magnesium sulfate, and evaporated. The crude product is purified by fractional distillation to yield 16.3 g of a colorless oil, bp 137°–140° C (12 mm).

EXAMPLE 72

Preparation of d,1-erythro-3-tetrahydropyranyloxy-4-methoxy-1-iodo-trans-1-octen In the manner of Example 62, 1.20 g (5.0 mmol.) of d,1-erythro-3-tetrahydropyranyloxy-4-methoxy-1-octyne (Example 71) is treated successively with disiamylborane, trimethylamine oxide, iodine, and sodium hydroxide. Chromatography on a 2' × 36' dry column of silica gel and elution with chloroform is productive of 0.80 g (40%) of the subject compound as an oil.

nmr δ TMS/CDCl₃; 7.9–6.1 (m, 2, HC=CH), 4.9–4.6 (2m, 2, c=C—CH, O—CH—O), 4.3–4.0 (m, 1, c=c—CH—CH—CH₂), 3.9–3.0 (m, 6, CH₂—O—CH, OCH₃), 1.8–1.2 (m, 12H, alkyl), 0.9 (m, 3, —CH₃).

EXAMPLE 73

Preparation of d,1-erythro-3-hydroxy-4-methoxy-1-iodo-trans-1-octene

A solution of 3.10 g (8.24 mmol.) of d,1-erythro-3-tetrahydropyranyloxy-4-methoxy-1-iodo-trans-1-octene (Example 72) in 60 ml of acetic acid, 30 ml of tetrahydrofuran, and 15 ml of water is stirred at ambient temperature for 18 hours. It is then evaporated at 70° C under high vacuum (1.0 mm), and three times with 40 ml of toluene to give the crude product as an oil.

EXAMPLE 74

Preparation of d,1-erythro-3-trimethylsilyloxy-4-methoxy-1-iodo-trans-1-octene

To a stirred solution of 3.0 g (10.2 mmol.) of d,1-erythro-3-hydroxy-4-methoxy-1-iodo-trans-1-octene (Example 73) in 11.0 ml of dry dimethylformamide and 1.90 g (28.0 mmol.) of imidazole cooled to 0° C is added, dropwise, 1.35 g (12.5 mmol.) of trimethylsilyl chloride. The reaction mixture is stirred a further 4 hours at room temperature. It is then poured into a mixture of 100 ml of hexane and 25 ml of water, the organic phase is separated, washed twice with water, once with a solution of saturated sodium chloride, dried over magnesium sulfate, and evaporated. The crude product is purified by fractional distillation to yield 2.0 g of a colorless oil, bp 82°–83° C (0.3 mm). IR: neat; 1602 sharp

840, 750 broad [(CH₃)₃Si—], cm⁻¹.

EXAMPLE 75

Preparation of d,1-erythro-1-iodo-3,4-dihydroxy-trans-1-octene

A solution of 1.40 g (4.50 mmol.) of d,1-erythro-1-iodo-3,4-isopropylidenedioxy-trans-1-octene (Example 62) in 30 ml of acetic acid, 10 ml of tetrahydrofuran and 10 ml of water is stirred and heated at 50° C for five hours. It is then evaporated at 40° C under high vacuum (1.0 mm), and twice more with 50 ml of benzene. Crystallization from 10 ml of chloroform at 0° C is productive of 700 mg of the white crystalline subject product.

EXAMPLE 76

Preparation of d,1-erythro-1-iodo-3,4-bis-trimethylsilyloxy-trans-1-octene

To a stirred solution of 700 mg (2.40 mmol.) of d,1-erythro-1-iodo-3,4-dihydroxy-trans-1-octene (Example 75) and 800 mg (12.0 mmol.) of imidazole, in 10 ml of dry dimethylformamide at 0° C is added dropwise 1.20 g (11.0 mmol.) of trimethylchlorosilane. The ice bath is removed, and the mixture is stirred and heated at 50° C for five hours. It is then cooled, shaken with 50 ml of hexane and 50 ml of water, the organic layer separated and washed with 15 ml of 0.5M hydrochloric acid, 15 ml of a saturated solution of sodium bicarbonate, dried with magnesium sulfate, and evaporated. This crude product is fractionally distilled, bp 90°–92° C (0.40 mm) to yield 250 mg of a colorless oil.

EXAMPLE 77

Preparation of d,1-erythro-3-trimethylsilyloxy-4-ethoxy-1-iodo-tranns-1-octene

Following the procedure of Example 71, ethylation using iodoethane of d,1-erythro-3-tetrahydropyranyloxy-4-hydroxy-1-octyne for a period of 22 hours is productive of the corresponding d,1-erythro-3-tetrahydropyranyloxy-4-ethoxy-1-octyne. This intermediate is converted to d,1-erythro-3-tetrahydropyranyloxy-4-ethoxy-1-iodo-trans-1-octene when treated successively with disiamylborane, trimethylamine oxide, iodine, and sodium hydroxide solution after the procedure of Example 72. Acid hydrolysis by the method of Example 18 to d,1-erythro-3-hydroxy-4-ethoxy-1-iodo-trans-1-octene, followed by treatment with chlortrimethylsilane and imidazole in dimethylformamide using the procedure of Example 74, and subsequent distillation, is productive of the subject compound.

EXAMPLES 78–82

By the method of Example 58 reaction of 1-trimethylsilyl-3-tetrahydropyranyloxy-1-propyne with n-butyllithium and subsequent treatment with the aldehydes listed in Table 7, below, provides the d,1-erythro-1-trimethylsilyl-3-tetrahydropyranyloxy-4-hydroxy-1-alkynes of the table.

TABLE 7

| Example | Starting Aldehyde | Product d,1-erythro-3-tetrahydropyranyloxy-4-hydroxy-1-trimethylsilyl-1-alkyne |
|---|---|---|
| 78 | n-buanal | d,1-erythro-1-trimethylsilyl-3-tetrahydropyranyloxy-4-hydroxy-1-heptyne |
| 79 | n-hexanal | d,1-erythro-1-trimethylsilyl-3-tetrahydropyranyloxy-4-hydroxy-1-nonyne |
| 80 | n-heptanal | d,1-erythro-1-trimethylsilyl-3-tetrahydropyranyloxy-4-hydroxy-1-decyne |
| 81 | 4-methyl-n-pentanal | d,1-erythro-1-trimethylsilyl-3-tetrahydropyranyloxy-7-methyl-1-octyne |
| 82 | 2-trans-n-pentenal | d,1-erythro-1-trimethylsilyl-3-tetrahydropyranyloxy-4-hydroxy-5-trans-en |

EXAMPLES 83–87

Hydrolysis of the 3-tetrahydropyranyloxy group of the d,1-erythro-1-trimethylsilyl-3-tetrahydropyranyloxy-4-hydroxy-1-alkynes listed in Table 8 below by the method described in Example 59, followed by conversion of the resulting d,1-erythro-1-trimethylsilyl-3,4-dihydroxy-1-alkyne to the corresponding d,1-erythro-1-trimethylsilyl-3,4-isopropylidenedioxy-1-alkyne by treatment with dimethoxypropane in the presence of perchloric acid by the method described in Example 60, followed by desilylation to the corresponding d,1-erythro-3,4-isopropylidenedioxyl-1-alkyne by the procedure of Example 61 followed by treatment with disiamylborane, trimethylamine oxide, iodine, and sodium hydroxide solution by the method described in Example 62 provides the product d,1-erythro-1-iodo-3,4-isopropylidenedioxy-trans-1-alkenes of Table 8, below.

TABLE 8

| Ex. | Starting d,1-erythro-1-trimethylsilyl-3-tetrahydropyranyloxy-4-hydroxy-1-alkyne of Example | Product d,1-erythro-1-iodo-3,4-isopropylidenedioxy-trans-1-alkene |
|---|---|---|
| 83 | 78 | d,1-erythro-1-iodo-3,4-isopropylidenedioxy-trans-1-heptene |
| 84 | 79 | d,1-erythro-1-iodo-3,4-isopropylidenedioxy-trans-1-nonene |
| 85 | 80 | d,1-erythro-1-iodo-3,4-isopropylidenedioxy-trans-1-decene |
| 86 | 81 | d,1-erythro-1-iodo-3,4-isopropylidenedioxy-7-methyl-trans-1-octene |
| 87 | 82 | d,1-erythro-1-iodo-3,4-isopropylidenedioxy-trans,trans-1,5-octadiene |

EXAMPLES 88-92

Acetylation of the 4-hydroxy group of the d,1erythro-1-trimethylsilyl-3-tetrahydropyranyloxy-4-hydroxy-1-alkynes listed in Table 9 below by the method described in Example 63, followed by hydrolysis of the resulting d,1-erythro-1-trimethylsilyl-3-tetrahydropyranyloxy-4-acetyloxy-1-alkynes to the corresponding d,1-erythro-1-trimethylsilyl-3-hydroxy-4-acetyloxy-1-alkynes by the method of Example 65, followed by epimerization to d,1-threo-1-trimethylsilyl-3-hydroxy-4-acetyloxy-1-alkynes by the method of Example 66 followed by hydrolysis by the method of Example 67 to give d,1-threo-3,4-dihydroxy-1-alkynes are converted to the corresponding d,1-threo-3,4-isopropylidenedioxy-1-alkynes by treatment with dimethoxypropane in the presence of perchloric acid by the method described in Example 68 followed by treatment with disiamylborane, trimethylamine oxide, iodine, and sodium hydroxide solution by the method described in Example 62 provides the product d,1-threo-3,4-isopropylidenedioxy-trans-1-alkenes of Table 9 below.

TABLE 9

| Ex. | Starting d,1-erythro-1-trimethylsilyl-3-tetrahydropyranyloxy-4-hydroxy-1-alkyne of Example | Product d,1-threo-1-iodo-3,4-isopropylidenedioxy-trans-1-alkene |
|---|---|---|
| 88 | 78 | d,1-threo-1-iodo-3,4-isopropylidenedioxy-trans-1-heptene |
| 89 | 79 | d,1-threo-1-iodo-3,4-isopropylidenedioxy-trans-1-nonene |
| 90 | 80 | d,1-threo-1-iodo-3,4-isopropylidenedioxy-trans-1-decene |
| 91 | 81 | d,1-threo-1-iodo-3,4-isopropylidenedioxy-trans-1,7-methyl-1-octene |
| 92 | 82 | d,1-threo-1-iodo-3,4-isopropylidenedioxy-trans-1,5-trans-1-octadiene |

EXAMPLE 93

Preparation of 1-octyn-4-ol

A suspension of 24.3 g (1.0 mole) of magnesium in 90 ml of dry ether is stirred at room temperature under nitrogen with 100 mg of mercuric chloride. The reaction is initiated by the addition of 2 ml of propargyl bromide and maintained by the dropwise addition of a solution of 119.5 g (1.0 mole) of propargyl bromide and 107.7 g (1.25 mole) of valenaldehyde in 300 ml of dry ether. While the initial reaction is quite vigorous and is maintained at 30° C only by cooling in an ice bath it may become necessary to heat the mixture to reflux temperature after about a third of the ether solution is added in order to maintain the reaction. After the addition is complete the reaction mixture is refluxed until most of the magnesium is dissolved (several hours) and the reaction mixture is decanted from excess magnesium into 1500 ml of stirred ice-cold ammonium chloride solution. The ether layer is separated and the aqueous layer is extracted three times with 300 ml portions of ether. The combined ether extract is washed with saturated sodium chloride solution, dried over magnesium sulfate and filtered. Evaporation of the ether under vacuum leaves about 115 g of yellow oil, which is distilled through a 15 cm Vigreaux column at 18 mm. The fraction boiling at 81°-82° C is collected (36 g) and the higher-boiling and lower-boiling distillates may be redistilled to yield additional product. The infrared absorption spectrum shows at most a trace of allene (5.1 $\mu$) and gas-liquid partition chromatography shows a purity of about 98% for the main fraction.

EXAMPLES 94-97

The product of 1-alkyn-4-ols of Table 10 below are prepared by treatment of the aldehydes listed in Table 10 with propargyl magnesium bromide by the procedure described above in Example 93.

TABLE 10

| Example | Starting Aldehyde | Product 1-alkyn-4-ol |
|---|---|---|
| 94 | n-hexaldehyde | 1-nonyn-4-ol |
| 95 | n-heptaldehyde | 1-decyn-4-ol |
| 96 | n-butyraldehyde | 1-heptyn-4-ol |
| 97 | 3-cis-hexenaldehyde* | 4-hydroxy-6-cis-ene-1-nonyne |

*M. Winter, Helv. Chim. Acta, 46, 1792 (1963).

EXAMPLE 98

Preparation of 4-triphenylmethoxy-1-octyne

A mixture of 10 g (0.08 moles) of 4-hydroxy-1-octyne [L. Crombie and A. G. Jacklin, J. Chem. Soc., 1632 (1957), also Example 93] and 30.75 g (0.09 moles) of triphenylmethyl bromide in 85 ml of dry pyridine is heated on the steam bath for 2 hours. The cooled mixture is treated with water and extracted with ether. The extract is washed successively with ice cold 2% hydrochloric acid, saturated sodium chloride solution, dried with magnesium sulfate, and taken to dryness. Column chromatography of the residue on Florisil affords an oil; $\lambda$ max 3.01, 4.72 (acetylenic hydrogen), 6.28, 9.65 and 14.25$\mu$ (triphenylmethoxy group).

EXAMPLE 99

Preparation of 4-triphenylmethoxy-1-hexyne

A stirred solution of 9.81 g (0.10 moles) of 4-hydroxy-1-hexyne and 33.5 g (0.12 moles) of triphenylmethyl chloride in 100 ml of dry pyridine is heated at reflux for 2 hours. The cooled mixture is treated with water and extracted with a hexane-ether mixture. The extract is washed successively with water and saturated sodium chloride solution, dried over magnesium sulfate, and concentrated. Column chromatography of the residue on Florisil gives an oil, max. 3290 (acetylenic hydrogen), 1600, 1030 and 705 cm-1 (triphenylmethoxy group).

EXAMPLES 100–106

The triphenylmethoxy substituted 1-alkynes listed in Table 11 below are prepared by the method of Example 98 from triphenylmethyl bromide and the corresponding hydroxy substituted 1-alkynes, appropriate literature references to which are provided in the table.

TABLE 11

| Example | Reference to Starting Hydroxy Substituted 1-Alkyne | Product Triphenylmethoxy Substituted 1-Alkyne |
|---|---|---|
| 100 | Reference 1 | 4-triphenylmethoxy-1-pentyne |
| 101 | Reference 1 (Example 96) | 4-triphenylmethoxy-1-heptyne |
| 102 | Reference 1 | 4-triphenylmethoxy-5-methyl-1-hexyne |
| 103 | Reference 2 (Example 94) | 4-triphenylmethoxy-1-nonyne |
| 104 | Reference 3 (Example 95) | 4-triphenylmethoxy-1-decyne |
| 105 | Reference 4 | 4-triphenylmethoxy-5-ethyl-1-heptyne |
| 106 | Example 97 | 4-triphenylmethoxy-6-cis-ene-1-nonyne |

References:
1 G. Fontaine, et al., Bull. Soc. Chem. France, 1447 (1963).
2 S. Abe and K. Sato, Bull. Soc. Chem. Japan, 29, 88 (1956); Chem. Abstr., 50, 13737 (1956).
3 L. Crombie and A. G. Jacklin, J. Chem. Soc., 1622 (1957);
4 Nobuharra, Akio, Chem. Abstr., 70, 3219 (1969).

EXAMPLE 107

Preparation of 1-iodo-4-triphenylmethoxy-trans-1-octene

To a stirred suspension of 1.78 g (0.074 mole) of sodium borohydriide in 200 ml of dry glyme at −5° C under nitrogen is added 15.8 g (0.22 mole) of 2-methyl-2-butene and 16.2 g (0.11 mole) of boron trifluoride etherate, and the mixture is stirred for 2 hours at −5° C to 0° C. A solution of 37.5 g (0.10 mole) of 4-trityloxy-1-octyne (Example 98) in 50 ml of glyme is added to the cold solution during 5–10 minutes, and the solution is allowed to warm to 20° C during 1.5 hours. The reaction mixture is cooled to 0° C and 30 g (0.4 mole) of dry trimethylamine-N-oxide is added during 5 minutes. On removing the cooling bath the temperature rises to 40° C and the mixture is kept between 30°–40° C for 1.5 hours. The suspension is poured rapidly into one liter of ice cold 15% sodium hydroxide solution during good stirring and a solution of 80 g of iodine in 200 ml of tetrahydrofuran is added immediately. Stirring is continued for 30 minutes without further cooling and the organic layer is separated. The aqueous layer is extracted with three 200 ml portions of ether and the combined organic layers are washed successively with water, 5% sodium thiosulfate solution and saturated sodium chloride, dried over magnesium sulfate, filtered and evaporated to yield 50 g of yellow oil. The bulk of the oil is dissolved in hexane and, after decantation from a gummy solid the hexane solution is percolated through a 5.1 cm diameter column of 1500 g of alumina with additional hexane. Fractions containing the desired product are concentrated to a pale yellow oil (33 g) which has n.m.r. and infrared spectra characteristics of the desired product.

EXAMPLES 108–115

Treatment of the triphenylmethoxy substituted 1-alkynes listed in Table 12 below disiamylborane, prepared in situ from 2-methyl-2-butene, boron, trifluoride and sodium borohydride, followed by trimethylamine N-oxide, and then sodium hydroxide and iodine - all by the procedure described in Example 107 above furnsihes the product triphenylmethoxy substituted 1-iodo-1trans-alkenes of the table.

TABLE 12

| Example | Starting Triphenylmethoxy Substituted 1-Alkyne of Example | Product 1-Iodo-triphenylmethoxysubstituted-1-traans-alkene |
|---|---|---|
| 108 | 99 | 1-iodo-4-triphenylmethoxy-1-trans-hexene |
| 109 | 100 | 1-iodo-4-triphenylmethoxy-1-trans-pentene |
| 110 | 101 | 1-iodo-4-triphenylmethoxy-1-trans-heptene |
| 111 | 102 | 1-iodo-4-triphenylmethoxy-5-methyl-1-trans-hexene |
| 112 | 103 | 1-iodo-4-triphenylmethoxy-1-trans-nonene |
| 113 | 104 | 1-iodo-4-triphenylmethoxy-1-trans-decene |
| 114 | 106 | 1-iodo-4-triphenylmethoxy-1-trans-6-cis-nonadiene |

EXAMPLES 116–124

The starting aldehydes or ketones of Table 13 below are converted to the product 1-alkyn-4-ols of the table by the procedure described in Example 93.

TABLE 13

| Example | Starting Aldehyde or Ketone | Product 1-Alkyn-4-ol |
|---|---|---|
| 115 | 2-octanone | 4-methyl-4-hydroxy-1-decyne |
| 116 | trans-2-hexenal | 4-hydroxy-5-nonen-1-yne |
| 117 | 2,2-dimethylhexanal | 5,5-dimethyl-4-hydroxy-1-nonyne |
| 118 | 2-heptanone | 4-methyl-4-hydroxy-1-nonyne |
| 119 | 2,2-dimethylpentanal | 5,5-dimethyl-4-hydroxy-1-octyne |
| 120 | 2-methylpentanal | 5-methyl-4-hydroxy-1-octyne |
| 121 | 2-methylhexanal | 5-methyl-4-hydroxy-1-nonyne |
| 122 | 2-hexanone | 4-hydroxy-4-methyl-1-octyne |
| 123 | trans-3-hexen-2-one[a] | 4-hydroxy-4-methyl-5-trans-octen-1-yne |
| 124 | trans-2-pentenal[b] | 4-hydroxy-5-trans-octen-1-yne |
| 124a | trans-2-heptenal[b] | 4-hydroxy-5-trans-decen-1-yne |

[a]G. Sturtz, Bull. Soc. Chim. Fr., 1967, 2477.
[b]R. I. Hoaglin and D. M. Hirsh, U.S. 2,628,257; Chem. Abstr., 48, 1423e (1954).

EXAMPLE 125

Preparation of 4-methyl-4-trimethylsilyloxy-1-octyne

To a stirred solution of 75.4 g (0.537 moles) of 4-hydroxy-4-methyl-1-octyne (Example 122), 104.9 g (1.54 moles) of imidazole, and 325 ml of dimethylformamide is added 65.2 g (0.60 moles) of chlorotrimethylsilane. After standing overnight the mixture is poured into 800 ml of hexane. The mixture is washed thoroughly with water followed by sodium bicarbonate solution and brine. The solution is dried over magnesium sulfate, filtered, and evaporated to give a liquid, p.m.r. spectrum, δ 1.26 (singlet, 3, $CH_3$), 1.92 (triplet, 1, HC), 2.30 (doublet, 2, $CH_2$).

EXAMPLES 126–129

The 1-alkyn-4-ols of Table 14 are converted to the product trimethylsilyl ethers of the table by treatment with chlorotrimethylsilane according to the procedure described in Example 125.

TABLE 14

| Ex. | Starting 1-Alkyn-4-ol | Product Trimethylsilyl Ether |
|---|---|---|
| 126 | 5,5-dimethyl-4-hydroxy-1-nonyne (Ex. 117) | 5,5-dimethyl-4-trimethyl-silyloxy-1-nonyne |
| 127 | 4-methyl-4-hydroxy-1-nonyne (Ex. 118) | 4-methyl-4-trimethyl-silyloxy-1-nonyne |
| 128 | 5,5-dimethyl-4-hydroxy-1-octyne (Ex. 119) | 5,5-dimethyl-4-trimethyl-silyloxy-1-octyne |
| 129 | 4-hydroxy-4-methyl-5-trans-octen-1-yne (Ex. 123) | 4-methyl-4-trimethyl-silyloxy-5-trans-octen-1-yne |
| 129a | 4-hydroxy-4-methyl-1-decyne (Ex. 124a) | 4-methyl-4-trimethyl-silyloxy-1-decyne |

EXAMPLE 130

Preparation of 1-iodo-4-hydroxy-4-methyl-trans-1-octene

To a stirred solution of 400 ml of 0.5 M bis-(3-methyl-2-butyl)borane in glyme, prepared from sodium borohydride, 2-methyl-2-butene, and boronitrifluoride etherate as in Example 107, is added 63.7 g (0.30 moles) of 4-methyl-4-trimethylsilyloxy-1-octyne (Example 125) at −10° C. The solution is stirred at ambient temperature for 2.5 hours, cooled to −10° C, and treated during 30 minutes with 158 g (2.1 moles) of solid trimethylamine oxide with cooling. The mixture is stirred at ambient temperature for 2 hours and then poured into a stirred, ice-cold solution of 15% aqueous sodium hydroxide; the stirred mixture is treated immediately with a solution of 426 g (1.68 moles) of iodine in 1100 ml of tetrahydrofuran. After 4 hours the mixture is extracted with ether. The extract is washed successively with water, aqueous sodium thiosulfate, and brine and dried over magnesium sulfate. The extract is concentrated, and the residue is subjected to chromatography on silica gel with hexane to provide an oil, p.m.r. ($CDCl_3$): δ 1.18 (singlet, 4-$CH_3$ group).

EXAMPLES 131–134

The 4-trimethylsilyloxy-1-alkynes of Table 15 are converted to the 4-hydroxy-1-iodo-trans-1-octenes of the table by the procedure described in Example 130.

TABLe 15

| Example | Starting 4-Tri-methylsilyloxy-1-octyne of Example | Product 4-Hydroxy-1-iodo-trans-1-octene |
|---|---|---|
| 131 | 126 | 1-iodo-5,5-dimethyl-4-hydroxy-trans-1-nonene |
| 132 | 127 | 1-iodo-4-methyl-4-hydroxy-trans-1-nonene |
| 133 | 128 | 1-iodo-5,5-dimethyl-4-hydroxy-trans-1-octene |
| 134 | 129 | 1-iodo-4-methyl-4-hydroxy-trans,trans-1,5-octadiene |
| 134a | 129a | 1-iodo-4-methyl-4-hydroxy-trans-1-decene |

EXAMPLE 135

Preparation of 1-iodo-4-methyl-4-trimethylsilyloxy-trans-1-octene

To a stirred mixture of 24.5 g (55.6 mmoles) of 1-iodo-4-hydroxy-4-methyl-trans-1-octene (Example 130), 13.6 g (200 mmoles) of imidazole, and 75 ml of dimethylformamide is added 10.9 g (100 mmoles) of chlorotrimethylsilane. After standing overnight the mixture is poured into 250 ml of hexane. The mixture is washed thoroughly with water followed by brine and dried over magnesium sulfate. After removal of the solvent, the product is distilled to give a colorless liquid, bp 67.5°–68° C (0.07 mm).

EXAMPLES 136–139

The 1-iodo-4-hydroxy-trans-1-alkenes of Table 16 are converted to the product trimethylsilyl ethers of the table according to the procedure described in Example 135.

TABLE 16

| Example | Starting 1-Iodo-4-hydroxy-trans-1-alkene of Example | Product Trimethylsilyl Ether |
|---|---|---|
| 136 | 131 | 1-iodo-5,5-dimethyl-4-trimethylsilyloxy-trans-1-nonene |
| 137 | 132 | 1-iodo-r-methyl-4-trimethylsilyloxy-trans-1-nonene |
| 138 | 133 | 1-iodo-5,5-dimethyl-4-trimethylsilyloxy-trans-1-octene |
| 139 | 134 | 1-iodo-4-methyl-4-trimethylsilyloxy-trans,-trans-1,5-octadiene |
| 139a | 134a | 1-iodo-4-methyl-4-trimethylsilyloxy-trans-1-decene |
| 139b | 134b | 1-iodo-4-methyl-4-trimethylsilyloxy-trans-1-decene |

EXAMPLE 140

Preparation of 4-benzoyloxy-1-octyne

To a stirred solution of 63. g (0.50 moles) of 1-octyn-4-ol (Example 93) in 500 ml of pyridine is added 77 g (0.55 moles) of benzoyl chloride. After stirring for 1.5 hours the mixture is treated with 10 ml of water, allowed to stand for 15 minutes, and concentrated. A solution of the residue in ether is washed successively with ice-cold hydrochloric acid, water, sodium bicarbonate solution, and brine. The solution is dried over magnesium sulfate, filtered through Celite, and concentrated to give an oil, λ max. 3240 (terminal acetylene) and 1730 $cm^{-1}$ (benzyloxy group).

EXAMPLE 141

Stereoselective Hydrolysis of Racemic 4-benzoyloxy-1-octyne by Rhizopus arrhizus An agar slant of R. arrhizus (MUMF 1638) is used to inoculate 7 shake flasks (250 ml Erlenmeryer). Each flask contains 50 ml of a medium consisting of 2% Edamine, 2% glucose, and 0.72% corn steep liquor in water with pH adjusted to 7.0. A total of 14 such flasks are incubated on a rotary shaker at 28° C. After 72 hours incubation, 50 mg of racemic 4-benzoyloxy-1-octyne (Example 135) in 0.1 ml of acetone is added to each flask. After 28 hours the flasks are harvested and worked up by extraction of the whole mash with an equal volume of chloroform. The combined extracts are dried over magnesium sulfate and concentrated. The resulting oil is chromatographed on a column of silica gel with hexane progressively enriched in ethyl acetate.

From fractions 3-6 is obtained 150 mg of colorless oil, identical to 4-benzoyloxy-1-octyne, $[\alpha]_D^{25} = 5 \pm 1.0°$ (C=0.91, ethyl acetate). This compound has the (S)-configuration.

From fractions 13-20 is obtained 75 mg of colorless oil, identical to 4-hydroxy-1-octyne, $[\alpha]_D^{25} = -17 \pm 1.0°$ (C=0.77, ethyl acetate). This compound has the (R)-configuration.

The strain of R. arrhizus utilized in this experiment is a higher fungus which grows steadily on a variety of artificial media at 20°-25° C. In this study of the taxonomic aspects of the culture, Petri dishes of potato-dextrose, malt extract, and cornmeal agars were inoculated and incubated at ambient room temperature for 10 days. Observations of cultural and morphological characteristics are recorded in the description below:

Colonies on Petri dishes of potato-dextrose agar growing rapidly, covering the agar surface in 3-5 days and producing a thick, loose mat of grayish mycelium. Colony surface characterized by abundant black sporangia. Colony reverse grayish white. Colonies on malt extract agar growing rapidly, covering the agar surface in 3-5 days. Mycelial mat thick, grayish-yellow. Colony surface becoming brownish-black from masses of sporangia. Colony reverse yellowish. Colonies on cornmeal agar very thin, whitish; spreading across agar surface. Cultures transparent with relatively few sporangia produced. Visibility of micromorphology is good on this medium. Rhizoids produced sparingly along stoloniferous hyphae. Generally two to three sporangiophores arose from rhizoids. Walls of sproangiophores olive brown, 14.0-20.0 μm in width at base, tapering slighly to apex; 0.5-1.5 mm in length. Sporangiophores terminated by spherical sporangia, 130-225 μm in diameter. Columellae hemispherical, 3-50 um high by 50-70 μm wide. Spores brownish when mature, 6.0-8.5 μm × 4.5-6.0 μm. Spore walls conspicuously marked by longitudinal striations.

EXAMPLE 142

Preparation of (S)-4-hydroxy-1-octyne

A solution of 1.15 g (5.0 mmoles) of (S)-4-benzoyloxy-1 -octyne (Example 141) and 1.40 g (45 mmoles) of potassium hydroxide in 50 ml of 10:1 methanol-water is allowed to stand at room temperature for 24 hours. The bulk of the methanol is evaporated at room temperature, and the mixture is extracted with ether. The extract is washed with brine, dried over magnesium sulfate, and evaporated to give a colorless oil, identical to 4-hydroxy-1-octyne $[\alpha]_D^{25} = +17 + 1.0°$ (C=0.77, ethyl acetate). This compound has the (S)-configuration.

EXAMPLES 143-148

The starting 1-alkyn-4-ols of Table 17 below are coverted to the triphenylmethoxy substituted 1-alkynes by the method of Example 98.

TABLE 17

| Example | Starting 1-Alkyn-4-ol of Example | Product Triphenyl-methoxy Substituted 1-Alkyne |
|---------|----------------------------------|------------------------------------------------|
| 143 | 116 | 4-triphenylmethoxy-5-trans-nonen-1-yne |
| 144 | 120 | 5-methyl-4-triphenyl- |

TABLE 17-continued

| Example | Starting 1-Alkyn-4-ol of Example | Product Triphenyl-methoxy Substituted 1-Alkyne |
|---------|----------------------------------|------------------------------------------------|
| | | methoxy-1-octyne |
| 145 | 121 | 5-methyl-4-triphenyl-methoxy-1-nonyne |
| 146 | 124 | 4-triphenylmethoxy-5-trans-octen-1-yne |
| 147 | 141 | (R)-4-triphenylmethoxy-1-octyne |
| 148 | 142 | (S)-4-triphenylmethoxy-1-octyne |
| 148a | 124a | 4-triphenylmethoxy-5-trans-decen-1-yne |

EXAMPLES 149-154

The product triphenylmethoxy substituted 1-iodo-1-trans-alkenes of Table 18 below are prepared from the starting triphenylmethoxy substituted 1-alkynes of the table by the procedure described in Example 107.

TABLE 18

| Ex. | Starting Triphenyl methoxy Substituted 1-Alkyn of Example | Product Triphenylmethoxy Substituted 1-Iodo-trans-1-alkene |
|-----|------------------------------------------------------------|------------------------------------------------------------|
| 149 | 143 | 1-iodo-4-triphenylmethoxy-trans,trans-1,5-nonadiene |
| 150 | 144 | 1-iodo-5-methyl-4-triphenylmethoxy-trans-1-octene |
| 151 | 145 | 1-iodo-5-methyl-4-triphenylmethoxy-trans-1-nonene |
| 152 | 146 | 1-iodo-4-triphenylmethoxy-trans,trans-1,5-octadiene |
| 153 | 147 | (R)-1-iodo-4-triphenylmethoxy-1-trans-octene |
| 154 | 148 | (S)-1-iodo-4-triphenylmethoxy-1-trans-octene |
| 154a | 148a | 1-iodo-4-triphenylmethoxy-trans,trans-1,5-decadiene |

EXAMPLE 155

Preparation of ethyl-p-fluorophenoxy-acetate

To a stirred solution of 50 g (0.29 moles) of p-fluorophenoxy acetic acid in one liter of absolute ethanol is added 10 ml of sulfuric acid. The mixture is heated to reflux for 18 hours, cooled to room temperature, and evaporated under vacuum. It is then poured onto 300 g of ice, extracted twice with 500 ml of ether, washed twice with 250 ml of a saturated solution of sodium bicarbonate, 100 ml of saturated sodium chloride solution, dried with magnesium sulfate, filtered and evaporated under vacuum giving 58 g of an oil. This is crystallized from 50 ml of hexane at −25° C to give 55 g (90%) of the subject product as colorless crystals, mp 32°-33° C.

EXAMPLE 156

Preparation of p-fluorophenoxy acetaldehyde

To a stirred solution of 1.98 g (10 mmoles) of ethyl-p-fluorophenoxy acetate (Example 155) in 15 ml of dry toluene, cooled to −78° C, under argon, is added, dropwise over 30 minutes, 8 ml of a 1.4M solution of diisobutylaluminum hydride in toluene (11 mmoles). The mixture is stirred for 2 hours at −78° C, 1 ml of methanol is added, followed by 5 ml of water, dropwise. The gel formed is filtered through Celite and washed with 100 ml of ether, portionwise. The organic phase is separated, washed twice with 25 ml of a saturated brine solution, dried with magnesium sulfate, filtered, and

47 evaporated. The oil obtained is distilled at 71°–73° C (0.1 mm) to give 600 mg (45%) of the subject product as a colorless liquid.

EXAMPLE 157

Preparation of 3-hydroxy-4-p-fluorophenoxy-1-butyne

Acetylene gas, dried by passing through a trap containing sulfuric acid, is bubbled at a moderate rate, through 5 ml of vigorously stirred tetrahydrofuran, for 15 minutes. To this acetylenic solution, is then added dropwise, with continued passage of acetylene, 3.5 ml of a 2.4M solution of n-butylmagnesium chloride in tetrahydrofuran (8.4 mmoles) over 45 minutes. The mixture is stirred a further 15 minutes, and a solution of 580 mg (3.9 mmoles) of p-fluorophenoxy acetaldehyde (Example 156) in 3 ml of tetrahydrofuran is added dropwise over 15 minutes. This solution is stirred for 2 more hours, with passage of acetylene, poured into 50 ml of a saturated solution of ammonium chloride, extracted twice with 50 ml of ether, washed with 10 ml of ammonium chloride solution, dried with magnesium sulfate, filtered, and evaporated. The crude subject product is purified by sublimation at 75° C (0.1 mm) for 5 hours to give 330 mg (48%) of white crystals, mp 46°–47° C.

EXAMPLE 158

Preparation of 4-p-fluorophenoxy-3-trimethylsilyloxy-1-butyne

To a 0° C solution of 10 g (55 mmoles) of 3-hydroxy-4-p-fluorophenoxy-1-butyne (Example 157) in 75 ml of dry dimethylformamidee and 88 g (130 mmoles) of imidazole is added dropwise, with stirring, 7.5 g (68 mmoles) of chlorotrimethylsilane. The mixture, while under an argon atmosphere, is stirred at room temperature for 18 hours, and then poured into 150 ml of hexane and 100 ml of ice-water. Thhe organic phase is separated, washed with 50 ml of a brine solution, dried with magnesium sulfate, and evaporated under vacuum. This crude product is distilled under vacuum at 0.1 mm (bp 73°–75° C), to give 12.2 g (91%) of the subject compound as a colorless oily liquid.

EXAMPLE 159

Preparation of 1-tri-n-butylstannyl-4-p-fluorophenoxy-3-trimethyl-silyloxy-trans-1-butene A mixture of 2.52 g (10 mmoles) of 3-trimethyl-silyloxy-4-p-fluorophenoxy-1-butyne (Example 158), 2.91 g (10 mmoles) of tri-n-butyl-tin hydride, and 10 mg of azobisisobutyronitrile is heated, under an argon atmosphere, with stirring, for 2 hours at 140° C. After cooling to room temperature, the crude reaction mixture is fractionally distilled at 180°–185° C (0.05 mm), to give 4.6 g (85%) of the subject product as a colorless liquid.

EXAMPLES 160–162

The product esters of Table 19 below are obtained by the procedure described in Example 155.

TABLE 19

| Example | Starting Aryloxy Acid | Product Aryloxy Ethyl Ester |
|---|---|---|
| 160 | p-chlorophenoxy-acetic acid | ethyl p-chlorophenoxy-acetate |
| 161 | 3,4-dichlorophe-noxyacetic acid | ethyl-3,4-dichlorophe-noxyacetate |

48

TABLE 19-continued

| Example | Starting Aryloxy Acid | Product Aryloxy Ethyl Ester |
|---|---|---|
| 162 | phenoxyacetic acid | ethyl phenoxyacetate |

EXAMPLE 163

Preparation of ethyl-m-trifluoromethylphenoxy-acetate

A mixture of 100 g (0.618 mole) of α,α,α-trifluoro-m-cresol, 106 g (0.632 mole) of ethyl bromoacetate, 87.5 g (0.632 mole) of potassium carbonate, and 1500 ml of acetone is stirred at reflux for 4 hours, and at room temperature for 18 hours. The mixture is filtered, evaporated under vacuum on a rotorary evaporator at 45° C and at 85° C (0.1 mm) to remove excess ethyl bromoacetate. The reaction mixture is taken up in 500 ml of ether, washed three times with 100 ml each of 0.1M potassium carbonate, once with 100 ml of water, 100 ml of 0.01M hydrochloric acid, and 100 ml of water. It is then dried with magnesium sulfate, filtered and evaporated, giving 142 g of the crude product. This is fractionally distilled at 73°–75° C (0.1 mm) to give 124 g of the purified subject product as a colorless liquid.

EXAMPLES 164–166

The product esters of Table 20 are obtained by treating the starting phenols with ethyl bromoacetate by the procedure of Example 162.

TABLE 20

| Example | Starting Phenol | Product Ester |
|---|---|---|
| 164 | p-bromophenol | ethyl p-bromophenoxy-acetate |
| 165 | 4-t-butylphenol | ethyl 4-t-butylphenoxy-acetate |
| 166 | p-methoxyphenol | ethyl p-methoxyphenoxy-acetic acid |

EXAMPLES 167–173

Following the procedure of Example 156, the starting esters of Table 21 are treated with diisobutylaluminum hydride to provide the product aldehydes of the table.

TABLE 21

| Example | Starting Ester | Product Aldehyde |
|---|---|---|
| 167 | 163 | m-trifluoromethylphenoxy acetaldehyde |
| 168 | 164 | p-bromophenoxy acetaldehyde |
| 169 | 165 | 4-t-butylphenoxy acetaldehyde |
| 170 | 166 | p-methoxyphenoxy acetaldehyde |
| 171 | 160 | p-chlorophenoxy acetaldehyde |
| 172 | 161 | 3,4-dichlorophenoxy acetaldehyde |
| 173 | 162 | phenoxyacetaldehyde |

EXAMPLES 174–180

Following the procedure of Example 156, treatment of the starting aldehyde of Table 22 with acetylene magnesium chloride provides the product alkynes of Table 22.

TABLE 22

| Example | Starting Aldehyde | Product Aryloxy Alkyne |
|---|---|---|
| 174 | 167 | 3-hydroxy-4-m-trifluoromethyl-phenoxy-1-butyne |
| 175 | 168 | 3-hydroxy-4-p-bromophenoxy-1- |

TABLE 22-continued

| Example | Starting Aldehyde | Product Aryloxy Alkyne |
|---|---|---|
| 176 | 169 | 3-hydroxy-4-t-butylphenoxy-1-butyne |
| 177 | 170 | 3-hydroxy-4-p-methoxyphenoxy-1-butyne |
| 178 | 171 | 3-hydroxy-4-p-chlorophenoxy-1-butyne |
| 179 | 172 | 3-hydroxy-4-(3,4-dichlorophenoxy)-1-butyne |
| 180 | 173 | 3-hydroxy-4-phenoxy-1-butyne |
| 180a | a | 3-hydroxy-5-phenyl-1-pentyne |
| 180b | b | 3-hydroxy-5-(p-chlorophenyl)-1-pentyne |
| 180c | c | 3-hydroxy-5-(p-methoxyphenyl)-1-pentyne |
| 180d | d | 3-hydroxy-5-(m-trifluoromethylphenyl)-1-pentyne | a hydrocinnamaldehyde[1]
b p-chlorohydrocinnamaldehyde[1]
c p-methoxyhydrocinnamaldehyde[1]
d m-trifluoromethylhydrocinnamaldehyde[2]
[1]Billman, et al., Synthetic Communications, 1, 127-131 (1971).
[2]Lednicer, Journ. Med. Chem., 11, 1258 (1968).

EXAMPLES 181–186

Treatment of the starting alkynes of Table 23 by the procedure of Example 158 followed by treatment of the procedure of Example 159 provides the product (E) 1-tri-n-butyltin-1-alkenes of the table.

TABLE 23

| Example | Starting Alkyne | Product (E)-1-tri-n-butyltin-1-alkene |
|---|---|---|
| 180 | 174 | (E)-1-tri-n-butylstannyl-3-trimethylsilyloxy-4-m-trifluoromethylphenoxy-1-butene |
| 181 | 175 | (E)-1-tri-n-butylstannyl-3-trimethylsilyloxy-4-p-bromophenoxy-1-butene |
| 182 | 176 | (E)-1-tri-n-butylstannyl-3-trimethylsilyloxy-4-t-butylphenoxy-1-butene |
| 183 | 177 | (E)-1-tri-n-burylstannyl-3-trimethylsilyloxy-4-p-methoxyphenoxy-1-butene |
| 184 | 178 | (E)-1-tri-n-butylstannyl-3-trimethylsilyloxy-4-p-chlorophenoxy-1-butene |
| 185 | 179 | (E)-1-tri-n-butylstannyl-3-trimethylsilyloxy-3,4-dichlorophenoxy-1-butene |
| 186 | 180 | (E)-1-tri-n-butylstannyl-3-trimethylsilyloxy-4-phenoxy-1-butene |
| 186a | 48 | (E)-1-tri-n-butylstannyl-4,4-trimethylene-3-trimethylsilyloxy-(Z)-6-octadiene |
| 186b | 180a | (E)-1-tri-n-butylstannyl-3-trimethylsilyloxy-5-phenyl-1-pentene |
| 186c | 180b | (E)-1-tri-n-butylstannyl-3-trimethylsilyloxy-5-(p-chlorophenyl)-1-pentene |
| 186d | 180c | (E)-1-tri-n-butylstannyl-3-trimethylsilyloxy-5-(p-methoxyphenyl)-1-pentene |
| 186e | 180d | (E)-1-tri-n-butylstannyl-3-trimethylsilyloxy-5-(m-trifluoromethylphenyl)-1-pentene |

EXAMPLE 187

Preparation of 1-chloro-1-octen-3-one

This compound is prepared according to the procedure of Price and Pappalardo [C. C. Price and J. A. Pappalardo, Org. Syn., 32, 27 (1952)] from hexanoyl chloride, acetylene, and aluminum chloride in 94% yield, bp 51°–52° C (0.1 mm); λ max 1680, 1595, 941 cm$^{-1}$.

EXAMPLE 188

Preparation of 1-iodo-1-octen-3-one

A mixture of 25 g (0.16 moles) of 1-chloro-1-octen-3-one (Example 187) and 35 g (0.23 moles) of sodium iodide in 200 ml of reagent acetone is stirred at the reflux temperature for 18 hours. The cooled mixture is filtered and the mother liquor taken to dryness. The residual oil is dissolved in benzene and the solution is washed with 5% sodium thiosulfate solution, saturated sodium chloride solution, dried and taken to dryness. The residual oil is crystallized from hexane to give 26 g of a white solid, mp 35°–37° C; λ max 1670, 950 cm$^{-1}$.

EXAMPLE 189

Preparation of 3-hydroxy-1-iodo-3-methyl-1-octene

To a Grignard solution prepared from 1.05 g (0.41 moles) of magnesium and 6.2 g (0.435 moles) of methyl iodide in 30 ml of dry ether under argon is added dropwise 10 g of 1-iodo-1-octen-3-one (Example 183) in 45 ml of ether. The resulting solution is stirred at ambient temperature for one hour. After the addition of 75 ml of saturated ammonium chloride the ether layer is separated and the aqueous layer is separated and the aqueous layer is extracted several times with ether. The coombined ether extracts are washed successively with ammonium chloride and water, dried and taken to dryness to give 9.24 g of product as an oil; λ max 2.89, 3.23, 6.24 and 10.5.

EXAMPLE 190

Preparation of 1-iodo-3-methyl-3-trimethylsilyloxy-1-octene

To a stirred solution of 11.7 g of 3-hydroxy-1-iodo-3-methyl-1octene (Example 184) and 7.4 of imidazole in 45 ml of dry dimethylformamide is added dropwise 5.98 g of trimethylsilylchloride at 0° C under argon atmosphere. After stirring at 0° C for an additional 15 minutes, the solution is stirred at ambient temperature for 18 hours. The reaction mixture is poured into 600 ml of hexane and the resulting solution washed with water, saturated sodium chloride solution, dried over anhydrous magnesium sulfate and taken to dryness to furnish 14.7 g of oil. Distillation affords 13.4 g of clear oil; bp 65° C (0.05 mm); λ max 6.21, 8.00, 9.90, 10.51, 11.90, 13.2μ.

EXAMPLE 190a

Preparation of 1-iodo-3-methyl-3-trimethylsilyloxy-1-decene

Treatment of octanoylchloride by the procedures of Example 187 followed by treatment of the resulting 1-chloro-1-decene-3-one by the procedure of Example 188 followed by treatment according to Examples 189 and 190 is productive of the named compound.

EXAMPLE 191

Preparation of 4-trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine, dried over magnesium sulfate, and concentrated. Distillation of the residue gives a colorless liquid, bp 38° C (0.2 mm).

EXAMPLE 192

Preparation of 1-iodo-4-trimethylsiloxy-trans-1-octene

To a stirred solution of 0.20 moles of freshely prepared bis-(3-methyl-2-butyl)borane in 300 ml of tetrahydrofuran at 0°-5° C is added dropwise a solution of 19.8 g of 4-trimethylsiloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°-40° C and then poured into 2 liters of 15% sodium hydroxide. The resulting mixture is treated immediately with a solution of 140 g of iodine in 300 ml of tetrahydrofuran. After 0.5 hour the organic phase is-separated and the aqueous phase is extracted with ether. The combined organic layers are washed with water, sodium thiosulfate solution, and brine; dried over magnesium sulfate; and concentrated to give an oil, pmr spectrum (CDDl$_3$): 6.2 (d, ICH=) and 6.7 (quintuplet, =CH—).

EXAMPLE 193

Preparation of 4-hydroxy-1-iodo-trans-1-octene

A 23 g portion of 1-iodo-4-trimethylsilyloxy-1-octene is dissolved in a mixture of 200 ml of glacial acetic acid, 100 ml of tetrahydrofuran, and 50 ml of water. Concentration provides the named product.

EXAMPLE 194

Preparation of 4-trimethylsiloxy-4-vinyl-1-iodo-trans-1-octene

To a stirred solution of 456 mg of 4-hydroxy-4-vinyl-1-iodo-trans-1-octene and 320 mg of imidazole in 1.0 ml of dimethylformamide is added 0.23 ml of chlorotrimethylsilane during 3 minutes. The mixture is stirred at room temperature for 22 hours and partitioned with a mixture of cold hexane and water. The hexane layer is washed repeatedly with water and then brine, dried over magnesium sulfate, and concentrated to give an oil, pmr spectrum (CDCl$_3$): 0.13 (s, trimethylsiloxy group) and 2.32 (d, =CHCH$_2$).

EXAMPLE 195

Preparation of n-butyl cyclopropyl ketone

To a vigorously-stirred solution of 31.0 g of cyclopropanecarboxylic acid in 330 ml of ether is added a solution of n-butyllithium (748 mmoles) in about 750 ml of 2:1 ether-hexane during one hour at 5°-10° C. The resulting suspension is diluted with 300 ml of ether and stirred at room temperature for 2 hours and at reflux for 2 hours. The mixture is cooled and poured into several portions of 1:1 ice:4N hydrochloric acid. The ethereal phases are combined and washed with brine, sodium carbonate solution, and brine. The extract is dried over magnesium sulfate and concentrated. The residue is distilled to provide a liquid, bp-102°-104° C (80 mm), pmr spectrum (CDCl$_3$): β 2.55 (triplet, —CH$_2$CO—).

EXAMPLE 196

Preparation of 4-cyclopropyl-4-hydroxy-1-octyne

To a stirred, refluxing suspension of amalgum prepared from 6.2 g of magnesium and 50 mg of mercuric chloride suspended in 60 ml of ether is added a solution of a mixture of 30.4 g of n-butyl cyclopropyl ketone (Example 189) and 29.8 g of propargyl bromide in 65 ml of ether during 60 minutes. After reaction at reflux temperature for an additional 30 minutes, the mixture is cooled to 0° C and treated with 35 ml of saturated ammonium chloride. The mixture is diluted with ether and filtered through Celite. The filtrate is washed with brine, dried over potassium carbonate, and concentrated. The resiidue is distilled to provide a liquid, β 0.43 (cyclopropyl hydrogens), 2.07 (triplet, HC≡C), and 2.44 (doublet, C≡CCH$_2$).

EXAMPLE 197

Preparation of 4-cyclopropyl-4-trimethylsiloxy-1-octyne

To a stirred solution of 27.8 g of 4cyclopropyl-4-hydroxy-1-octyne (Example 190) and 33.3 g of imidazole in 130 ml of dimethylformamide at 5° C is added 24 ml of chlorotrimethylsilane during 5 minutes. The solution is stirred at ambient temperature for 17 hours and then partitioned with 600 ml of hexane and 250 ml of ice water. The hexane phase is separated and washed successively with water and brine. The solution is dried over magnesium sulfate and evaporated to give a liquid, pmr spectrum (CDCl$_3$): δ 0.12 (singlet, trimethylsiloxy group), 2.02 (triplet, HC≡C), and 2.45 (doublet, C≡CH$_2$).

EXAMPLE 198

Preparation of 4-cyclopropyl-4-trimethylsiloxy-1-(tri-n-butylstannyl)-trans-1-octene A stirred mixture of 23.8 g of 4-cyclopropyl-4-trimethylsiloxy-1-octyne (Example 191), 28 ml of tri-n-butyltin hydride, and 50 mg of azobisisobutyronitrile under nitrogen is ehated to 85° C. After the resulting exothermic reaction subsides the mixture is heated at 130° C for one hour. The crude product is evaporatively distilled to give a liquid, pmr spectrum (CDCl$_3$): δ 0.10 (trimethylsiloxy group), 2.33 (doublet, =CHCH$_2$), and 6.02 (vinyl hydrogens).

EXAMPLES 199–204

Treatment of the starting carboxylic acids of Table 24 with the appropriate alkyllithium by the method of Example 190 provides the product ketones of the table.

TABLE 24

| Example | Starting Carboxylic Acid | Alkyl Lithium | Product Ketone |
|---|---|---|---|
| 199 | cyclopropane carboxylic acid | n-hexyllithium | n-hexylcyclopropyl ketone |
| 200 | cyclopropane carboxylic acid | n-propyllithium | n-propylcyclopropyl ketone |
| 201 | acrylic acid | n-hexyllithium | n-hexylvinyl ketone |
| 202 | acrylic acid | n-propyllithium | n-propylvinyl ketone |
| 203 | crotonic acid | n-butyllithium | n-butyl-1-propenyl |

TABLE 24-continued

| Example | Starting Carboxylic Acid | Alkyl Lithium | Product Ketone |
|---|---|---|---|
| 204 | crotonic acid | n-hexyllithium | ketone n-hexyl-1-propenyl ketone |

EXAMPLES 205–210

Treatment of the starting ketones of Table 25 with propargymagnesium bromide by the procedure of Example 190 followed by treatment with chlorotrimethylsilane by the procedure of Example 191 followed by treatment with tri-n-butyltin hydride by the method of Example 192 is productive of the vinylstannyl derivatives of the table.

TABLE 25

| Example | Starting Ketone | Product Vinylstannyl Derivative |
|---|---|---|
| 205 | 193 | (E)4-trimethylsilyloxy-4-cyclopropyl-1-tri-n-butylstannyldecene |
| 206 | 194 | (E)4-trimethylsilyloxy-4-cyclopropyl-1-tri-n-butylstannylheptene |
| 207 | 195 | (E)4-trimethylsilyloxy-4-vinyl-1-tri-n-butylstannyldecene |
| 208 | 196 | (E)4-trimethylsilyloxy-4-vinyl-1-tri-n-butylstannylheptene |
| 209 | 197 | (E)4-trimethylsilyloxy-4-(1-propenyl)-1-tri-n-butylstannyloctene |
| 210 | 198 | (E)4-trimethylsilyloxy-4-(1-propenyl)-1-tri-n-butylstannyldecene |

EXAMPLE 211

Preparation of 1-propargyl-1-hydroxycyclohexane

A stirred suspension of 121.6 g (5.0 mol) of magnesium in 1-l. of anhydrous ether is treated with 0.6 g of mercuric chloride and about 100 mg of iodine. After several minutes, 3 ml of propargyl bromide is added and if no exotherm is noted, a small amount of reacting propargyl bromide and magnesium in ether is added. When the reaction begins, a mixture of 5.0 mol of cyclohexanone and 595 g (5.0 mol) of propargyl bromide is added dropwise at a rate that produces vigorous refluxing of the solution. (The propargyl bromide must always be present in some excess otherwise the reaction will stop. If this happens, the addition of about 1 ml of propargyl bromide will restart the reaction.) After about half of the propargyl bromide-cyclohexanone mixture has been added, another 500-750 ml of ether is used to dilute the reaction mixture. At the end of the addition, the reaction mixture is refluxed for at least 0.5 hour, cooled and poured into 4 liters of saturated ammonium chloride during good stirring. The ethereal layer is separated and the aqueous layer is washed with ether several times and the combined extract is washed twice with saturated sodium chloride solution and dried over anhydrous magnesium sulfate. Evaporation of the ether yields 583 g (630 g theory) of a dark oil which is distilled giving purified 1-propargyl-1-hydroxycyclohexane.

EXAMPLE 212

Preparation of 1-Ethynyl-1-trimethylsilyloxycyclohexane

A 194 g portion of imidazole and 158.2 g of 1-ethynylcyclohexane-1-ol are mixed with 500 g of dimethylformamide with cooling in an ice bath. A 152 g portion of trimethylchlorosilane is added with cooling and stirring in about one minute. The mixture is stirred for one hour and allowed to stand overnight. One liter of hexane is added. The lower layer is separated, diluted with water and extracted with hexane. The hexane layers are washed several times with water and then combined and dried over magnesium sulfate. Filtration and then evaporation of the hexane gives 198.5 g of product which is distilled giving 168 g of the desired product.

EXAMPLE 213

Preparation of 1-Propargyl-1-trimethylsilyloxycyclohexane

To a stirred solution of 55.4 g of 1-(2-propyn-1-yl)cyclohexanol [H. Gutmann, et. al., Helv. Chim. Acta, 42, 719 (1959)] and 79 g of imidazole in 240 ml of DMF at 10° C initially is added 56 ml of chlorodimethylsilane during 10 minutes. The cloudy yellow solution is stirred at room temperature for 26 hours. The resulting mixture is partitioned between 1000 ml of hexane and 400 ml of water at 0°-5° C. The hexane phase is washed successively with 6 × 200 ml of cold water and 200 ml of brine. The extract is dried over magnesium sulfate, filtered, and evaporated to give 85 g of colorless liquid, i.r. (film):1240 and 830 cm$^{-1}$ (trimethylsilyloxy group).

EXAMPLE 214

Preparation of IR,2S(and 1S,2R)-1-Ethynyl-1-hydroxy-2-butylcyclopentane and IR,2R(and 1S,2S)-1-ethynyl-1-hydroxy-2-butylcyclopentane Into 150 ml of tetrahydrofuran is bubbled purified acetylene, as a solution of 2.4M n-butyl magnesium chloride (92 ml) is added dropwise with stirring over a 2 hour period. To the resulting solution of acetylene magnesium chloride is added 21 g of 2-butylcyclopentanone in 50 ml of tetrahydrofuran dropwise over 15 minutes. The solution is stirred for 30 minutes and then is poured into an ice cold solution of saturated ammonium chloride. The mixture is acidified to pH 5 and extracted with ether. The ether solution is washed with brine and dried over magnesium chloride. The ether is removed and the residue is distilled giving 14.8 g of a colorless liquid. This is chromatographed on a dry column of silica-gel eluting with benzene-ethyl acetate (19:1) to separate isomers giving IR,2S(and 1S,2R)-1-ethynyl-1-hydroxy-2-butylcyclopentane and 1R,2R(and 1S,2S)-1-ethynyl-1-hydroxy-2-butylcyclopentane.

EXAMPLE 215

Preparation of 1R,2S(and 1S,2R)-1-Ethynyl-1-trimethylsilyloxy-2-butylcyclopentane To a solution of 29.4 g of 1R,2S(and 1S,2R)-1-ethynyl-1-hydroxy-2-butylcyclopentane and 30.2 g of imidazole in 180 ml of dimethylformamide is added at 0° C with stirring 24.1 g of trimethylsilychloride. The mixture is stirred for 3 hours. The mixture is poured into 700 ml of hexane and washed twice with water and once with brine. The ether solution is dried over magnesium sulfate. The solvent is removed and the residue is distilled (bp 64°-72° C, 0.6 mm) to give 35.8 g of 1R,2S(and 1S,2R)-1-ethynyl-1-trimethylsilyloxy-2-butylcyclopentane.

EXAMPLE 216

Preparation of 1R,2S(and 1S,2R)-1-trans-2-Iodovinyl)-1-trimethylsilyloxy-2-butylcyclopentane To a mixture of 9.2 g of sodium borohydride and 45.8 g of 2-methyl-2-butene in 350 ml of dry tetrahydrofuran at 0° C with stirring under nitrogen is added, over 20 minutes, 41.1 ml of boron trifluoride etherate. After 3 hours, to this resulting solution of diisoamylborane is added 38.8 g of 1R,2S(and 1S,2R)-1-ethynyl-1-trimethylsilyloxy-2-butylcyclopentane in 40 ml of tetrahydrofuran in 20 minutes. The mixture is ttirred 2 hours and then stored at −20° C overnight. The mixture is allowed to warm to 0° C and at 0° C 85 g of dry trimethylamineoxide is added portionwise over 20 minutes. After stirring at 25° C for one hour, the mixture is filtered through diatomaceous earth. The filtrate is poured simultaneously with a solution of 230 g of iodine in 250 ml of tetrahydrofuran into a stirred, cold solution of 430 g of sodium hydroxide in 1900 ml of water. After stirring for 30 minutes, the organic layer is separated. The aqueous layer is extracted with ether. The combined organic solutions are washed twice with a saturated solution of sodium thiosulfate and once with brine. The solution is dried over magnesium sulfate, the solvent is removed and the residue is dissolved in hexane. The hexane solution is filtered through diatomaceous earth and silica gel. The hexane is removed and the residue is purified by dry column chromatography on silica gel eluting with hexane: 45.35 g of 1R,2S(and 1S,2R)-1-(trans-2-iodovinyl)-1-trimethylsilyloxy-2-butylcyclopentane is obtained.

EXAMPLES 217–218

In the manner of Example 216 described above, the following acetylenic alcohols listed in Table 26 were prepared from the acetylenic Grignard reagent and the ketone specified.

TABLE 26

| Example | Grignard Reagent | Ketone | Acetylenic Alcohol |
|---|---|---|---|
| 217 | acetylene magnesium chloride Method A | cyclohexanone | 1-ethylnyl-1-hydroxy-cyclohexane |
| 218 | acetylene magnesium chloride Method A | cyclopentanone | 1-ethynyl-1-hydroxy-cyclopentane |

EXAMPLE 219

Preparation of 1-(3-Tri-n-butylstannyl-2-trans-propenyl)-1-trimethylsilyloxycyclohexane To a stirred mixture of 31.5 g of 1-propargyl-1-trimethylsilyloxycyclohexane and 150 mg of azobisisobutyronitrile is added 41 ml of tri-n-butyltin hydride. The stirred mixture is heated to about 80° C. The initial exothermic reaction is moderated, and the temperature is subsequently maintained at 130°-135° C for one hour.

The product is distilled to afford 56 g of colorless liquid, bp 150°-160° C (0.15–0.3 mm), pmr (CDCl$_3$): 6.0 (multiplet, vinyl protons).

EXAMPLES 220–221

Using the procedure outlined above for Example 213, the acetylenic alcohols listed in Table 27 are converted to their corresponding acetylenic trimethylsilyloxy derivatives; these in turn using the procedure outlined above for Example 216, were converted to their corresponding trans-2-iodovinyl derivatives.

TABLE 27

| Example | Acetylene of Example | Vinyl Iodide Compound |
|---|---|---|
| 220 | 217 | 1-(trans-2-iodovinyl)-1-trimethylsilyloxy-cyclohexane |
| 221 | 218 | 1-trans-2-iodovinyl)-1-trimethylsilyloxy-cyclopentane |

EXAMPLE 222

Preparation of 1-(3-Tri-n-butylstannyl)-2-trans-propenyl)-1-trimethylsilyloxycyclopentane Treatment of cyclopentanone by the sequential reactions described by Examples 211, 213 and 219 is productive of the title compound.

EXAMPLE 223

Methyl Nat. 15α-hydroxy-9-oxo-11α/β(2-hydroxyethylthio)-5-cis,13-trans-prostadienoate A solution of 2 g of nat. PGA$_2$ methyl ester (U.S. Pat. No. 3,759,965) and 448 mg of 2-mercaptoethanol is stirred under argon. One drop of triethylamine is added and the reaction mixture is stirred for 4 hours and 15 minutes. A 180 mg portion of the reaction mixture is chromatographed on a one mm silica gel preparative plate, eluting with ethyl acetate:benzene (2:3). A 2,4-dinitrophenylhydrazone positive band ¼ to 1¼ inches above the origin is removed and the product is eluted with 20% methanol in chloroform. This eluate is evaporated giving 97 mg of the product (A) as a pale yellow oil.

The remainder of the reaction mixture is chromatographed similarly on four silica gel preparative plates 2 mm thick. The product (B) is isolated as above and combined with (A) giving 1.55 g of the desired product as a yellow oil.

EXAMPLE 224

11α/β-(2-hydroxy ethylthio)-15-hydroxy-15-methyl-9-oxo-5-cis,13-trans-prostadienoic acid A mixture of 200 mg of all racemic 15 methyl PGA$_2$ (U.S. Pat. No. 3,919,286), 57 mg of mercaptoethanol and 60 mg of triethylamine is stirred under argon. One additional drop of triethylamine is added and the mixture is stirred for 2 hours. The mixture is acidified with 5% HCl, extracted with ether, the ether is washed with a saturated solution of sodium chloride and then dried over sodium sulfate. The residue is chromatographed on two 1 mm thick silica gel plates, eluting twice with ethyl acetate:benzene (1:4) containing 1.5% acetic acid. The yellow 2,4-dinitrophenylhydrazone positive band between ¼ and 1¼ inches above the origin is removed from the silica with 20% methanol in chloroform, giving 143 mg of the desired product as an amber oil.

EXAMPLE 225

11α/β-(2-hydroxy ethylthio)-16-hydroxy-16-methyl-9-oxo-5-cis,13-trans-prostadienoic acid A solution of 4.2 g of E-1-iodo-4-methyl-4-trimethylsilyloxy-1-octene in 100 ml of dry ether is cooled in a dry ice-acetone bath under nitrogen and treated with 30.85 ml of t-butyl lithium via a syringe, over a period of 15 minutes. In a second flask a mixture of 1.61 g of copper pentyne and 5.4 ml of hexamethylphosphoramide in 70 ml of ether is stirred for 15 minutes until it becomes clear. This copper pentyne solution is added to the vinyl lithium solution via a syringe, over a period of 20 minutes. The mixture is stirred in the same bath for 1.5 hours and then a solution of 4.7 g of bis-THP-cyclopentenone in 70 ml of ether is added at −78° C. After stirring at −78° C for 40 minutes, the cooling bath is replaced by an ice-acetone bath. Stirring is continued at −20° C to −10° C for 40 minutes. The reaction is quenched by the addition of 50 ml of cold, saturated aqueous ammonium chloride solution and the entire mixture is poured into 450 ml of cold, saturated aqueous ammonium chloride solution. The mixture is allowed to stand overnight in a refrigerator. The aqueous phase is separated and extracted twice with ether. The ether extracts are combined with the organic phase and washed with dilute aqueous HCl, water and finally brine. After evaporation of the solvents, the residue is dissolved in a mixture of 80 ml of acetic acid, 60 ml of tetrahydrofuran and 20 ml of water and stirred at room temperature for one hour. The mixture is poured into water and extracted with ether. The ether extract is washed with brine and the solvents are evaporated on a rotary evaporator in the presence of toluene. The residue is passed through a 250 g silica gel column packed in 10% ethyl acetate in hexane. Continuous elution with increasing percentage of ethyl acetate in hexane gives 2.33 g of product.

A 2.3 g portion of this product is dissolved in a mixture of 100 ml of acetic acid, 50 ml of tetrahydrofuran and 25 ml of water. The mixture is stirred and heated at 45°-50° C for 3.5 hours. The mixture is worked up by repeating the above ether extraction and water and brine washing. The solvent is evaporated in the presence of toluene as above. The residue is passed through a 50 g silica gel column packed in 30% ethyl acetate in hexane. Continuous elution with increasing percentage of ethyl acetate in hexane give 1.09 g of product.

A solution of 157 mg of the above compound in 85 ml of tetrahydrofuran and 5 ml of 1.5N HCl is stirred under a nitrogen atmosphere at room temperature for 48 hours. The reaction mixture is diluted with brine and extracted with 80 ml of ether in two portions. The combined ether extracts are washed with brine, dried over magnesium sulfate, filtered and concentrated in vacuo to a yellow oil. This oil is chromatographed using a 2000μ preparative thin layer plate, eluting with ethyl acetate:benzene (2:3) containing 2% acetic acid. The product is located and then eluted from the silica gel with 20% methanol in chloroform giving 122 mg of yellow oil.

To a stirred solution of the 122 mg of the previous compound, 56 mg of β-mercaptoethanol and one ml of tetrahydrofuran, at room temperature, is added 14 drops of triethylamine. The reaction mixture is stirred for 3 hours and then chromatographed using one 1 mm preparative thin layer silica gel plate, eluting with ethyl acetate:benzene (2:3) containing 2% acetic acid. The product is located and eluted from the silica gel with 20% methanol in chloroform giving 52 mg of the desired product as a yellow oil.

EXAMPLE 226

11α/β(2-hydroxyethylthio)-16-hydroxy-9-oxo-13-trans-prostenoic acid

To a stirred solution of 8.57 g of (E)-1-tributylstannyl-4-triethylsilyloxy-1-octene and 10 ml of anhydrous tetrahydrofuran, cooled to −70° C under an argon atmosphere, is slowly added 7.0 ml of n-butyl lithium. After 15 minutes the reaction mixture is warmed to −40° C for 2 hours. The reaction mixture is recooled to −78° C. A solution of 2.2 g of copper pentyne and 6.85 g of tri-n-butyl phosphine in 27 ml of ether is added. After 2 hours a 4.60 g portion of cyclopentenone and 15 ml of anhydrous ether is added. After 30 minutes, the reaction mixture is warmed to −35° C to −40° C for one hour and then at 30° C to 35° C for 30 minutes. The reaction mixture is cooled to −40° C and to it is slowly added 5 ml of acetic acid. The reaction mixture is poured into a mixture of 400 ml of saturated aqueous ammonium chloride and 250 ml of ether and is vigorously stirred for one hour. The aqueous phase is separated and extracted with 400 ml of ether in three portions. The ether phases are combined, washed with 1% H$_2$SO$_4$, dried over magnesium sulfate, filtered and concentrated in vacuo giving 22.7 g of amber liquid.

A solution of 22.7 g of the above liquid in 250 ml of a mixture of acetic acid:tetrahydrofuran:water (4:2:1) is stirred under an argon atmosphere at room temperature for one hour. The reaction mixture is diluted with toluene and concentrated in vacuo giving 19.7 g of brown liquid.

This 19.7 g of liquid is dry column chromatographed using 1500 g of silica gel and eluted with ethyl acetate:benzene (2:3) containing 2% acetic acid. A total of 900 ml is collected. The column is cut into one inch segments. Like fractions are combined after thin layer chromatographic analysis. The product is eluted from the silica with 20% methanol in chloroform giving 1.6 g. An additional 326 mg was obtained upon further chromatographing impure fractions.

A solution of 325 mg of the oil in 13 ml of tetrahydrofuran and 10 ml of 1.5N HCl is stirred under nitrogen, at room temperature for 48 hours. The reaction mixture is diluted with brine and extracted with 125 ml of ether in two portions. The combined ether extracts are washed with brine, dried over magnesium sulfate, filtered and concentrated in vacuo giving a yellow oil.

This yellow oil is chromatographed using two 2000μ preparative thin layer plates and eluting with ethyl acetate:benzene (2:3) containing 2% acetic acid. The product is located and eluted from the silica gel with 20% methanol in chloroform giving 189 mg of a yellow oil.

To a stirred solution of the 189 mg of oil, 60 mg of β-mercaptoethanol and one ml of tetrahydrofuran at room temperature is added 17 drops of triethylamine. The reaction mixture is stirred for 3 hours and then chromatographed using one 1 mm preparative thin layer silica gel plate and eluting with ethyl acetate:benzene (2:3) containing 2% acetic acid. The product is located and eluted from the silica gel with 20% methanol in chloroform giving 111 mg of the desired final product as a yellow oil.

EXAMPLE 227

Erythro-11α/β-(2-hydroxyethylthio)-15α,16-dihydroxy-9-oxo-5-cis,13-trans-prostadienoic acid A 3.10 g portion of erythro(E)-1-iodo-3,4-isopropylidenedioxy-1-octene is reacted with 29 ml of 0.8N-t-butyllithium in hexane with 60 ml of ether for 2 hours. A solution in ether at −78° C of 10 mmol of lithium thiophenoxide with 3.95 g (10.0 mmol) of tri-n-butylphosphine copper iodide is next added for one hour, then is added 3.44 g of bis-THP cyclopentenone at −20° C for 1½ hours. The reaction mixture is quenched and worked up with ammonium chloride. This crude product is partially deblocked with 125 ml of acetic acid:tetrahydrofuran:water (5:5:2) at room temperature for 2 hours. After removal of the solvents by azeotroping 3 times with toluene at 50° C, the crude product is chromatographed on a dry column of silica gel with 2:3 ethylacetate in benzene with 2% of acetic acid. The column is cut into 1½ inch segments and like fractions are combined giving 2.10 g of product.

A solution of 400 mg of the above PG acetonide in 15 ml of acetic acid:tetrahydrofuran:water (4:2:1) is stirred at 50° C under an argon atmosphere for 3 hours. The reaction mixture is cooled, diluted with toluene and concentrated in vacuo giving a yellow oil.

This oil is stirred in a mixture of 15 ml of tetrahydrofuran and 12 ml of 1.5N HCl under an argon atmosphere at room temperature for 48 hours. The reaction mixture is diluted with brine and extracted with 120 ml of ether in two portions. The combined ether extracts are washed with brine, dried over magnesium sulfate, filtered and concentrated in vacuo giving a yellow oil. This oil is chromatographed using two 2000μ preparative thin layer silica gel plates, eluting with ethyl acetate:benzene (2:3) containing 2% acetic acid. The product is located and eluted from the silica gel with 20% methanol in chloroform giving 88 mg.

To a stirred solution of the above 88 mg of product, one ml of tetrahydrofuran and 126 ml of β-mercaptoethanol at room temperature, is added 8 drops of triethylamine. The reaction mixture is stirred for 3 hours and then chromatographed using one 2 mm preparative thin layer plate and eluting twice with ethyl acetate:benzene (2:3) containing 2% acetic acid. The product is located and eluted from the silica gel with 20% methanol in chloroform. The eluent is concentrated in vacuo giving the desired product as a yellow oil.

EXAMPLE 228

Nat. 11α/β-(2-hydroxyethylthio)-15α-hydroxy-9-oxo-13-transprostenoic acid

To a mixture of 100 mg of nat. PGA$_1$ (U.S. Pat. No. 3,725,469) and 33 mg of triethylamine is added 24 mg of 2-mercaptoethanol. The reaction mixture is stirred under an argon atmosphere for 18 hours. Ether is added. An equal volume of 5% HCl is added giving complete two-phase solution. The ether is separated, washed three times with saturated sodium chloride solution, dried over sodium sulfate and taken to dryness giving a pale yellow oil comprising 123 mg of the desired product.

Column chromatography as described in Example 229 will provide the separated 11α and 11β epimers.

EXAMPLE 229

Methyl Nat.-11α(2-hydroxyethylthio)-15α-hydroxy-9-oxo-5-cis,13-trans-prostadienoate and methyl nat.-11β(2-hydroxyethylthio)-15α-hydroxy-9-oxo-5-cis,13-trans prostadienoate A solution of 10 g (28.7 mmol) of nat.-PGA$_2$ methyl ester, 2.24 g (28.7 mmol) of 2-mercaptoethanol and 5 drops of triethylamine is stirred at ambient temperature under an argon atmosphere for 18 hours. The resulting oil is chromatographed on a 61 inch by 3 inch (flat) nylon tube packed with 1700 g of silica-gel. The column is developed with ethylacetate-benzene-acetic acid (20:30:1), and 2000 ml of eluant is collected. The column is then divided into 1-inch segments. Segments 12–17 are combined to furnish 2.64 g of nat.-11α-(2-hydroxyethylthio)-PGE$_2$ methyl ester; R$_f$ 0.33 (ethylacetate-benzene-acetic acid/20:30:1, 3 elutions). Segments 18–23 are combined to give 2.83 g of a mixture of nat.-11α- and 11β-(2-hydroxyethylthio)-PGE$_2$ methyl ester; R$_f$ 0.33, 0.26 (ethyl acetate-benzene-acetic acid/20:30:1, 3 elutions). Segments 24–36 are combined to give 2.46 g of nat.-11β-(2-hydroxyethylthio)-PGE$_2$ methyl ester; R$_f$ 0.26 (ethylacetate-benzene-acetic acid/20:30:1, 3 elutions).

EXAMPLES 230–262

Addition of 2-mercaptoethanol to the A-prostaglandins of Table 28 by the method of Example 229 followed by silica-gel chromatography is productive of the separated 11α and 11β(2-hydroxyethylthio) prostanoic analogs.

TABLE 28

| Example | | |
|---|---|---|
| 230 | nat.-prostaglandin A$_1$ | nat.-11α-(2-hydroxyethylthio)-15α-hydroxy-9-oxo-13-trans-prostenoic acid and the corresponding 11β-isomer |
| 231 | prostaglandin A$_1$ | 11α-(2-hydroxyethylthio)-15α-hydroxy-9-oxo-13-trans-prostenoic acid and the corresponding 11β-isomer |
| 232 | nat.-prostaglandin A$_2$ | nat.-11α-(2-hydroxyethylthio)-15α-hydroxy-9-oxo-5-cis, 13-trans-prostadienoic acid and the corresponding 11β- |

TABLE 28-continued

| Example | | |
|---|---|---|
| | | isomer |
| 233 | prostaglandin $A_2$ | 11α-(2-hydroxyethylthio)-15α-hydroxy-9-oxo-5-cis,13-trans-prostadienoic acid and the corresponding 11β-isomer |
| 234 | 15-deoxy-16-hydroxy prostaglandin $A_1$ ethyl ester (U.S. Pat. No. 3,950,406) | Ethyl 11α-(2-hydroxyethylthio)-16-hydroxy-9-oxo-13-trans-prostenoate and the corresponding 11β-isomer |
| 235 | 15-deoxy-16-hydroxy prostaglandin $A_1$ methyl ester (U.S. Pat. No. 3,950,406) | Methyl 11α-(2-hydroxyethylthio)-16-hydroxy-9-oxo-13-trans-prostenoate and the corresponding 11β-isomer |
| 236 | 15-deoxy-16-hydroxy-17-methyl-19,20-dinor prostaglandin $A_1$ (U.S. Pat. No. 3,950,406) | 11α-(2-hydroxyethylthio)-16-hydroxy-9-oxo-17-methyl-19,20-dinor-13-trans-prostenoic acid and the corresponding 11β-isomer |
| 237 | 15-deoxy-16-hydroxy-17-ethyl-20-nor prostaglandin $A_1$ (U.S. Pat. No. 3,950,406) | 11α-(2-hydroxyethylthio)-16-hydroxy-9-oxo-17-ethyl-20-nor-13-trans-prostenoic acid and the corresponding 11β-isomer |
| 238 | nat.-15-deoxy-16(R)-hydroxy prostaglandin $A_1$ methyl ester (U.S. Pat. No. 3,950,406) | nat.-11α-(2-hydroxyethylthio)-16(R)hydroxy-9-oxo-13-trans-prostenoic acid methyl ester and the corresponding 11β-isomer |
| 239 | nat.-15-deoxy-16(S)-hydroxy prostaglandin $A_1$ methyl ester (U.S. Pat. No. 3,950,406) | nat.-11α-(2-hydroxyethylthio)-16(S)-hydroxy-9-oxo-13-trans-prostenoic acid methyl ester and the corresponding 11β-isomer |
| 240 | 15-deoxy-16-hydroxy-17-methyl-prostaglandin $A_1$ Example 273 | 11α-(2-hydroxyethylthio)-16-hydroxy-9-oxo-17-methyl-13-trans-prostenoic acid and the corresponding 11β-isomer |
| 241 | 15-deoxy-16-hydroxy-17-methyl prostaglandin $A_1$ ethyl ester (Example 274) | ethyl 11α-(2-hydroxyethylthio)-16-hydroxy-9-oxo-17-methyl-13-trans-prostenoate acid and the corresponding 11β-isomer |
| 242 | 15-deoxy-16-hydroxy prostaglandin $A_1$ (Example 275) | 11α-(2-hydroxyethylthio)-16-hydroxy-9-oxo-13-trans-prostenoic acid and the corresponding 11β-isomer |
| 243 | 15-deoxy-16-hydroxy-20-nor-17-trans-prostaglandin $A_1$ (Example 276) | 11α-(2-hydroxyethylthio)-16-hydroxy-9-oxo-13,17-trans-prostadienoic acid and the corresponding 11β-isomer |
| 244 | nat.-16,16-trimethylene prostaglandin $A_1$ Methyl ester (Example 267) | nat.-methyl 11α-(2-hydroxyethylthio)-15α-hydroxy-9-oxo-16,16-trimethylene-13-trans-prostenoate and the corresponding 11β-isomer |
| 245 | nat. 16,16-trimethylene prostaglandin $A_2$ methyl ester (Example 268) | nat.-methyl 11α-(2-hydroxyethylthio)-15α-hydroxy-9-oxo-16,16-trimethylene-5-cis,13-trans-prostadienoic acid and the corresponding 11β-isomer |
| 246 | nat.-16,16-trimethylene prostaglandin $A_2$ (Example 269) | nat.-11α-(2-hydroxyethylthio)-15α-hydroxy-9-oxo-16,16-trimethylene-5-cis,13-trans-prostadienoic acid and the corresponding 11β-isomer |
| 247 | nat.-16,16-trimethylene prostaglandin $A_1$ (Example 270) | nat.-11α-(2-hydroxyethylthio)-15α-hydroxy-9-oxo-16,16-trimethylene-13-trans-prostenoic acid and the corresponding 11β-isomer |
| 248 | nat.-16,16-trimethylene-20-methyl prostaglandin $A_2$ (Example 271) | nat.-11α-(2-hydroxyethylthio)-15α-hydroxy-9-oxo-16,16-trimethylene-20-methyl-5-cis,13-trans-prostadienoic acid and the corresponding 11β-isomer |
| 249 | nat.-16,16-trimethylene-20-ethyl-prostaglandin $A_2$ (Example 272) | nat.-11α-(2-hydroxyethylthio)-15α-hydroxy-9-oxo-16,16-trimethylene-20-ethyl-5-cis,13-trans-prostadienoic acid and the corresponding 11β-isomer |
| 250 | 15-deoxy-16-hydroxy prostaglandin $A_1$ (U.S. Pat. No. 3,965,143) | 11α-(2-hydroxyethylthio)-16-hydroxy-9-oxo-13-trans-prostenoic acid and the corresponding 11β-isomer |
| 251 | 15-deoxy-16-hydroxy-16-methyl prostaglandin $A_1$,3 methyl ester (U.S. Pat. No. 3,965,143) | methyl-11α-(2-hydroxyethylthio)-16-hydroxy-9-oxo-16-methyl,13-trans-prostenoate acid and the corresponding 11β-isomer |
| 252 | nat.-15-methyl prostaglandin $A_1$ Methyl ester | methyl-nat.-11α-(2-hydroxyethylthio)-15α-hydroxy-9-oxo-15-methyl,13-trans-prostenoate and the corresponding 11β-isomer |
| 253 | nat.-15-methyl-prostaglandin $A_2$ Methyl ester | methyl-nat.-11α-(2-hydroxyethylthio)-15α-hydroxy-9-oxo-15-methyl-5-cis,13-trans-prostadienoate and the corresponding 11β-isomer |
| 254 | nat.-16,16-dimethyl prostaglandin $A_2$ | nat.-11α-(2-hydroxyethylthio)-15α-hydroxy-9-oxo-16,16-dimethyl-5-cis,13-trans-prostadienoic acid and the corresponding 11β-isomer |
| 255 | nat.-16(S)-methyl prostaglandin $A_2$ | nat.-11α-(2-hydroxyethylthio)-15α-hydroxy-9-oxo-16(S)-methyl-5-cis,13-trans-prostadienoic acid and the corresponding 11β-isomer |
| 256 | nat.-prostaglandin $A_3$ (Example 265) | nat.-11α-(2-hydroxyethylthio)-15α-hydroxy-9-oxo-5-cis,13-trans,17-trans-prostatrienoic acid and the corresponding 11β-isomer |
| 257 | nat.-20-methyl prostaglandin $A_2$ (Example 264) | nat.-11α-(2-hydroxyethylthio)-15α-hydroxy-9-oxo-20-methyl-5-cis,13-trans-prostadienoic acid and the corresponding 11β-isomer |
| 258 | nat.-20-ethyl prostaglandin $A_2$ (Example 263) | nat.-11α-(2-hydroxyethylthio)-15α-hydroxy-9-oxo-20-ethyl-5-cis,13-trans-prostadienoic acid and the corresponding 11β-isomer |
| 259 | erythro-16-hydroxy-prostaglandin $A_2$ (Example 277) | erythro-11α-(2-hydroxyethylthio)-15α,16-dihydroxy-9-oxo-5-cis,13-trans-prostadienoic acid and the corresponding 11β-isomer |
| 260 | threo-16-hydroxy prostaglandin $A_2$ (Example 278) | threo-11α-(2-hydroxyethylthio)-15α,16-dihydroxy-9-oxo-5-cis,13-trans-prostadienoic acid and the corresponding 11β-isomer |
| 261 | erythro-16-methoxy- | erythro-11α-(2-hydroxyethylthio)-15α-hydroxy-9-oxo-16- |

TABLE 28-continued

| Example | | |
|---|---|---|
| 262 | prostaglandin $A_2$ (Example 279) threo-16-methoxy-prostaglandin $A_2$ (Example 280) | methoxy-5-cis,13-trans-prostadienoic acid and the corresponding 11$\beta$-isomer threo-11$\alpha$-(2-hydroxyethylthio)-15$\alpha$-hydroxy-9-oxo-16-methoxy-5-cis,13-trans-prostadienoic acid and the corresponding 11$\beta$-isomer |

EXAMPLE 263

Preparation of nat.-20-ethyl prostaglandin $A_2$

A solution of nat.-20-ethyl-9-oxo-11$\alpha$,15(S)-bis-(tetrahydropyran-2-yloxy)-5-cis-13-trans-prostadienoic acid [U.S. Pat. No. 2,150,361 (West Germany, 1972)] in tetrahydrofuran containing 1.5 N hydrochloric acid is kept at ambient temperature for 70 hours. The solution is flooded with saturated sodium chloride and extracted several times with ether. The combined extracts are washed with water, dried with anhydrous magnesium sulfate and taken to dryness to afford the subject compound.

EXAMPLES 264–280

The prostaglandins E of the table below when treated in the manner of Example 263 furnish the corresponding prostaglandins A.

ml of N/1 sodium methoxide in methanol solution during 30 minutes at room temperature. After the addition the solution is stirred at room temperature for 1 hour and treated with 4.8 g of glacial acetic acid (80 mmols). The solution is concentrated to volume of 10 ml, treated with 30 ml of brine, and extracted with ethyl acetate. The extract is washed with brine, dried over magnesium sulfate, and concentrated.

The resulting residue is purified by column chromatography on silica gel with chloroform progressively enriched in ether and finally ether to provide an oil.

EXAMPLE 282

Preparation of Bis-Trimethylsilyl Derivative of 2-(6-carboxy-2-cis-hexenyl)-4-(2-hydroxyethylthio)cyclopent-2-en-1-one To a stirred, ice-cold solution of 1.42 g (5.0 mmols) of 2-(6-carboxy-2-cis-hexenyl)-4-(2-hydroxyethylthio)cy-

TABLE 29

| Example | Starting Prostaglandins E | Product Prostaglandins A |
|---|---|---|
| 264 | Nat.-20-methylprostaglandin-$E_2$[a] | nat.-20-methylprostaglandin-$A_2$ |
| 265 | nat.-prostaglandin-$E_3$ - E.J. Corey, et al. Journ. Amer. Chem. Soc., 93, 1490 (1971) | nat.-prostaglandin-$A_3$ |
| 266 | prostaglandin-$E_2$ - E.J. Corey, et al., Journ. Amer. Chem. Soc., 91, 5675 (1969) | dl-prostaglandin-$A_2$ |
| 267 | nat. 16,16-trimethylene $PGE_1$ methyl ester[b] | nat. 16,16-trimethylene $PGA_1$ methyl ester |
| 268 | nat. 16,16-trimethylene $PGE_2$ methyl ester[b] | nat. 16,16-trimethylene $PGA_2$ methyl ester |
| 269 | nat. 16,16-trimethylene $PGE_2$[b] | nat. 16,16-trimethylene $PGA_2$ |
| 270 | nat. 16,16-trimethylene $PGE_1$[b] | nat. 16,16-trimethylene $PGA_1$ |
| 271 | nat. 16,16-trimethylene-20-methyl $PGE_2$[b] | nat. 16,16-trimethylene-20-methyl $PGA_2$ |
| 272 | nat. 16,16-trimethylene-20-ethyl $PGE_2$[b] | nat. 16,16-trimethylene-20-ethyl $PGA_2$ |
| 273 | 11$\alpha$,16-dihydroxy-17-methyl-9-oxo-13-trans-prostenoic acid[c] | 16-hydroxy-17-methyl-9-oxo-10,13-trans-prostadienoic acid |
| 274 | ethyl 11$\alpha$,16-dihydroxy-17-methyl-9-oxo-13-trans-prostenoic acid[c] | ethyl 16-hydroxy-17-methyl-9-oxo-10,13-trans-prostadienoate |
| 275 | 11$\alpha$,16-dihydroxy-9-oxo-13-trans-prostenoic acid[c] | 16-hydroxy-9-oxo-10,13-trans-prostadienoic acid |
| 276 | 11$\alpha$,16-dihydroxy-9-oxo-20-nor-13,17-trans,trans-prostadienoic acid[c] | 16-hydroxy-9-oxo-20-nor-10,13-trans,17-trans-prostadienoic acid |
| 277 | erythro-11$\alpha$,15$\alpha$,16-trihydroxy-9-oxo-5-cis,13-trans-prostadienoic acid[d] | erythro-15$\alpha$,16-dihydroxy-9-oxo-5-cis,10,13-trans-prostatrienoic acid |
| 278 | threo-11$\alpha$,15$\alpha$,16-trihydroxy-9-oxo-5-cis,13-trans-prostadienoic acid[d] | threo-15$\alpha$,16-dihydroxy-9-oxo-5-cis,10,13-trans-prostatrienoic acid |
| 279 | erythro-11$\alpha$,15$\alpha$-dihydroxy-16-methoxy-9-oxo-5-cis,13-trans-prostadienoic acid[e] | erythro-15$\alpha$-hydroxy-9-oxo-16-methoxy-5-cis,10,13-trans-prostatrienoic acid |
| 280 | threo-11$\alpha$,15$\alpha$-dihydroxy-16-methoxy-5-cis,13-trans-prostadienoic acid[e] | threo-15$\alpha$-hydroxy-9-oxo-16-methoxy-5-cis,10,13-trans-prostatrienoic acid |

[a] D. van Dorp, Annal of the New York Academy of Sciences, Volume 180, 181 (1971).
[b] W. German Patent No. 2,510,818 (March 14, 1974).
[c] U.S. Pat. No. 3,950,406 (April 12, 1976).
[d] Japan Patent No. J5 1008-249 (Derivent 1783ox110) (July 7, 1974).
[e] Japan Patent No. J5 0070-340 (Derivent 61314w137) (October 29, 1973).

EXAMPLE 281

Preparation of 2-(6-carboxy-2-cis-hexenyl)-4-(2-hydroxyethylthio)cyclopent-2-en-1-one To a stirred solution of 2.24 g. (10 mmols) of 2-(6-carboxy-2-cis-hexenyl)-4-hydroxycyclopent-2-en-1-one (U.S. Pat. No. 3,952,033) and 0.82 g (10.5 mmols) of $\beta$-mercaptoethanol in 50 ml of methanol is added 10.5 clopent-2-en-1-one (Example 281) in 10 ml of pyridine is added 2.50 ml of hexamethyldisilazane followed by 1.25 ml of chlorotrimethylsilane. The resulting mixture is stirred at ambient temperature for 4 hours. The volatile materials are evaporated under vacuum, and the resulting residue is stirred with petroleum ether. The mixture is filtered through celite, and the filtrate is concentrated to give a light yellow liquid.

EXAMPLE 283

Preparation of
2-(6-carboxyhexyl)-4-(2-hydroxyethylthio)cyclopent-2-
en-1-one

In the manner of Example 281 a methanol solution of 2-(6-carboxyhexyl)-4-hydroxycyclopent-2-en-1-one [Prostaglandins, 3, 921 (1973)] and β-mercaptoethanol is treated with sodium methoxide solution, acidified, concentrated, and extracted to provide the subject compound as an oil.

EXAMPLE 283a

Preparation of Bis-Trimethylsilyl Derivative of
2-(6-carboxyhexyl)-4-(2-hydroxyethylthio)cyclopent-2-
en-1-one In the manner of Example 281a a solution of 2-(6-carboxyhexyl-4-(2-hydroxyethylthio)cyclopent-2-en-1-one (Example 282) in pyridine is treated with hexamethyldisilazane and chlorotrimethylsilane to provide the subject compound as a liquid.

EXAMPLE 284

Preparation of
2-(6-carboxymethoxy-2-cis-hexenyl)-4-methoxycyclo-
pent-2-en-1-one A stirred solution of 6.28 g (27.8 mmols) of 2-(6-carboxy-2-cis-hexenyl)-4-hydroxycyclopent-2-en-1-one (U.S. Pat. No. 3,952,033) and 7.6 ml of concentrated sulfuric acid is heateed at reflux temperature for 40 hours. The solution is treated with 7.4 g of sodium carbonate, concentrated, and partitioned with ether-brine. The ether extract is washed with brine, dried over magnesium sulfate, and concentrated. The resulting residue is distilled to provide a colorless liquid, b.p. 130°–134° (0.05 mm).

EXAMPLE 285

Preparation of
2-(6-carbomethoxy-2-cis-hexenyl)-4-(2-hydroxyethyl-
thio)cyclopent-2-en-1-one To a stirred solution of 7.57 g (30 mmols) of 2-(6-carbomethoxy-2-cis-hexenyl)-4-methoxycyclopent-2-en-1-one (Example 283) and 2.46 g (31.5 mmols) of β-mercaptoethanol in 150 ml of methanol is added 15 ml of N/10 sodium methoxide in methanol solution. After 50 minutes at room temperature the solution is acidified with 0.27 ml of gl. acetic acid and partitioned with ether-brine. The ether extract is washed with brine, dried over magnesium sulfate, and concentrated. The residue is subjected to column chromatography on silica-gel to provide an oil.

EXAMPLE 286

Preparation of
2-(6-carbomethoxy-2-cis-hexenyl)-4-(2-trimethylsilox-
yethylthio)cyclopent-2-en-1-one To a stirred, ice-cold solution of 2.98 g (10 mmols) of 2-(6-carbomethoxy-2-cis-hexenyl)-4-(2-hydroxyethyl-thio)-cyclopent-2-en-1-one (Example 283a) in 10 ml of pyridine is added 2.50 ml of hexamethyldisilazane followed by 1.25 ml of chlorotrimethylsilane. The resulting mixture is stirred at ambient temperature for 2.5 hours. The volatile materials are evaporated under vacuum, and the resulting residue is stirred with petroleum ether. The mixture is filtered through Celite, and the filtrate is concentrated to give a light yellow liquid.

EXAMPLE 287

Preparation of dl-methyl esters of
11-deoxy-11α-(2-hydroxyethylthio)-15α-prostaglandin
$E_2$ and the 15β-isomer To a stirred solution of 2.48 g (5.0 mmols) of 1-iodo-3-triphenylmethoxy-trans-1-ocetene (Tetrahedron Letters, 1975, 765) in 20 ml of ether at $-78°$ is added 6.25 ml of 1.6M t-butyllithium in pentane during 10 minutes. The solution is stirred at $-78°$ for 1 hour, warmed to $-45°$ during 15 minutes and recooled to $-78°$.

The above solution is treated during 10 minutes with a solution prepared from 653 mg (5.0 mmols) of copper pentyne, 2.1 ml of hexamethylphosphorous triamide, and 15 ml of ether, at a temperature of $-78°$ to $-70°$. The resulting solution is stirred at $-78°$ for 60 minutes and treated during 10 minutes with a solution of 1.48 g (4.0 mmols) of 2-(6-carbomethoxy-2-cis-hexenyl)-4-(2-hydroxyethylthio)cyclopent-2-en-1-one (Example 283b) in 10 ml of ether. After 10 minutes at $-78°$ the solution is warmed to $-45°$ during 10 minutes, maintained at $-45°$ to $-40°$ for 2 hours, recooled to $-78°$, and treated with a solution of 0.60 ml of gl. acetic acid in 10 ml of ether. The mixture is diluted with 100 ml of ether and poured into a stirred, ice-cold mixture of 50 ml of saturated ammonium chloride and 10 ml of 4N hydrochloric acid. The ether phase is separated and washed successively with cold 2N hydrochloric acid, water, and brine. The solution is dried over magnesium sulfate and concentrated.

The residue (3.24 g) is dissolved in a solution of 32 ml of gl. acetic acid, 16 ml of THF, and 8 ml of water, and the solution is heated at 45° for 6 hours and partitioned with half-saturated brine and ether. The ether phase is washed with brine, dried over magnesium sulfate, and concentrated.

The residue is subjected to dry column chromatography on silica gel with the solvent system 60:40:1 benzene-ethyl acetate-acetic acid to provide the more mobile epimer (11-deoxy-11α-(2-hydroxyethylthio)-15-epi-prostaglandin $E_2$,methyl ester) as a light yellow oil, and the more polar epimer (11-deoxy-11α-(2-hydroxyethyl-thio)-prostaglandin $E_2$,methyl ester) as a light yellow oil.

EXAMPLES 288–373

Treatment of ether cyclopentenone 282 or 283 with a lithio cuprate generated from the indicated vinyl iodide of Table 30 by the procedure described in Example 287 followed by chromatography is productive of the separated 15-hydroxy epimers and 16-hydroxy mixtures. When a vinylstannyl molecule is utilized, the lithiation is accomplished in tetrahydrofuran with n-butyllithium (1. equiv.) at $-40°$ to $-20°$ C for 1-3 hours.

TABLE 30

| Example | Starting Olefin | Starting Cyclopentenone | Separated Products |
| --- | --- | --- | --- |
| 288 | 13 | 282 | 11α-(2-hydroxyethylthio)-15α-hydroxy-9-oxo-16,16-trimethylene-5-cis,13-trans-prostadienoic acid and the 15β-epimer |
| 289 | 50 | 282 | 11α-(2-hydroxyethylthio)-15α-hydroxy-9-oxo-16,16- |

TABLE 30-continued

| Example | Starting Olefin | Starting Cyclopentenone | Separated Products |
|---|---|---|---|
| | | | trimethylene-20-methyl-5-cis,13-trans-prostadienoic acid and the 15β-epimer |
| 290 | 51 | 282 | 11α-(2-hydroxyethylthio)-15α-hydroxy-9-oxo-16,16-trimethylene-20-ethyl-5-cis,13-trans-prostadienoic acid and the 15β-epimer |
| 291 | 194 | 282 | 11α-(2-hydroxyethylthio)-16-hydroxy-9-oxo-16-vinyl-5-cis,13-trans-prostadienoic acid |
| 292 | 192 | 282 | 11α-(2-hydroxyethylthio)-16-hydroxy-9-oxo-16-cyclopropyl-5-cis,13-trans-prostadienoic acid |
| 293 | 193 | 282 | 11α-(2-hydroxyethylthio)-16-hydroxy-9-oxo-16-cyclopropyl-20-ethyl-5-cis,13-trans-prostadienoic acid |
| 294 | 195 | 282 | 11α-(2-hydroxethylthio)-16-hydroxy-9-oxo-16-vinyl-20-ethyl-5-cis,13-trans-prostadienoic acid |
| 295 | 76 | 282 | erythro-11α-(2-hydroxyethylthio)-15α,16-dihydroxy-9-oxo-5-cis,13-trans-prostadienoic acid and the 15β-epimer |
| 296 | 74 | 282 | erythro-11α-(2-hydroxyethylthio)-15α-hydroxy-9-oxo-16-methoxy-5-cis,13-trans-prostadienoic acid and the 15β-epimer |
| 297 | 77 | 282 | erythro-11α-(2-hydroxyethylthio)-15α-hydroxy-9-oxo-16-ethoxy-5-cis,13-trans-prostadienoic acid and the 15β-isomer |
| 298 | 84 | 282 | erythro-11α-(2-hydroxyethylthio)-15α,16-dihydroxy-9-oxo-20-methyl-5-cis,13-trans-prostadienoic acid and the 15β-epimer |
| 299 | 85 | 282 | erythro-11α-(2-hydroxyethylthio)-15α,16-dihydroxy-9-oxo-20-ethyl-5-cis,13-trans-prostadienoic acid and the 15β-epimer |
| 300 | 87 | 282 | erythro-11α-(2-hydroxyethylthio)-15α,16-dihydroxy-9-oxo-5-cis,13-trans-17-trans-prostatrienoic acid and the 15β-epimer |
| 301 | 69 | 282 | threo-11α-(2-hydroxyethylthio)-15α,16-dihydroxy-9-oxo-5-cis,13-trans-prostadienoic acid and the 15β-epimer |
| 302 | 89 | 282 | threo-11α-(2-hydroxyethylthio)-15α,16-dihydroxy-9-oxo-20-methyl-5-cis,13-trans-prostadienoic acid and the 15β-epimer |
| 303 | 90 | 282 | threo-11α-(2-hydroxyethylthio)-15α,16-dihydroxy-9-oxo-20-ethyl-5-cis,13-trans-prostadienoic acid and the 15β-isomer |
| 304 | 130 | 282 | 11α-(2-hydroxyethylthio)-16-hydroxy-9-oxo-16-methyl-5-cis,13-trans-prostadienoic acid |
| 305 | 107 | 282 | 11α-(2-hydroxyethylthio)-16-hydroxy-9-oxo-5-cis,13-trans-prostadienoic acid |
| 306 | 144 | 282 | 11α-(2-hydroxyethylthio)-16-hydroxy-9-oxo-17-methyl-5-cis,13-trans-prostadienoic acid |
| 307 | 112 | 282 | 11α-(2-hydroxyethylthio)-16-hydroxy-9-oxo-20-methyl-5-cis,13-trans-prostadienoic acid |
| 308 | 113 | 282 | 11α-(2-hydroxyethylthio)-16-hydroxy-9-oxo-20-ethyl-5-cis,13-trans-prostadienoic acid |
| 309 | 139a | 282 | 11α(2-hydroxyethylthio)-16-hydroxy-9-oxo-16-methyl-20-ethyl-5-cis,13-trans-prostadienoic acid |
| 310 | 137 | 282 | 11α-(2-hydroxyethylthio)-16-hydroxy-9-oxo-16,20-dimethyl-5-cis,13-trans-prostadienoic acid |
| 311 | 139 | 282 | 11α-(2-hydroxyethylthio)-16-hydroxy-9-oxo-16-methyl-5-cis,13-trans-17-trans-prostatrienoic acid |
| 312 | 151 | 282 | 11α-(2-hydroxyethylthio)-16-hydroxy-9-oxo-17-methyl-20-ethyl-5-cis,13-trans-prostadienoic acid |
| 313 | 152 | 282 | 11α-(2-hydroxyethylthio)-16-hydroxy-9-oxo-5-cis,13-trans-17-trans-prostatrienoic acid |
| 314 | 153 | 282 | 11α-(2-hydroxyethylthio)-16(R)-hydroxy-9-oxo-5-cis,13-trans-prostadienoic acid |
| 315 | 154 | 282 | 11α-(2-hydroxyethylthio)-16(S)-hydroxy-9-oxo-5-cis,13-trans-prostadienoic acid |
| 316 | 148a | 282 | 11α-(2-hydroxyethylthio)-16-hydroxy-9-oxo-20-ethyl-5-cis,13-trans-17-trans-prostatrienoic acid |
| 317 | 1-iodo-3-triphenylmethoxy-1-trans-octene (U.S. Pat. No. 3,873,607). | 282 | 11α-(2-hydroxyethylthio)-15α-hydroxy-9-oxo-5-cis,13-trans-prostadienoic acid and the 15β-epimer |
| 318 | 1-iodo-3-triphenylmethoxy-1-trans-nonene (U.S. Pat. No. 3,873,607). | 282 | 11α-(2-hydroxyethylthio)-15α-hydroxy-9-oxo-20-methyl-5-cis,13-trans-prostadienoic acid and the 15β-epimer |
| 319 | 1-iodo-3-triphenylmethoxy-1-trans-decene (U.S. Pat. No. 3,873,607). | 282 | 11α-(2-hydroxyethylthio)-15α-hydroxy-9-oxo-20-ethyl-5-cis,13-trans-prostadienoic acid and the 15β-epimer |
| 320 | 1-iodo-3-triphenylmethoxy-4,4-dimethyl-1-trans-octene (U.S. Pat. No. 3,873,607). | 282 | 11α-(2-hydroxyethylthio)-15α-hydroxy-9-oxo-16,16-dimethyl-5-cis,13-trans-prostadienoic acid and the 15β-epimer |
| 321 | 1-iodo-3-triphenylmethoxy-4- | 282 | 11α-(2-hydroxyethylthio)-15α-hydroxy-9-oxo-16-methyl-5-cis,13-trans-prostadienoic acid and |

TABLE 30-continued

| Example | Starting Olefin | Starting Cyclopentenone | Separated Products |
|---|---|---|---|
| | methyl-1-trans-octene (U.S. Pat. No. 3,876,690). | | the 15β-isomer |
| 322 | 1-iodo-3-triphenylmethoxy-4-ethyl-1-trans-octene (U.S. Pat. No. 3,876,690). | 282 | 11α-(2-hydroxyethylthio)-15α-hydroxy-9-oxo-16-ethyl-5-cis,13-trans-prostadienoic acid and the 15β-epimer |
| 323 | 1-iodo-3-methyl-3-trimethylsilyloxy-trans-1-octene (Example 185) | 282 | 11α-(2-hydroxyethylthio)-15α-hydroxy-9-oxo-15-methyl-5-cis,13-trans-prostadienoic acid and the 15β-epimer |
| 324 | 1-iodo-3-methyl-3-trimethylsilyloxy-trans-1-decene Example 190a) | 282 | 11α-(hydroxyethylthio)-15α-hydroxy-9-oxo-15-methyl-20-ethyl-5-cis,13-trans-prostadienoic acid and the 15β-epimer |
| 325 | 220 | 282 | 11α-(2-hydroxyethylthio)-15-hydroxy-9-oxo-15,19-methylene-20-nor-5-cis,13-trans-prostadienoic acid |
| 326 | 221 | 282 | 11α-(2-hydroxyethylthio)-15-hydroxy-9-oxo-15,18-methylene-19,20-dinor-5-cis,13-trans-prostadienoic acid and the 15β-epimer |
| 327 | 219 | 282 | 11α-(2-hydroxyethylthio)-16-hydroxy-9-oxo-16,20-methylene-5-cis,13-trans-prostadienoic acid |
| 328 | 222 | 282 | 11α-(2-hydroxyethylthio)-16-hydroxy-9-oxo-16,19-methylene-20-nor-5-cis,13-trans-prostadienoic acid |
| 329 | 216 | 282 | 11α-(2-hydroxyethylthio)-15α-hydroxy-9-oxo-15,16-cis-trimethylene-5-cis,13-trans-prostadienoic acid and the 15β-epimer |
| 330 | 139a | 282 | 11α-(2-hydroxyethylthio)-16-hydroxy-9-oxo-20-ethyl-5-cis,13-trans-17-trans-prostatrienoic acid |
| 331 | 13 | 283 | 11α-(2-hydroxyethylthio)-15α-hydroxy-9-oxo-16,16-trimethylene-13-trans-prostenoic acid and the 15β-epimer |
| 332 | 50 | 283 | 11α-(2-hydroxyethylthio)-15α-hydroxy-9-oxo-16,16-trimethylene-20-methyl-13-trans-prostenoic acid and the 15β-epimer |
| 333 | 51 | 283 | 11α-(2-hydroxyethylthio)-15α-hydroxy-9-oxo-16,16-trimethylene-20-ethyl-13-trans-prostenoic acid and the 15β-epimer |
| 334 | 194 | 283 | 11α-(2-hydroxyethylthio)-16-hydroxy-9-oxo-16-vinyl-13-trans-prostenoic acid |
| 335 | 192 | 283 | 11α-(2-hydroxyethylthio)-16-hydroxy-9-oxo-16-cyclopropyl-13-trans-prostenoic acid |
| 336 | 193 | 283 | 11α-(2-hydroxyethylthio)-16-hydroxy-9-oxo-16-cyclopropyl-20-ethyl-13-trans-prostenoic acid |
| 337 | 195 | 283 | 11α-(2-hydroxyethylthio)-16-hydroxy-9-oxo-16-vinyl-20-ethyl-13-trans-prostenoic acid |
| 338 | 76 | 283 | erythro-11α-(2-hydroxyethylthio)-15α,16-dihydroxy-9-oxo-13-trans-prostenoic acid and the 15β-epimer |
| 339 | 74 | 283 | erythro-11α-(2-hydroxyethylthio)-15α-hydroxy-9-oxo-16-methoxy-13-trans-prostenoic acid and the 15β-epimer |
| 340 | 77 | 283 | erythro-11α-(2-hydroxyethylthio)-15α-hydroxy-9-oxo-16-ethoxy-13-trans-prostenoic acid and the 15β-isomer |
| 341 | 84 | 283 | erythro-11α-(2-hydroxyethylthio)-15α,16-dihydroxy-9-oxo-20-methyl-13-trans-prostenoic acid and the 15β-epimer |
| 342 | 85 | 283 | erythro-11α-(2-hydroxyethylthio)-15α,16-dihydroxy-9-oxo-20-ethyl-13-trans-prostenoic acid and the 15β-epimer |
| 343 | 87 | 283 | erythro-11α-(2-hydroxyethylthio)-15α,16-dihydroxy-9-oxo-13-trans-17-trans-prostadienoic acid and the 15β-epimer |
| 344 | 69 | 283 | threo-11α-(2-hydroxyethylthio)-15α,16-dihydroxy-9-oxo-13-trans-prostenoic acid and the 15β-epimer |
| 345 | 89 | 283 | threo-11α-(2-hydroxyethylthio)-15α,16-dihydroxy-9-oxo-20-methyl-13-trans-prostenoic acid and the 15β-epimer |
| 346 | 90 | 283 | threo-11α-(2-hydroxyethylthio)-15α,16-dihydroxy-9-oxo-20-ethyl-13-trans-prostenoic acid and the 15β-isomer |
| 347 | 130 | 283 | 11α-(2-hydroxyethylthio)-16-hydroxy-9-oxo-16-methyl-13-trans-prostenoic acid |
| 348 | 107 | 283 | 11α-(2-hydroxyethylthio)-16-hydroxy-9-oxo-13-trans-prostenoic acid |
| 349 | 144 | 283 | 11α-(2-hydroxyethylthio)-16-hydroxy-9-oxo-17-methyl-13-trans-prostenoic acid |
| 350 | 112 | 283 | 11α-(2-hydroxyethylthio)-16-hydroxy-9-oxo-20-methyl-13-trans-prostenoic acid |
| 351 | 113 | 283 | 11α-(2-hydroxyethylthio)-16-hydroxy-9-oxo-20-ethyl-13-trans-prostenoic acid |
| 352 | 139a | 283 | 11α-(2-hydorxyethylthio)-16-hydroxy-9-oxo-16-methyl-20-ethyl-13-trans-prostenoic acid |
| 353 | 137 | 283 | 11α-(2-hydroxyethylthio)-16-hydroxy-9-oxo-16,20-dimethyl-13-trans-prostenoic acid |
| 354 | 139 | 283 | 11α-(2-hydroxyethylthio)-16-hydroxy-9-oxo-16-methyl-13-trans-17-trans-prostadienoic acid |
| 355 | 151* | 283 | 11α-(2-hydroxyethylthio)-16-hydroxy-9-oxo-17- |

TABLE 30-continued

| Example | Starting Olefin | Starting Cyclopentenone | Separated Products |
|---|---|---|---|
| 356 | 152 | 283 | methyl-20-ethyl-13-trans-prostenoic acid 11α-(2-hydroxyethylthio)-16-hydroxy-9-oxo-13-trans-17-trans-prostadienoic acid |
| 357 | 153 | 283 | 11α-(2-hydroxyethylthio)-16(R)-hydroxy-9-oxo-13-trans-prostenoic acid |
| 358 | 154 | 283 | 11α-(2-hydroxyethylthio)-16(S)-hydroxy-9-oxo-13-trans-prostenoic acid |
| 359 | 148a | 283 | 11α-(2-hydroxyethylthio)-16-hydroxy-9-oxo-20-ethyl-13-trans-17-trans-prostadienoic acid |
| 360 | 1-iodo-3-triphenylmethoxy-1-trans-octene (U.S. Pat. No. 3,873,607). | 283 | 11α-(2-hydroxyethylthio)-15α-hydroxy-9-oxo-13-trans-prostenoic acid and the 15β-epimer |
| 361 | 1-iodo-3-triphenylmethoxy-1-trans-nonene (U.S. Pat. No. 3,873,607) | 283 | 11α-(2-hydroxyethylthio)-15α-hydroxy-9-oxo-20-methyl-13-trans-prostenoic acid and the 15β-epimer |
| 362 | 1-iodo-3-triphenylmethoxy-1-trans-decene (U.S. Pat. No. 3,873,607). | 283 | 11α-(2-hydroxyethylthio)-15α-hydroxy-9-oxo-20-ethyl-13-trans-prostenoic acid and the 15β-epimer |
| 363 | 1-iodo-3-triphenylmethoxy-4,4-dimethyl-1-trans-octene (U.S. Pat. No. 3,873,607). | 283 | 11α-(2-hydroxyethylthio)-15α-hydroxy-9-oxo-16,16-dimethyl-13-trans-prostenoic acid and the 15β-epimer |
| 364 | 1-iodo-3-triphenylmethoxy-4-methyl-1-trans-octent (U.S. Pat. No. 3,876,690). | 283 | 11α-(2-hydroxyethylthio)-15α-hydroxy-9-oxo-16-methyl-13-trans-prostenoic acid and the 15β-isomer |
| 365 | 1-iodo-3-triphenylmethoxy-4-ethyl-1-trans-octent (U.S. Pat. No. 3,876,690). | 283 | 11α-(2-hydroxyethylthio)-15α-hydroxy-9-oxo-16-ethyl-13-trans-prostenoic acid and the 15β-epimer |
| 366 | 1-iodo-3-methyl-3-trimethylsilyl-oxy-trans-1-octene (Example 190) | 283 | 11α-(2-hydroxyethylthio)-15α-hydroxy-9-oxo-15-methyl-13-trans-prostenoic acid and the 15β-epimer |
| 367 | 1-iodo-3-methyl-3-trimethylsilyl-oxy-trans-1-decene (Example 190a) | 283 | 11α-(2-hydroxyethylthio)-15α-hydroxy-9-oxo-15-methyl-20-ethyl-13-trans-prostenoic acid and the 15β-epimer |
| 368 | 220 | 283 | 11α-(2-hydroxyethylthio)-15-hydroxy-9-oxo-15,19-methylene-20-nor-13-trans-prostenoic acid |
| 369 | 221 | 283 | 11α-(2-hydroxyethylthio)-15-hydroxy-9-oxo-15,18-methylene-19,20-dinor-13-trans-prostenoic acid and the 15β-epimer |
| 370 | 219 | 283 | 11α-(2-hydroxyethylthio)-16-hydroxy-9-oxo-16,20-methylene-13-trans-prostenoic acid |
| 371 | 222 | 283 | 11α-(2-hydroxyethylthio)-16-hydroxy-9-oxo-16,19-methylene-20-nor-13-trans-prostenoic acid |
| 372 | 216 | 283 | 11α-(2-hydroxyethylthio)-15α-hydroxy-9-oxo-15,16-cis-trimethylene-13-trans-prostenoic acid and the 15β-epimer |
| 373 | 139a | 283 | 11α-(2-hydroxyethylthio)-16-hydroxy-9-oxo-20-ethyl-13-trans-17-trans-prostadienoic acid |

EXAMPLE 374

Preparation of 1R,2R(and 1S,2S)-1-(trans-2-Iodovinyl)-1-trimethylsilyloxy-2-butylcyclopentane To a mixture of 12.22 g of sodium borohydride and 60.82 g of 2-methyl-2-butene in 450 ml of tetrahydrofuran under nitrogen at 0° C, is added 54.6 ml of boron trifluoride etherate, dropwise over a 20 minute period. The solution is stirred at 0° C for 2 hours and then at room temperature for 30 minutes. This solution is cooled to 0° C and 55.5 g of 1R,2R(and 1S,2S)-1-ethynyl-1-trimethylsilyloxy-2-butylcyclopentane in 50 ml of tetrahydrofuran is added. The mixture is allowed to stand in a cold room overnight. To this mixture at 0° C is added with stirring 112.8 g of trimethylamine oxide over a 20 minute period. The mixture is stirred at room temperature for 90 minutes and then filtered. To the filtrate is added simultaneously a solution of 565 g of sodium hydroxide in 2000 ml of water and a solution of 300 g of iodine in 300 ml of tetrahydrofuran. The mixture is stirred 30 minutes, the organic layer is separated and the aqueous layer is extracted with ether. The combined organic solutions are washed with saturated sodium thiosulfate solution and with saturated sodium chloride solution. The solution is dried with magnesium sulfate and filtered through a pad of silica gel. The solution is removed giving an orange liquid which is chromatographed on a dry column of silica gel giving 59.5 g of the product as a yellow liquid.

EXAMPLE 375

Preparation of 1-(3-Tri-n-butylstannyl-2-trans-propenyl)-1-trimethylsilyloxycyclohexane To a stirred mixture of 31.5 g of 1-propargyl-1-trimethylsilyloxycyclohexane and 150 mg of azobisisobutyronitrile is added 41 ml of tri-n-butyltin hydride. The stirred mixture is heated to about 80° C. The initial exothermic reaction is moderated, and the temperature is subsequently maintained at 130°–135° C for one hour.

The product is distilled to afford 56 g of colorless liquid, bp 150°–160° C (0.15–0.3 mm), pmr (CDCl₃): 6.0 (multiplet, vinyl protons).

EXAMPLE 376

Preparation of 4-Oxo-1-iodo-trans-1-octene

To a stirred suspension of 6.15 g of pyridinium chlorochromate (Tetrahedron Letters, 1975, 2647) in 20 ml of methylene chloride is added 450 mg of sodium acetate. After 5 minutes a solution of 3.64 g of 4-hydroxy-1-iodo-trans-1-octene in 15 ml of methylene chloride is added in one portion. The dark mixture is stirred at room temperature for 75 minutes, diluted with 50 ml of ether, and decanted. The solid sludge is washed repeatedly with ether and decanted. The combined solutions are percolated through Florisil. The solution is concentrated to give an orange liquid, pmr spectrum (CDCl₃): 3.20 (d, j = 7 cps, =CHCH₂CO).

EXAMPLE 377

Preparation of 4-Hydroxy-4-vinyl-1-iodo-trans-1-octene

To a stirred solution of 7.8 ml of vinyl magnesium chloride (2.3M in tetrahydrofuran), at −25° C is added a solution of 3.55 g of 4-oxo-1-iodo-trans-1-octene in 20 ml of tetrahydrofuran during 15 minutes. After the addition, the solution is stirred at −20° C to −15° C for 30 minutes. The reaction is quenched with a mixture of hexane and ice. The aqueous phase is separated and extracted with additional hexane. The combined hexane extracts are washed successively with water and brine. The solution is dried over magnesium sulfate and concentrated. The residue is subjected to dry column chromatography on silica gel with benzene as developing solvent to give a liquid, pmr spectrum (CDCl3): 5.2 (m, terminal CH₂), 5.83 (q, CH=CH₂), 6.13 (d, ICH=), and 6.52 (m, ICM=CH).

EXAMPLE 378

Preparation of E-1-Tri-n-butylstannyl-1-octene

A solution of 10.0 g (0.0908 mol) of 1-octyne, 60 ml of anhydrous toluene, 230 mg of azobisisobutylonitrile (AIBN), and 25 ml (0.0943 mol) of tri-n-butyltin hydride is refluxed under an argon atmosphere for 3 hours. The reaction mixture is cooled to ambient temperature and concentrated in vacuo. The resulting yellow liquid is distilled (bulb to bulb) to give 36.29 (99%) of the stannyl octene as a pale yellow liquid.

EXAMPLE 379

Preparation of dl-11,15-Bisdeoxy-11α-(2-hydroxyethylthio)-PGE₂ methyl ester C-13,14 cis isomer To a stirred solution of 4.49 (0.0054 mol) of vinyl stannane and 12 ml of anhydrous tetrahydrofuran, cooled to −78° C is slowly added 5.2 ml (0.0114 mol) of n-butyllithium. After 15 minutes, the reaction mixture is warmed to −15° C for 1½ hour, recooled to −78° C, and to it is added a solution of 1.70 g (0.0130 mol) of copper (I) pentyne, 7 ml of hexamethylphosphorous triamide (HMPTA), and 20 ml of anhydrous ether. After 1 hour, a solution of 2.0 g (0.00054 mol) of cyclopentenone 15 and 15 ml of anhydrous ether is added. The resulting solution is stirred at this temperature for 30 minutes, warmed to −30° C for 2 hours, recooled to −78° C, and to it is added 5 ml of glacial acetic acid. The reaction mixture is poured into a saturated solution of ammonium chloride and is vigorously stirred for 30 minutes. The aqueous phase is separated and extracted with 150 ml of ether in 2 portions. The combined organic phases are washed with 5% hydrochloric acid solution and brine, and then concentrated in vacuo to give an amber oil. A solution of the oil in 140 ml of acetic acid - tetrahydrofuran-water (4:2:1) is stirred at ambient temperature for 1 hour, diluted with toluene, and concentrated in vacuo to give 6.1 g of amber oil. This oil is applied to a silica-gel dry column (3" × 55"; 2:3 / ethyl acetate: benzene + 2% acetic acid; and 600 ml of eluant is collected).

The more polar isomer (13-cis) is isolated from the column at R_f 0.58–0.65 as 133 mg (6%) of a yellow oil.

The less polar isomer (13-trans) is isolated from the column at R_f 0.73–0.81 as 951 mg (43%) of a yellow oil.

We claim:

1. An optically active compound of the formula:

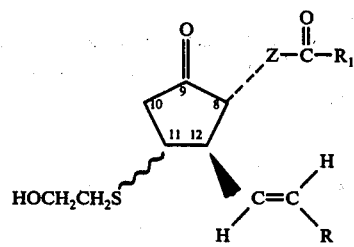

wherein Z is

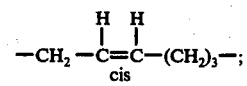

R₁ is selected from the group consisting of hydroxy and C₁–C₆ alkoxy; and R is a moiety selected from the group consisting of

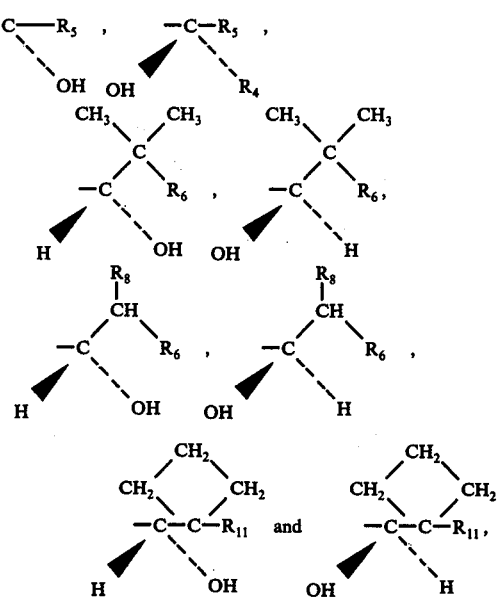

wherein R₄ is selected from the group consisting of hydrogen and methyl, R₅ is selected from the group consisting of C₄–C₇ alkyl and 2-cis(C₄–C₆)alkenyl, R₆ is selected from the group consisting of C₃–C₅ alkyl, R₈ is selected from the group consisting of $C_1$-$C_2$ alkyl, and $R_{11}$ is selected from the group consisting of $C_3$-$C_7$ alkyl; with the proviso that when $R_5$ is 2-cis($C_4$-$C_6$)-alkenyl, then $R_4$ must be hydrogen and Z must be

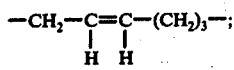

the racemic mixture thereof; the mirror image thereof; and when $R_1$ is hydroxy, the pharmaceutically acceptable salts thereof.

2. An optically active compound according to claim 1, wherein Z, R and $R_1$ are as previously defined; and the substituent at the carbon-11 position is β-(2-hydroxyethylthio).

3. An optically active compound according to claim 1, wherein Z, R and $R_1$ are as previously defined; and the substituent at the carbon-11 position is α-(2-hydroxyethylthio).

4. An optically active compound according to claim 3, wherein Z and $R_1$ are as previously defined; and R is a moiety selected from the group consisting of

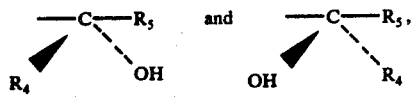

as previously defined.

5. An optically active compound according to claim 3, wherein Z and $R_1$ are as previously defined; and R is a moiety selected from the group consisting of

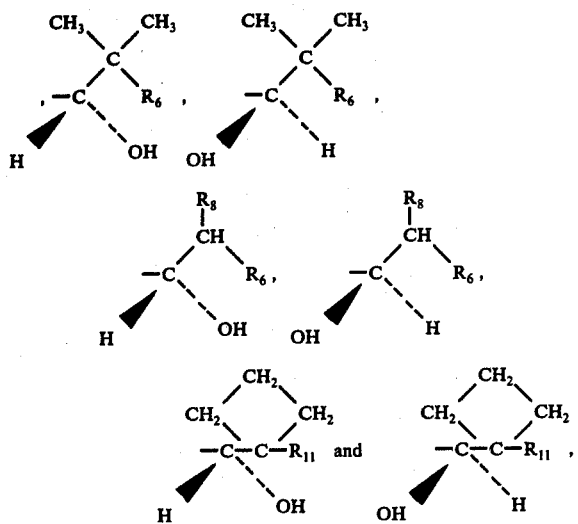

wherein $R_6$, $R_8$ and $R_{11}$ are as previously defined.

6. The optically active compound according to claim 2, nat. 11β-(2-hydroxyethylthio)-15α-hydroxy-9-oxo-5-cis,13-trans,18-cis-prostatrienoic acid.

7. The optically active compound according to claim 2, nat. 11β-(2-hydroxyethylthio)-15α-hydroxy-16(S)-methyl-9-oxo-5-cis,13-trans-prostadienoic acid.

8. The optically active compound according to claim 2, nat. 11β-(2-hydroxyethylthio)-15α-hydroxy-15-methyl-9-oxo-5-cis,13-trans-prostadienoate.

9. The optically active compound according to claim 2, nat. 11β-(2-hydroxyethylthio)-15α-hydroxy-16,16-dimethyl-9-oxo-5-cis,13-trans-prostadienoic acid.

10. The optically active compound according to claim 2, methyl nat. 11β-(2-hydroxyethylthio)-15α-hydroxy-16,16-trimethylene-9-oxo-5-cis,13-trans-prostadienoate.

11. The optically active compound according to claim 2, nat. 11β-(2-hydroxyethylthio)-15α-hydroxy-9-oxo-5-cis,13-trans-prostadeinoic acid.

12. The optically active compound according to claim 2, methyl nat. 11β-(2-hydroxyethylthio)-15α-hydroxy-20-ethyl-9-oxo-5-cis,13-trans-prostadienoate.

13. The optically active compound according to claim 2, methyl nat. 11β-(2-hydroxyethylthio)-15α-hydroxy-20-methyl-9-oxo-5-cis,13-trans-prostadienoate.

14. The optically active compound according to claim 2, methyl nat. 11β-(2-hydroxyethylthio)-15α-hydroxy-9-oxo-5-cis,13-trans-prostadienoate.

15. The optically active compound according to claim 4, methyl nat. 11α-(2-hydroxyethylthio)-15α-hydroxy-20-methyl-9-oxo-5-cis,13-trans-prostadienoate.

16. The optically active compound according to claim 4, methyl nat. 11α-(2-hydroxyethylthio)-15α-hydroxy-20-ethyl-9-oxo-5-cis,13-trans-prostadienoate.

17. The optically active compound according to claim 4, nat. 11α-(2-hydroxyethylthio)-15α-hydroxy-9-oxo-5-cis,13-trans-prostadienoic acid.

18. The optically active compound according to claim 4, nat. 11α-(2-hydroxyethylthio)-15α-hydroxy-9-oxo-5-cis,13-trans,18-cis-prostatrienoic acid.

19. The optically active compound according to claim 4, methyl nat. 11α-(2-hydroxyethylthio)-15α-hydroxy-9-oxo-5-cis,13-trans-prostadienoate.

20. The optically active compound according to claim 5, nat. 11α-(2-hydroxyethylthio)-15α-hydroxy-16(S)-methyl-9-oxo-5-cis,13-trans-prostadienoic acid.

21. The optically active compound according to claim 5, nat. 11α-(2-hydroxyethylthio)-15α-hydroxy-16,16-dimethyl-9-oxo-5-cis,13-trans-prostadienoic acid.

22. The optically active compound according to claim 5, methyl nat. 11α-(2-hydroxyethylthio)-15α-hydroxy-16,16-trimethylene-9-oxo-5-cis,13-trans-prostadienoate.

23. The optically active compound according to claim 5, methyl nat. 11α-(2-hydroxyethylthio)-15α-hydroxy-15-methyl-9-oxo-5-cis,13-trans-prostadienoate.

* * * * *